United States Patent [19]

White et al.

[11] Patent Number: 5,434,147
[45] Date of Patent: Jul. 18, 1995

[54] ANTIMICROBIAL QUINOLONYL [LACTAM] ESTERS

[75] Inventors: Ronald W. White, West Chester, Ohio; Thomas P. Demuth, Jr., Norwich, N.Y.

[73] Assignee: Proctor & Gamble Pharmaceuticals, Inc., Norwich, N.Y.

[21] Appl. No.: 133,704

[22] Filed: Oct. 8, 1993

Related U.S. Application Data

[60] Division of Ser. No. 933,446, Aug. 21, 1992, Pat. No. 5,273,973, which is a division of Ser. No. 693,790, Apr. 29, 1991, Pat. No. 5,180,719, which is a continuation of Ser. No. 418,033, Oct. 12, 1989, abandoned, which is a continuation-in-part of Ser. No. 261,798, Oct. 24, 1988, abandoned.

[51] Int. Cl.⁶ ............... C07D 471/04; A61K 31/435
[52] U.S. Cl. ..................... 514/210; 540/205; 540/310; 540/222
[58] Field of Search ............ 514/210; 540/222, 205

[56] References Cited

U.S. PATENT DOCUMENTS

| | | | |
|---|---|---|---|
| 4,146,719 | 3/1979 | Irikura | 544/363 |
| 4,620,007 | 10/1986 | Grohe et al. | 546/156 |
| 4,631,150 | 12/1986 | Grohe et al. | 546/156 |
| 4,670,444 | 6/1987 | Grohe et al. | 514/300 |
| 4,742,053 | 5/1988 | Nakagawa et al. | 514/202 |
| 4,904,647 | 2/1990 | Kulcsar et al. | 514/154 |
| 5,013,730 | 5/1991 | Arnould et al. | 514/202 |
| 5,013,731 | 5/1991 | Arnould et al. | 514/202 |
| 5,147,871 | 9/1992 | Albrecht et al. | 540/222 |
| 5,180,719 | 1/1993 | White et al. | 514/190 |
| 5,273,973 | 12/1993 | White et al. | 514/210 |

FOREIGN PATENT DOCUMENTS 8775009 1/1988 Australia.

(List continued on next page.)

OTHER PUBLICATIONS

Uglesic et al., "New Semisynthetic Penicillins", *Advan. Antimicrob. Antineoplastic Chemother., Proc. Int. Congr. Chemother.*, 7th, Meeting Date 1971, vol. 1, 997 (1972) (*Chemical Abstracts* 79:61968).

O'Callaghan, et al., "A New Cephalosporin with a Dual Mode of Action", 10 *Antimicrobial Agents and Chemotherapy* 245 (1976).

Greenwood et al., "Dual-Action Cephalosporin Utilizing a Novel Therapeutic Principle", 10 *Antimicrobial Agents and Chemotherapy* 249 (1976).

Yamada et al., "New Broad-Spectrum Cephalosporins with Antipseudomonal Activity", 36 *J. Antibiotics* 532 (1983) (*Chemical Abstracts* 99:87869).

Hirose et al., "Desulfurization of 7-Aminodeacetoxycephalosporanic Acid", 104 *Yakugaku Zasshi* 302 (1984) (*Chemical Abstract* 101:110596).

Cimarusti et al., "Monocyclic β-Lactam Antibiotics", 4 *Medicinal Research Reviews* 1 (1984).

Dürckheimer et al., "Recent Developments in the Field of β-Lactam Antibiotics", 24 *Angew. Chem. Int. Ed. Engl.* 180 (1985).

(List continued on next page.)

*Primary Examiner*—Nicholas Rizzo
*Attorney, Agent, or Firm*—David L. Suter; Karen F. Clark

[57] ABSTRACT

Antimicrobial quinolonyl lactam esters comprising a lactam-containing moiety linked, by an ester group, to the 3-carboxy group of a quinolone moiety. These compounds are of the formula:

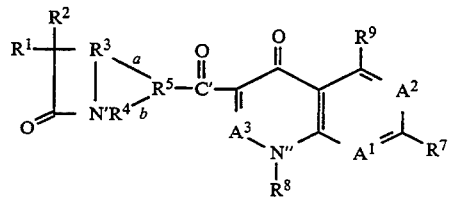

wherein
(1) $R^3$, $R^4$, and $R^5$, together with bonds "a" and "b", form certain lactam-containing moieties similar to those known in the art to have antimicrobial activity; and
(2) A, $R^6$, $R^7$, and $R^8$ form any of a variety of quinolone or napthyridine structures similar to those known in the art to have antimicrobial activity.

29 Claims, No Drawings

FOREIGN PATENT DOCUMENTS

| | | |
|---|---|---|
| 8827554 | 6/1989 | Australia . |
| 53816 | 6/1982 | European Pat. Off. . |
| 62328 | 10/1982 | European Pat. Off. . |
| 203559 | 12/1986 | European Pat. Off. . |
| 0304158 | 2/1989 | European Pat. Off. . |
| 335297 | 10/1989 | European Pat. Off. . |
| 341990 | 11/1989 | European Pat. Off. . |
| 0366189 | 5/1990 | European Pat. Off. . |
| 0366193 | 5/1990 | European Pat. Off. . |
| 0366640 | 5/1990 | European Pat. Off. . |
| 0366643 | 5/1990 | European Pat. Off. . |
| 0451764 | 10/1991 | European Pat. Off. . |
| 0453924 | 10/1991 | European Pat. Off. . |
| 0453952 | 10/1991 | European Pat. Off. . |
| 2191556 | 3/1974 | France . |
| 2243940 | 4/1975 | France . |
| 1940511 | 3/1970 | Germany . |
| 2322750 | 11/1972 | Germany . |
| 2448966 | 4/1975 | Germany . |
| 2514322 | 10/1975 | Germany . |
| 2947948 | 6/1980 | Germany . |
| 3345093 | 6/1984 | Germany . |
| 57-11237 | 4/1972 | Japan . |
| 59-35392 | 4/1974 | Japan . |
| 50-23036 | 8/1975 | Japan . |
| 50-23037 | 8/1975 | Japan . |
| 8232290 | 2/1982 | Japan . |
| 8246988 | 3/1982 | Japan . |
| 8246990 | 3/1982 | Japan . |
| 60-06617 | 1/1985 | Japan . |
| 1258684 | 10/1989 | Japan . |
| 8705297 | 9/1987 | WIPO . |
| 9116310 | 10/1991 | WIPO . |
| 9116327 | 10/1991 | WIPO . |

OTHER PUBLICATIONS

Wolfson et al., "Minireview—The Fluoroquinolones: Structures, Mechanisms of Action and Resistance, and Spectra of Activity In Vitro", 28 *Antimicrobial Agents and Chemotherapy* 581 (1985).

Mobashery et al., "Conscripting β-Lactamase for Use in Drug Delivery. Synthesis and Biological Activity of a Cephalosporin $C_{10}$-Ester of an Antibiotic Dipeptide", 108 *J. American Chemical Society* 1685 (1986).

Mobashery et al., "Reactions of *Escherichia coli* TEM β-Lactamase with Cephalothin and with $C_{10}$-Dipeptidyl Cephalosporin Esters", 261 *J. Biological Chemistry* 7879 (1986).

Rolinson, "β-Lactam antibiotics", 17 *J. Antimicrobial Chemotherapy* 5 (1986).

Wise, "Minireview—In Vitro and Pharmacokinetic Properties of the Carbapenems", 30 *Antimicrobial Agents and Chemotherapy* 343 (1986).

Mobashery et al., "Inactivation of Alanine Racemase by β-Chloro-L-alanine Released Enzymatically from Amino Acid and Peptide $C_{10}$ Esters of Deacetylcephalothin", 26 *Biochemistry* 5878 (1987).

Thabaut et al., "Beta-lactam Antibiotic—New Quinolone Combinations", 16 *Presse Med.*, 2167 (1987) (*Chemical Abstracts* 108:147028).

Le Noc et al., "Activite Antibacterienne in vitro du Cefpirome en Association Avec Quatre Aminoglycosides et Deux Fluoroquinolones", 36 *Path. Biol.* 762 91988).

McCombie et al., "Synthesis and In Vitro Activity of the Penem Antibiotics", 8 *Medicinal Research Reviews* 393 (1988).

Albrecht et al., "Dual-Action Cephalosporins: An Idea Whose Time Has Come", *Program and Abstracts of the Twenty-Eighth Interscience Conference on Antimicrobial Agents and Chemotherapy* 186 (American Society for Microbiology, 1988).

Georgopapadakou et al., "Cephalosporin-Quinolone Esters: Biological Properties", *Program and Abstracts of the Twenty-Eighth Interscience Conference on Antimicrobial Agents and Chemotherapy* 186 (American Society for Microbiology, 1988).

Christenson et al., "Hydrolysis of Ro 23-9424 by β-Lactamases", *Program and Abstracts of the Twenty-Eighth Interscience Conference on Antimicrobial Agents and Chemotherapy* 187 (American Society for Microbiology, 1988).

Christenson et al., "Mode of Action of Ro 23-9424, a Dual-Action Cephalosporin", *Program and Abstracts of the Twenty-Eighth Interscience Conference on Antimicrobial Agents and Chemotherapy* 187 (American Society for Microbiology, 1988).

Georgopapadakou et al., "Mode of Action of the Dual-Action Cephalosporin Ro 23-9424", *Program and Abstracts of the Twenty-Eighth Interscience Conference on Antimicrobial Agents and Chemotherapy* 187 (American Society for Microbiology, 1988).

Jones et al., "Antimicrobial Activity of Ro 23-9424, a Novel Ester Fusion of Fleroxacin and Desacetyl-Cefotaxime", *Program and Abstracts of the Twenty-Eighth Interscience Conference on Antimicrobial Agents and Chemotherapy* 187 (American Society for Microbiology, 1988).

Beskid et al., "In Vitro Antibacterial Activity of Duas-Action Cephalosporin Ro 23-9424 and Comparative Agents", *Program and Abstracts of the Twenty-Eighth Interscience Conference on Antimicrobial Agents and Chemotherapy* 187 (American Society for MicroBiology, 1988).

(List continued on next page.)

OTHER PUBLICATIONS

Beskid et al., "In Vitro Antibacterial Activity of Dual-Action Cephalosporin Ro 23-9424 Compared to Cefotaxime and Fleroxacin", *Program and Abstracts of the Twenty-Eighth Interscience Conference on Antimicrobial Agents and Chemotherapy* 187 (American Society for Microbiology, 1988).

Christenson et al., "Pharmacokinetics of Ro 23-9424, a Dual-Action Cephalosporin in Animals", *Program and Abstracts of the Twenty-Eighth Interscience Conference on Antimicrobial Agents and Chemotherapy* 188 (American Society for Microbiology, 1988).

Christenson et al., "Mode of Action of Ro 23-5068, a Dual-Action Cephalosporin", *Program and Abstracts of the Twenty-Eighth Interscience Conference on Antimicrobial Agents and Chemotherapy* 188 (American Society for Microbiology, 1988).

Albrecht et al., "Dual-Action Cephalosporins: An Idea Whose Time Has Come", Poster Session: 28th Interscience Conference on Antimicrobial Agents and Chemotherapy (Oct. 24, 1988).

Georgopapadakou et al., "Cephalosporin-Quinolone Esters: Biological Properties", Poster Session: 28th Interscience Conference on Antimicrobial Agents and Chemotherapy (Oct. 24, 1988).

Christenson et al., "Hydrolysis of Ro 23-9424 by $\beta$-Lactamases", Poster Session: 28th Interscience Conference on Antimicrobial Agents and Chemotherapy (Oct. 24, 1988).

Christenson et al., "Mode of Action of Ro 23-9424, a Dual Action Cephalosporin", Poster Session: 28th Interscience Conference on Antimicrobial Agents and Chemotherapy (Oct. 24, 1988).

Georgopapapadakou et al., "Mode of Action of the Dual-Action Cephalosporin Ro 23-9424", Poster Session: 28th Interscience Conference on Antimicrobial Agents and Chemotherapy (Oct. 24, 1988).

Beskid et al., "In Vitro Antibacterial Activity of Dual-Action Cephalosporin Ro 23-9424 and Comparative Agents", Poster Session: 28th Interscience Conference on Antimicrobial Agents and Chemotherapy (Oct. 24, 1988).

Beskid et al., "In Vitro Antibacterial Activity of Dual-Action Cephalosporin Ro 23-9424 Compared to Cefotaxime and Fleroxacin", Poster Session: 28th Interscience Conference on Antimicrobial Agents and Chemotherapy (Oct. 24, 1988).

Christenson et al., "Pharmacokinetics of Ro 23-9424, a Dual-Action Cephalosporin, in Animals", Poster Session: 28th Interscience Conference on Antimicrobial Agents and Chemotherapy (Oct. 24, 1988).

Christenson et al., "Mode of Action of Ro 23-5068, a Dual-Action Cephalosporin", Poster Session: 28th Interscience Conference on Antimicrobial Agents and Chemotherapy (Oct. 24, 1988).

Georgopapadakou et al., "Mode of Action of the Dual-Action Cephalosporin Ro 23-9424", 33 *Antimicrobial Agents and Chemotherapy* 1067 (1989).

Cleeland et al., "Dual-Action Antibacterials: A Concept Newly Recognized for Antibacterial Chemotherapy", 6 Antimicrobic Newsletter 61 (1989).

Albrecht et al., "Dual-Action Cephalosporins: Cephalosporin-3'-Quaternary Quinolones", Program and Abstracts of the Twenty-Ninth Interscience Conference on Antimicrobial Agents and Chemotherapy (American Society for Microbiology, 1989).

Perrone, E. et al., "Dual Action Penems", Abstract #825; Abstracts of the 1991 ICAAC (Abstract only).

Albrecht, H. A., "Dual-Action Cephalosporins Incorporating 3'-Tertiary Amine-Linked Quinolones", 31st Interscience Conference on Antibacterial Agents and Chemotherapy, Chicago, Ill.; Poster Session: Oct. 2, 1991(Abs. & Poster).

Corraz, A. J. et al., "Dual-Action Penems and Carbapenems", Abstract #826 Poster #73 31st Interscience Conference on Antimicrobial Agents and Chemotherapy (Chicago, Ill., Oct. 1, 1991 (Abstract & Poster).

Schaefer, F. F. et al., "The Role of AMPC b-Lactamase in the Mechanism of Action of Ester-Linked Dual-Action Cephalosporins", Abstract #953, 31st Interscience Conference on Antimicrobial Agents and Chemotherapy, Poster Session, Oct. 1, 1991 (Abstract & Poster).

Bartkovitz, D., et al., "The Synthesis and Biological Properties of 2a-Methyl Substituted Penicillins", Abstract #824, 31st Interscience Conference on Antibacterial Agents and Chemotherapy (Chicago, Ill.), Oct. 1, 1991 (Abstract & Poster).

Demuth, T. P., et al., "Synthesis and Antibacterial Activity of New C-10 Quinolonyl-Cephem Esters", the Journal of Antibiotics, vol. 44., No. 2, pp. 200-209, Feb. 1991.

ANTIMICROBIAL QUINOLONYL [LACTAM] ESTERS

This is a divisional of application Ser. No. 07/933,446 filed on Aug. 21, 1992, which issued Dec. 29, 1993 as U.S. Pat. No. 5,273,973, which is a divisional of application Ser. No. 07/693,790 filed on Apr. 29, 1991, which issued Jan. 19, 1993 as U.S. Pat. No. 5,180,719, which is a continuation of application Ser. No. 7/418,033, filed Oct. 12, 1989, abandoned, which was a continuation-in-part of application Ser. No. 07/261,798 filed Oct. 24, 1988, abandoned.

BACKGROUND OF THE INVENTION

This invention relates to novel antimicrobial compounds and compositions. The compounds of this invention contain a quinolone moiety and a lactam-containing moiety, in a new chemical entity.

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring (antibiotic), synthetic, or semi-synthetic compounds. They may be classified (for example) as the aminoglycosides, ansamacrolides, beta-lactams (including penicillins and cephalosporins), lincosaminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981), both incorporated by reference herein.

The mechanism of action of these antibacterials vary. However, each can be generally classified as functioning in one or more of four ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. On the other hand, quinolones act by inhibiting synthesis of bacterial DNA, thus preventing the bacteria from replicating.

Not surprisingly, the pharmacological characteristics of antibacterials and other antimicrobials, and their suitability for any given clinical use, also vary considerably. For example, the classes of antimicrobials (and members within a class) may vary in their relative efficacy against different types of microorganisms, and their susceptibility to development of microbial resistance. These antimicrobials may also differ in their pharmacological characteristics, such as their bioavailability, and biodistribution. Accordingly, selection of an appropriate antibacterial (or other antimicrobial) in any given clinical situation can be a complicated analysis of many factors, including the type of organism involved, the desired method of administration, and the location of the infection to be treated.

The development of microbial resistance is one factor in the selection of an appropriate antimicrobial (particularly antibacterials), which is of increasing concern in medical science. This "resistance" can be defined as existence of organisms, within a population of a given microbial species, that are less susceptible to the action of a given antimicrobial agent. Such resistant strains may subvert the mechanism of action of a particular antimicrobial, or chemically degrade the antimicrobial before it can act. For example, bacterial resistance to beta-lactam antibacterials has arisen through development of bacterial strains that produce beta-lactamase enzymes, which degrade the antibacterial.

In part as a result of the intense use of antibacterials over extended periods of time, many highly resistant strains of bacteria have evolved. This is of particular concern in environments such as hospitals and nursing homes, which are characterized by relatively high rates of infection and intense use of antibacterials. See, e.g., W. Sanders, Jr. et al., "Inductible Beta-lactamases: Clinical and Epidemiologic Implications for Use of Newer Cephalosporins", 10 *Reviews of Infectious Diseases* 830 (1988). Indeed, the development of resistant bacterial strains has led to a concern that pathogenic bacteria may be produced that are essentially resistant to even the newest developed antibacterial agents.

The literature describes many attempts to enhance the efficacy of antimicrobials, and to overcome the development of microbial resistance. Many such attempts involve the combination of antimicrobials. For example, Thabaut et al., 16 *Presse Med.* 2167 (1987) describes combinations of pefloxacin (a quinolone) with the beta-lactams cefotaxime and cefsulodin. Lenoc et al., 36 *Path. Biol.* 762 (1988), describes combined use of cephems with aminoglycosides, and with quinolones. Japanese Patent Publication 60/06,617, published Jan. 14, 1985, also describes compositions containing beta-lactams and quinolones. O'Callaghan et al., 10 *Antimicrobial Agents and Chemotherapy* 245 (1976), describes a mercapto pyridine-substituted cephem, which is said to liberate an active antimicrobial agent when the cephalosporin is hydrolyzed by beta-lactamase. Mobashery et al., 108 *J. American Chemical Society* 1684 (1986), presents a theory of employing bacterial beta-lactamase in situ to release an antibacterially-active leaving group from the 10-position of a cephem.

However, many such attempts to produce improved antimicrobials yield equivocal results. Indeed, few antimicrobials are produced that are truly clinically-acceptable in terms of their spectrum of antimicrobial activity, avoidance of microbial resistance, and pharmacology.

SUMMARY OF THE INVENTION

The present invention provides compounds of the formula:

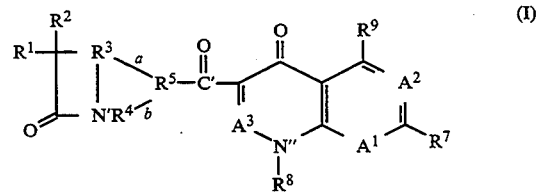

wherein (A) $R^1$ is hydrogen, halogen, alkyl, alkenyl, heteroalkyl, a carbocyclic ring, a heterocyclic ring, $R^{10a}$—O—, $R^{10a}$CH=N—, ($R^{10}$) ($R^{11}$)N—, $R^{12}$—C(=CHR$^{15}$)—C(=O)NH—, $R^{12}$—C(=NO—R$^{14}$)—C(=O)NH—, or $R^{13}$—(CH$_2$)$_m$—C(=O)NH—; where (1) m is an integer from 0 to 9;

(2) $R^{10}$ and $R^{11}$ are, independently, $R^{10a}$ where $R^{10a}$ is hydrogen, alkyl, alkenyl, a carbocyclic ring, or a heterocyclic ring substituent; or $R^{10}$ and $R^{11}$ together comprise a heterocyclic ring including the nitrogen to which they are bonded;

(3) $R^{12}$ is hydrogen, alkyl, alkenyl, heteroalkyl, heteroalkenyl, a carbocyclic ring, or a heterocyclic ring;

(4) $R^{13}$ is $R^{12}$, —$Z^1$, or —CH($Z^2$) ($R^{12}$);

(5) $R^{14}$ is $R^{12}$, arylalkyl, heteroarylalkyl, —C($R^{17}$)($R^{18}$)COOH, —C(=O)O—$R^{12}$, or —C(=O)NH—$R^{12}$, where $R^{17}$ and $R^{18}$ are, independently, $R^{12}$ or together comprise a carbocyclic ring or a heterocyclic ring including the carbon atom to which $R^{17}$ and $R^{18}$ are bonded;

(6) $R^{15}$ is $R^{14}$, halogen, —$Z^1$, or —CH($Z^2$) ($R^{12}$)

(7) $Z^1$ is —C(=O)O$R^{16}$, —C(=O)$R^{16}$, —N($R^{19}$)$R^{16}$, —S(O)$_p$$R^{24}$, or —O$R^{24}$; and $Z^2$ is $Z^1$ or —OH, —SH, or —SO$_3$H;

(a) p is an integer from 0 to 2;

(b) $R^{19}$ is hydrogen; alkyl; alkenyl; heteroalkyl; heteroalkenyl; a carbocyclic ring; a heterocyclic ring; —SO$_3$H; —C(=O)$R^{20}$; or, when $R^{13}$ is —CH($Z^2$) ($R^{12}$) and $Z^2$ is —N($R^{19}$)$R^{16}$, $R^{19}$ may comprise a moiety bonded to $R^{16}$ to form a heterocyclic ring; and (c) $R^{20}$ is $R^{12}$, NH($R^{12}$), N($R^{12}$) ($R^{21}$), O($R^{21}$), or S($R^{21}$); where $R^{21}$ is alkyl, alkenyl, a carbocyclic ring, a heterocyclic ring, or when $R^{20}$ is N($R^{12}$) ($R^{21}$) $R^{21}$ may be a moiety bonded to $R^{12}$ to form a heterocyclic ring; and (8) $R^{16}$ is $R^{24}$ or hydrogen; where $R^{24}$ is alkyl; alkenyl; arylalkyl; heteroalkyl; heteroalkenyl; heteroarylalkyl; a carbocyclic ring; a heterocyclic ring; or, when $Z^1$ is N($R^{19}$)$R^{16}$ and $R^{16}$ is $R^{24}$, $R^{16}$ and $R^{19}$ may together comprise a heterocyclic ring including the nitrogen atom to which $R^{19}$ is bonded;

(B) $R^2$ is hydrogen, halogen, alkoxy, or $R^{22}$C(=O)NH—, where $R^{22}$ is hydrogen or alkyl;

(C) bond "a" is a single bond or is nil; and bond "b" is a single bond, a double bond, or is nil; except bond "a" and bond "b" are not both nil;

(D) $R^3$ is —C($R^{10a}$)—, or —CH$_2$—$R^{23}$—; where $R^{23}$ is —C($R^{10a}$), —O—, or —N—, and $R^{23}$ is directly bonded to N' in Formula (I) to form a 5-membered ring; except, if bond "a" is nil, then $R^3$ is (1) —C($R^{10a}$) ($Z^3$)—, where (i) $Z^3$ is —$R^{16}$, —O$R^{25}$, —S(O)$_r$$R^{25}$, where r is an integer from 0 to 2, —OC(=O)$R^{25}$, or —N($R^{25}$)$R^{26}$;

(ii) $R^{25}$ and $R^{26}$ are, independently, alkyl, alkenyl, carbocyclic ring or heterocyclic ring substituents; or $R^{25}$ and $R^{26}$ together comprise a heterocyclic ring including the nitrogen atom to which $R^{25}$ and $R^{26}$ are bonded; or (2) —CH$_2$—$R^{27}$—; where $R^{27}$ is —C($R^{10a}$) ($R^{16}$), —O—, or —NR$^{10a}$, and $R^{27}$ is directly bonded to N' in Formula (I) to form a 5-membered ring;

(E)

(1) if bond "b" is a single bond, $R^4$ is —CH($R^{28}$)—; or, if bond "a" is nil; —C(O)NHSO$_2$—; or —C*($R^{28}$)—; if $R^5$ contains an $R^{32}$ moiety; where $R^{28}$ is hydrogen or COOH, and C* is linked to $R^{32}$ to form a 3-membered ring;

(2) if bond "b" is a double bond, $R^4$ is —C($R^{28}$)=; or (3) if bond "b" is nil, $R^4$ is hydrogen, —SO$_3$H, —PO(O$R^{29}$)OH, —C(O)NHSO$_2$N($R^{29}$) ($R^{30}$), —OSO$_3$H, —CH($R^{30}$)COOH, or —OCH($R^{29}$)COOH; where $R^{29}$ is hydrogen, alkyl, alkenyl, a carbocyclic ring, or a heterocyclic ring; and $R^{30}$ is hydrogen, alkyl, alkenyl, or —NH$R^{10a}$; or, if $R^4$ is —C(O)NHSO$_2$N($R^{29}$) ($R^{30}$), $R^{29}$ and $R^{30}$ may together comprise a heterocyclic ring including the nitrogen to which $R^{29}$ and $R^{30}$ are bonded; and (F)

(1) if bond "a" or bond "b" is nil, then $R^5$ is Y;

(2) if bond "a" and "b" are single bonds, $R^5$ is —$X^2$—C'''=C($R^{10a}$)—$R^{31}$—Y—, or —$X^2$—C'''($R^{32}$)—$R^{31}$—Y—; or (3) if bond "a" is a single bond and bond "b" is a double bond, $R^5$ is —C($R^{10a}$) ($R^{33}$)—$X^2$—C'''—$R^{31}$—Y—; —$X^1$—C($R^{10a}$) ($R^{33}$)—C'''—$R^{31}$—Y—; or —$X^2$—C'''—$R^{31}$—Y—; where (a) $X^1$ is O or C($R^{33}$), where $R^{33}$ is hydrogen, alkyl or alkoxy;

(b) $X^2$ is O ; S(O)$_s$, where s is an integer from 0 to 2; or C($R^{33}$);

(c) $R^{31}$ is nil, alkyl, alkenyl, a carbocyclic ring, or a heterocyclic ring;

(d) $R^{32}$ is hydrogen; alkyl; alkenyl; —COOH; or, if $R^4$ is —C*($R^{28}$), $R^{32}$ may be linked to C* to form a 3-membered carbocyclic ring;

(e) Y is o or $Z^4$—$R^{34}$—O, where (1) $Z^4$ is —O—; —S(O)$_t$—, where t is an integer of 0 to 2; or —NR$^{10a}$—; and (2) $R^{34}$ is alkyl, alkenyl, heteroalkyl, heteroalkenyl, a carbocyclic ring, or a heterocyclic ring; and (3) Y is directly bonded to C'

(f) C''' is bonded to $R^4$ to form a 5- or 6-membered ring;

(G)

(1) $A^1$ is N or C($R^{40}$); where $R^{40}$ is hydrogen, hydroxy, alkoxy, nitro, cyano, halogen, alkyl, or N($R^{10}$) ($R^{11}$), and (2) $A^2$ is N or C($R^6$); where $R^6$ is hydrogen or halogen;

(3) $A^3$ is N or C($R^{41}$); where $R^{41}$ is hydrogen;

(4) $R^8$ is hydrogen, alkyl, a carbocyclic ring, a heterocyclic ring, alkoxy, hydroxy, alkenyl, arylalkyl, or N($R^{10}$) ($R^{11}$);

(5) $R^7$ is hydrogen, halogen, alkyl, a carbocyclic ring, or a heterocyclic ring; and (7) $R^9$ is hydrogen, halogen, nitro, or N($R^{10}$) ($R^{11}$);

(H) except that (1) when $A^1$ is C($R^{40}$), $R^8$ and $R^{40}$ may together comprise a heterocyclic ring including N'' and $A^1$;

(2) when $A^2$ is C($R^6$), $R^6$ and $R^7$ may together comprise —O—(CH$_2$)$_n$—O—, where n is an integer from 1 to 4; and (3) when $A^3$ is C($R^{41}$), $R^8$ and $R^{41}$ may together comprise a heterocyclic ring including N'' and the adjacent carbon to which $R^{41}$ is bonded;

and pharmaceutically-acceptable salts and biohydrolyzable esters thereof, and hydrates thereof.

It has been found that the compounds of this invention, and compositions containing these compounds, are effective antimicrobial agents against a broad range of pathogenic microorganisms. These compounds provide advantages versus antimicrobial agents among those known in the art, including (for example) the spectrum of antimicrobial activity, potency, the avoidance of microbial resistance, reduced toxicity, and improved pharmacology.

DESCRIPTION OF THE INVENTION

The present invention encompasses certain novel quinolonyl lactam esters, methods for their manufacture, dosage forms, and methods of administering the quinolonyl lactam esters to a human or other animal subject. Specific compounds and compositions to be used in the invention must, accordingly, be pharmaceutically acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio.

Quinolonyl Lactam Esters

The compounds of this invention, herein referred to as "quinolonyl lactam esters", encompass any of a variety of lactam-containing moieties linked, by an ester linkage, to the 3-carboxy group of a quinolone moiety. These compounds include those of the formula:

$$(I)$$

wherein (A) $R^1$ is hydrogen, halogen, alkyl, alkenyl, heteroalkyl, a carbocyclic ring, a heterocyclic ring, $R^{10a}$—O—, $R^{10a}$CH=N—, $(R^{10})(R^{11})$N—, $R^{12}$—C(=CHR$^{15}$)—C(=O)NH—, or (preferably) $R^{12}$—C(=NO—R$^{14}$)—C(=O)NH—, or $R^{13}$—(CH$_2$)$_m$—C(=O)NH—; where (1) m is an integer from 0 to 9 (preferably 0 to 3);
(2) $R^{10}$ and $R^{11}$ are, independently, $R^{10a}$ where $R^{10a}$ is hydrogen, alkyl, alkenyl, a carbocyclic ring, or a heterocyclic ring substituent; or $R^{10}$ and $R^{11}$ together comprise a heterocyclic ring including the nitrogen to which they are bonded;
(3) $R^{12}$ is hydrogen, alkyl, alkenyl, heteroalkyl, heteroalkenyl, a carbocyclic ring, or a heterocyclic ring (preferably alkyl, a carbocyclic ring, or a heterocyclic ring);
(4) $R^{13}$ is $R^{12}$, —Z$^1$, or —CH(Z$^2$) (R$^{12}$);
(5) $R^{14}$ is $R^{12}$, arylalkyl, heteroarylalkyl, —C(R$^{17}$)(R$^{18}$)COOH, —C(=O)O—R$^{12}$, or —C(=O)N-H—R$^{12}$, where $R^{17}$ and $R^{18}$ are, independently, $R^{12}$ or together comprise a carbocyclic ring or a heterocyclic ring including the carbon atom to which $R^{17}$ and $R^{18}$ are bonded (preferably $R^{12}$ or —C(R$^{17}$) (R$^{18}$)COOH;
(6) $R^{15}$ is $R^{14}$, halogen, —Z$^1$, or —CH(Z$^2$) (R$^{12}$) (preferably $R^{19}$ or halogen);
(2) $Z^1$ is —C(=O)OR$^{16}$, —C(O)R$^{16}$, —N(R$^{19}$)R$^{16}$, —S(O)$_p$R$^{24}$, or —OR$^{24}$; and Z$^2$ is Z$^1$ or —OH, —SH, or —SO$_3$H;
  (a) p is an integer from 0 to 2 (preferably 0);
  (b) $R^{19}$ is hydrogen; alkyl; alkenyl; heteroalkyl; heteroalkenyl; a carbocyclic ring; a heterocyclic ring; —SO$_3$H; —C(=O)R$^{20}$; or, when $R^{13}$ is —CH(Z$^2$) (R$^{12}$) and $Z^2$ is —N(R$^{19}$)R$^{16}$, $R^{19}$ may comprise a moiety bonded to $R^{16}$ to form a heterocyclic ring; and
  (c) $R^{20}$ is $R^{12}$, NH(R$^{12}$), N(R$^{12}$) (R$^{21}$), O(R$^{21}$), or S(R$^{21}$) (preferably $R^{12}$, NH(R$^{12}$), N(R$^{12}$) (R$^{21}$)); where $R^{21}$ is alkyl, alkenyl, a carbocyclic ring, a heterocyclic ring, or (preferably) when $R^{20}$ is N(R$^{12}$) (R$^{21}$) $R^{21}$ may be a moiety bonded to $R^{12}$ to form a heterocyclic ring; and
(8) $R^{16}$ is $R^{24}$ or hydrogen; where $R^{24}$ is alkyl; alkenyl; arylalkyl; heteroalkyl; heteroalkenyl; heteroarylalkyl; a carbocyclic ring; a heterocyclic ring; or, when $Z^1$ is N(R$^{19}$)R$^{16}$ and $R^{16}$ is $R^{24}$, $R^{16}$ and $R^{19}$ may together comprise a heterocyclic ring including the nitrogen atom to which $R^{19}$ is bonded (preferably hydrogen, alkyl, a carbocyclic ring or a heterocyclic ring);

(B) $R^2$ is hydrogen, halogen, alkoxy, or $R^{22}$C(=O)N-H—(preferably hydrogen or alkoxy), where $R^{22}$ is hydrogen or alkyl (preferably hydrogen);

(C) bond "a" is a single bond or is nil; and bond "b" is a single bond, a double bond, or is nil; except bond "a" and bond "b" are not both nil;

(D) $R^3$ is —C(R$^{10a}$)—, or —CH$_2$—R$^{23}$— (preferably —C(R$^{10a}$)—); where $R^{23}$ is —C(R$^{10a}$), —O—, or —N—, and $R^{23}$ is directly bonded to N' in Formula (I) to form a 5-membered ring; except, if bond "a" is nil, then $R^3$ is (1) (preferably) —C(R$^{10a}$) (Z$^3$)—, where
  (i) $Z^3$ is —R$^{16}$, —OR$^{25}$, —S(O)$_r$R$^{25}$—, where r is an integer from 0 to 2 (preferably 0), —OC(=O)R$^{25}$, or —N(R$^{25}$)R$^{26}$;
  (ii) $R^{25}$ and $R^{26}$ are, independently, alkyl, alkenyl, carbocyclic ring or heterocyclic ring substituents; or $R^{25}$ and $R^{26}$ together comprise a heterocyclic ring including the nitrogen atom to which $R^{25}$ and $R^{26}$ are bonded; or
(2) —CH$_2$—R$^{27}$—; where $R^{27}$ is —C(R$^{10a}$) (R$^{24}$), —O—, or —NR$^{10}$, and $R^{27}$ is directly bonded to N'' in Formula (II) to form a 5-membered ring;

(E)
(1) if bond "b" is a single bond, $R^4$ is (preferably) —CH(R$^{28}$)—; or, if bond "a" is nil; —C(O)N-HSO$_2$—; or —C*(R$^{28}$)—; if $R^5$ contains a R— moiety; where $R^{28}$ is hydrogen or (preferably) COOH, and C* is linked to R— to form a 3-membered ring;
(2) if bond "b" is a double bond, $R^4$ is —C(R$^{28}$)=; or
(3) if bond "b" is nil, $R^4$ is hydrogen, —SO$_3$H, —PO(OR$^{29}$)OH, —C(O)NHSO$_2$N(R$^{29}$) (R$^{30}$), —OSO$_3$H, —CH(R$^{30}$)COOH, or —OCH (R$^{29}$)COOH (preferably —SO$_3$H or —C(O)N-HSO$_2$N(R$^{29}$) (R$^{30}$)); where $R^{29}$ is hydrogen, alkyl, alkenyl, a carbocyclic ring, or a heterocyclic ring; and $R^{30}$ is hydrogen, alkyl, alkenyl, or —NHR$^{10a}$; or (preferably), if $R^4$ is —C(O)N-HSO$_2$N(R$^{29}$) (R$^{30}$), $R^{29}$ and $R^{30}$ may together comprise a heterocyclic ring including the nitrogen to which $R^{29}$ and $R^{30}$ are bonded; and (F) (1) if bond "a" or bond "b" is nil, then $R^5$ is Y;
(2) if bond "a" and "b" are single bonds, $R^5$ is —X$^2$—C'''=C(R$^{10a}$)—R$^{31}$—Y—, or —X$^2$—C'''(R$^3$-$^2$)—R$^{31}$—Y—; or
(3) (preferably) if bond "a" is a single bond and bond "b" is a double bond, $R^5$ is —C(R$^{10a}$) (R$^{33}$)—X$^2$—C'''—R$^{31}$—Y—; or (preferably) —X$^1$—C(R$^{10a}$) (R$^{33}$)—C'''—R$^{31}$—Y—; or —X$^2$—C'''—R$^{31}$—Y—, where (a) $X^1$ is O or $C(R^{33})$, where $R^{33}$ is hydrogen, alkyl or alkoxy;

(b) $X^2$ is O; $S(O)_s$, where s is an integer from 0 to 2 (preferably 0); or $C(R^{33})$;

(c) $R^{31}$ is nil, alkyl, alkenyl, a carbocyclic ring, or a heterocyclic ring;

(d) $R^{32}$ is hydrogen; alkyl; alkenyl; —COOH; or, if $R^4$ is —C*($R^{28}$), $R^{32}$ may be linked to C* to form a 3-membered carbocyclic ring;

(e) Y is O or $Z^4$—$R^{34}$—O, where
  (1) $Z^4$ is —O—; —S(O)$_t$—, where t is an integer of 0 to 2 (preferably 0); or—$NR^{10a}$—; and
  (2) $R^{34}$ is alkyl, alkenyl, heteroalkyl, heteroalkenyl, a carbocyclic ring, or a heterocyclic ring (preferably alkyl or alkenyl); and
  (3) Y is directly bonded to C'

(f) C" is bonded to $R^4$ to form a 5- or 6-membered ring;

(G)
(1) $A^1$ is N or $C(R^{40})$; where $R^{40}$ is hydrogen, hydroxy, alkoxy, nitro, cyano, halogen, alkyl, or $N(R^{10})(R^{11})$ (preferably hydrogen or halogen), and (2) $A^2$ is N or (preferably) $C(R^6)$; where $R^6$ is hydrogen or halogen;

(3) $A^3$ is N or (preferably) $C(R^{41})$; where $R^{41}$ is hydrogen;

(4) $R^8$ is hydrogen, alkyl, a carbocyclic ring, a heterocyclic ring, alkoxy, hydroxy, alkenyl, arylalkyl, or $N(R^{10})(R^{11})$ (preferably hydrogen or a carbocyclic ring);

(5) $R^7$ is hydrogen, halogen, alkyl, a carbocyclic ring, or a heterocyclic ring (preferably a heterocyclic ring); and (7) $R^9$ is hydrogen, halogen, nitro, or $N(R^{10})(R^{11})$;

(H) except that
(1) when $A^1$ is $C(R^{40})$, $R^8$ and $R^{40}$ may together comprise a heterocyclic ring including N' and $A^1$;

(2) when $A^2$ is $C(R^6)$, $R^6$ and $R^7$ may together comprise —O—(CH$_2$)$_n$—O—, where n is an integer from 1 to 4; and (3) when $A^3$ is $C(R^{41})$, $R^8$ and $R^{41}$ may together comprise a heterocyclic ring including N" and the adjacent carbon to which $R^{41}$ is bonded;

and pharmaceutically-acceptable salts and biohydrolyzable esters thereof, and hydrates thereof.

Definitions and Usage of Terms:

The following is a list of definitions for terms used herein.

"Heteroatom" is a nitrogen, sulfur or oxygen atom. Groups containing one or more heteroatoms may contain different heteroatoms.

"Alkyl" is an unsubstituted or substituted saturated hydrocarbon chain radical having from 1 to 8 carbon atoms, preferably from 1 to 4 carbon atoms. Preferred alkyl groups include (for example) methyl, ethyl, propyl, isopropyl, and butyl.

"Heteroalkyl" is an unsubstituted or substituted saturated chain radical having from 3 to 8 members comprising carbon atoms and one or two heteroatoms.

"Alkenyl" is an unsubstituted or substituted hydrocarbon chain radical having from 2 to 8 carbon atoms, preferably from 2 to 4 carbon atoms, and having at least one olefinic double bond.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Cycloalkyl" is a saturated carbocyclic ring radical. Preferred cycloalkyl groups include (for example) cyclopropyl, cyclobutyl and cyclohexyl.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Aryl" is an aromatic carbocyclic ring radical. Preferred aryl groups include (for example) phenyl, tolyl, xylyl, cumenyl and naphthyl.

"Heteroaryl" is an aromatic heterocyclic ring radical. Preferred heteroaryl groups include (for example) thienyl, furyl, pyrrolyl, pyridinyl, pyrazinyl, thiazolyl, pyrimidinyl, quinolonyl, and tetrazolyl.

"Alkoxy" is an oxygen radical having a hydrocarbon chain substituent, where the hydrocarbon chain is an alkyl or alkenyl (i.e., —O—alkyl or —O—alkenyl). Preferred alkoxy groups include (for example) methoxy, ethoxy, propoxy and allyloxy.

"Alkylamino" is an amino radical having one or two alkyl substituents (i.e., —N—alkyl).

"Arylalkyl" is an alkyl radical substituted with an aryl group. Preferred arylalkyl groups include benzyl and phenylethyl.

"Arylamino" is an amine radical substituted with an aryl group (i.e., —NH—aryl).

"Aryloxy" is an oxygen radical having a aryl substituent (i.e., —O—aryl).

"Acyl" or "carbonyl" is a radical formed by removal of the hydroxy from an carboxylic acid (i.e., R—C(=O)—). Preferred alkylacyl groups include (for example) acetyl, formyl, and propionyl.

"Acyloxy" is an oxygen radical having an acyl substituent (i.e., —O—acyl); for example, —O—C(=O)—alkyl.

"Acylamino" is an amino radical having an acyl substituent (i.e., —N—acyl); for example, —NH—C(=O)—alkyl.

"Halo", "halogen", or "halide" is a chloro, bromo, fluoro or iodo atom radical. Chloro and fluoro are preferred halides.

Also, as referred to herein, a "lower" hydrocarbon moiety (e.g., "lower" alkyl) is a hydrocarbon chain comprised of from 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium). Preferred anionic salts include the halides (such as chloride salts).

A "biohydrolyzable ester" is an ester of a quinolonyl lactam ester that does not essentially interfere with the antimicrobial activity of the compounds, or that are readily metabolized by a human or lower animal subject to yield an antimicrobially-active quinolonyl lactam ester. Such esters include those that do not interfere with the biological activity of quinolone antimicrobials or beta-lactam antimicrobials (cephems, for example). Many such esters are known in the art, as described in World Patent Publication 87/05297, Johnston et al., published Sep. 11, 1987, (incorporated by reference herein). Such esters include lower alkyl esters, lower acyloxyalkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and alkyl acylamino alkyl esters ( such as acetamidomethyl esters ).

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

Also, as used in defining the structure of the compounds of this invention, a particular radical may be defined for use as a substituent in multiple locations. For example, the $R^{10a}$ substituent is defined as a potential substituent of $R^1$, but is also incorporated into the definition of other substituents (such as $R^3$, $R^8$, and $R^9$). As used herein, such a radical is independently selected each time it is used (e.g., $R^{10a}$ need not be alkyl in all occurrences in defining a given compound of this invention).

Lactam-containing moieties:

Groups $R^3$, $R^4$, and $R^5$, together with bonds "a" and "b", form any of a variety of lactam-containing moieties known in the art to have antimicrobial activity. Such moieties wherein either bond "a" or bond "b" are nil (i.e., do not exist) are monocyclic; if both bonds exist, the structures are bicyclic.

Preferred lactam moieties include the oxacephems and carbacephems of the representative formula:

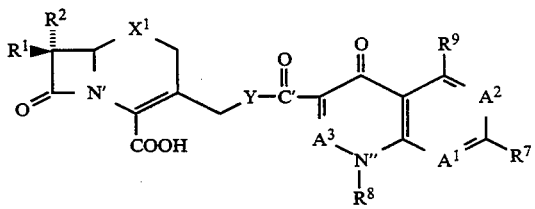

wherein bond "a" is a single bond; bond "b" is a double bond; $R^3$ is —C($R^{10a}$)—, where $R^{10a}$ is hydrogen; $R^4$ is —CH($R^{28}$), where $R^{28}$ is COOH; and $R^5$ is —$X^1$—C($R^{10a}$) ($R^{33}$)—C'''$R^{31}$—Y—, where $R^{10a}$ and $R^{33}$ are hydrogen, $R^{31}$ is methylene, and $X^1$ is O (for oxacephems) or C($R^{33}$) (for carbacephems).

Other preferred lactam moieties include the isocephems and iso-oxacephems of the representative formula:

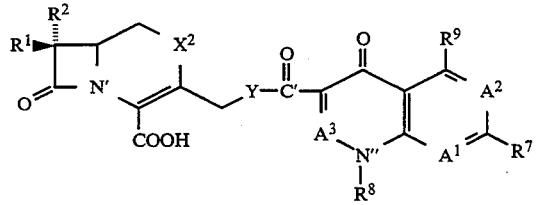

wherein bond "a" is a single bond; bond "b" is a double bond; $R^3$ is —C($R^{10a}$ where $R^{10a}$ is hydrogen; $R^4$ is —C($R^{28}$), where $R^{28}$ is COOH; and $R^5$ is —C($R^{10a}$) ($R^{33}$)—$X^2$—C'''—$R^{31}$—Y—where $R^{10a}$ and $R^{33}$ are each hydrogen, $R^{31}$ is methylene, and $X^2$ is S (for isocephems) or O (for iso-oxacephems).

Other preferred lactam-containing moieties include the penems, carbapenems and clavems, of the representative formula:

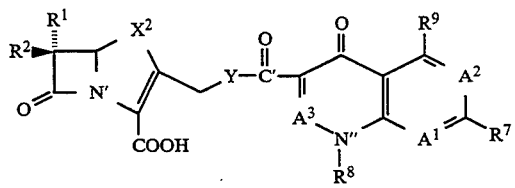

wherein bond "a" is a single bond; bond "b" is a double bond; $R^3$ is —C($R^{10a}$), where $R^{10a}$ is hydrogen; $R^4$ is —C($R^{28}$):, where $R^{28}$ is COOH; and $R^5$ is —$X^2$—C'''—$R^{31}$—Y—, where $R^{31}$ is methylene, and $X^2$ is S (for penems), C($R^{33}$) (for carbapenems), or O (for clavems). Such lactam moieties are described in the following articles, all incorporated by reference herein: R. Wise, "In Vitro and Pharmacokinetic Properties of the Carbapenems", 30 *Antimicrobial Agents and* Chemotherapy 343 (1986); and S. McCombie et al., "Synthesis and In Vitro Activity of the Penem Antibiotics", 8 *Medicinal Research Reviews* 393 (1988).

Other preferred lactam-containing moieties of this invention include the penicillins of the representative formula:

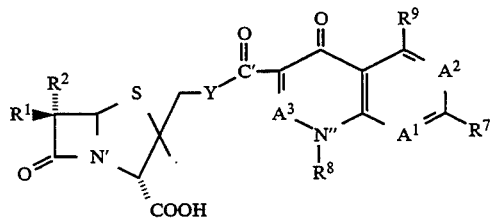

wherein bond "a" is a single bond, bond "b" is a single bond; $R^3$ is —C($R^{10a}$)—, where $R^{10a}$ is hydrogen; $R^4$ is —CH($R^{28}$)— where $R^{28}$ is COOH; and $R^5$ is —$X^2$—C'''($R^{32}$)—$R^{31}$—Y— where $R^{32}$ is methyl, $R^{31}$ is methylene, and $X^2$ is S.

Other preferred lactam-containing moieties include the monocyclic beta-lactams, of the representative formula:

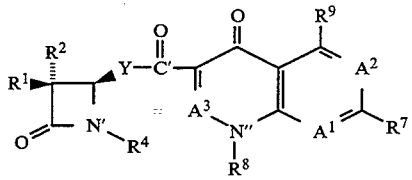

wherein bond "a" is a single bond; bond "b" is nil; $R^3$ is —C($R^{10a}$)—, where $R^{10a}$ is hydrogen; $R^5$ is Y; and $R^4$ is —$SO_3H$ (for a monobactam), —PO(O$R^{34}$)OH (for a monophospham); —C(O)NHSO$_2$N($R^{34}$) ($R^{35}$) (for a monocarbam), —OSO$_3$H (for a monosulfactam), —CH($R^{35}$)COOH (for nocardicins), or —OCH($R^{34}$)COOH. Such lactam moieties are described in C. Cimarusti et al., "Monocyclic 8-lactam Antibiotics", 4 *Medicinal Research Reviews* 1 (1984), incorporated by reference herein.

Other preferred lactam moieties include the monocyclic beta-lactams of the representative formula:

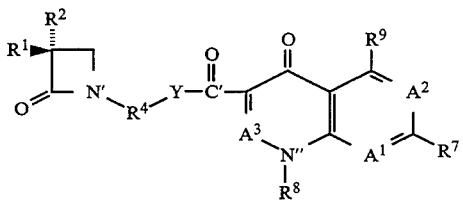

wherein bond "a" is nil, bond "b" is a single bond; $R^3$ is —C($R^{10a}$) ($R^{29}$)— where both $R^{10a}$ and $R^{29}$ are hydrogen; and $R^5$ is Y.

Other preferred lactam moieties include the clavams of the representative formula:

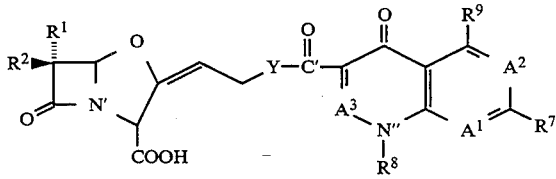

wherein bond "a" is a single bond; bond "b" is a single bond; $R^3$ is —C($R^{10a}$)—, where $R^{10a}$ is hydrogen; $R^4$ is —CH($R^{28}$)—, where $R^{28}$ is COOH; and $R^5$ is $X^2$—C'''=C—($R^{10a}$)—$R^{31}$—Y—, where $R^{10a}$ is hydrogen and $R^{31}$ is methylene, and $X^2$ is O.

Other preferred lactam moieties include the 2,3-methylenopenams and -carbapenams of the representative formula:

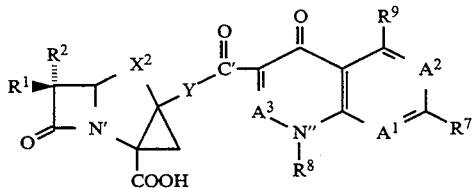

wherein bond "a" is a single bond; bond "b" is a single bond; $R^3$ is —C($R^{10a}$)—, where $R^{10a}$ is hydrogen; $R^4$ is —C*($R^{28}$), where $R^{28}$ is COOH; and $R^5$ is $X^2$—C'''—($R^{10a}$)—$R^{31}$—Y—, where $R^{31}$ is nil, $R^{32}$ is linked to C* to form a 3-membered carbocyclic ring, and $X^2$ is C($R^{33}$) or sulfur.

Lactam moieties of this invention also include the lactivicin analogs of the representative formula:

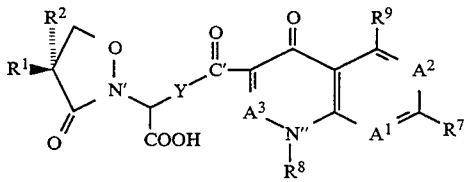

wherein bond "a" is nil; bond "b" is a single bond; $R^3$ is —CH$_2$—$R^{32}$, where $R^{32}$ is O; $R^4$ is —CH($R^{28}$)—, where $R^{28}$ is COOH; and $R^5$ is Y.

Other lactam moieties include the pyrazolidinones of the representative formula:

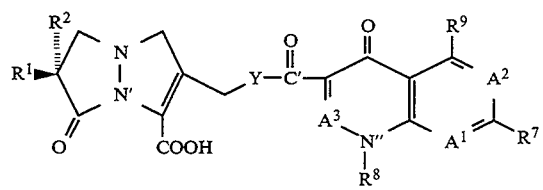

wherein bond "a" is a single bond; bond "b" is a double bond; $R^3$ is —CH$_2$—$R^{28}$—, where $R^{28}$ is —N—; $R^4$ is —C($R^{28}$)—, where $R^{28}$ is COOH; and $R^5$ is $X^2$—C'''—$R^{31}$—Y—, where $R^{31}$ is methylene, and $X^2$ is C($R^{33}$).

Other lactam moieties include the gamma-lactams of the representative formula:

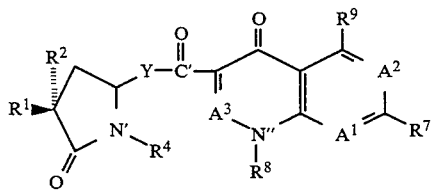

wherein bond "a" is a single bond; bond "b" is nil; $R^3$ is —CH$_2$—$R^{28}$—, where $R^{28}$ is —C($R^{10a}$) and $R^{10a}$ is hydrogen; $R^4$ is —SO$_3$H, —PO(O$R^{34}$)OH, —C(O)NHSO$_2$N($R^{34}$) ($R^{35}$), —OSO$_3$H, —CH($R^{35}$)COOH, or —OCH($R^{34}$)COOH; and $R^5$ is Y.

Preferred lactam-containing moieties include cephems, isocephems, iso-oxacephems, oxacephems, carbacephems, penicillins, penems, carbapenems, and monocyclic beta-lactams. Particularly preferred are cephems, penems, carbapenems and monocyclic beta-lactams.

$R^1$ is any radical that may be substituted at the active stereoisomeric position of the carbon adjacent to the lactam carbonyl of an antimicrobially-active lactam. (As used herein, the term "antimicrobially-active lactam" refers to a lactam-containing compound, without a quinolonyl substituent moiety, which has antimicrobial activity.) This "active" position is beta (i.e., 7-beta) for cephems, oxacephems and carbacephems (for example). The active position is alpha for penems, carbapenems, clavems and clavams.

Appropriate $R^1$ groups will be apparent to one of ordinary skill in the art. Many such $R^1$ groups are known in the art, as described in the following documents (all of which are incorporated by reference herein): *Cephalosporins and Penicillins: Chemistry and Biology* (E. Flynn, editor, 1972); *Chemistry and Biology of b-Lactam Antibiotics* (R. Morin et al., editors, 1987); "The Cephalosporin Antibiotics: Seminar-in-Print", 34 Drugs (Supp. 2) 1 (J. Williams, editor, 1987); *New Beta-Lactam Antibiotics: A Review from Chemistry of Clinical Efficacy of the New Cephalosporins* (H. Neu, editor, 1982); M. Sassiver et al., in *Structure Activity Relationships among the Semi-synthetic Antibiotics* (D. Perlman, editor, 1977. W. Durckheimer et al., "Recent Developments in the Field of Beta-Lactam Antibiotics", 24 *Angew. Chem. Int. Ed. Engl.* 180 (1985); G. Rolinson, "Beta-Lactam Antibiotics", 17 *J. Antimicrobial Chemotherapy* 5 (1986); European Patent Publication 187,456, Jung, published Jul. 16, 1986; and World Patent Publication 87/05297, Johnston et al., published Sep. 11, 1987.

For penems, carbapenems, clavems and clavams, $R^1$ is preferably lower alkyl, or hydroxy-substituted lower alkyl. Particularly preferred $R^1$ groups include hydrogen, hydroxymethyl, ethyl, [1(R)-hydroxyethyl], [1(R)-[(hydroxysulfonyl)oxyethyl]], and [1-methyl-1-hydroxyethyl]. Except for penems, carbapenems, clavems and clavams, preferred $R^1$ groups are amides, such as: acetylamino, preferably substituted with aryl, heteroaryl, aryloxy, heteroarylthio and lower alkylthio substituents; arylglycylamino, preferably N-substituted with heteroaryl carbonyl and cycloheteroalkylcarbonyl substituents; arylcarbonylamino; heteroarylcarbonylamino; and lower alkoxyiminoacetylamino, preferably substituted with aryl and heteroaryl substituents. Particularly preferred $R^1$ groups include amides of the general formula $R^{13}$—(CH$_2$)$_m$—C(=O)NH— and $R^{13}$ is $R^{12}$. Examples of such preferred $R^1$ groups include:
[(2-amino-5-halo-4-thiazolyl) acetyl]amino;
[(4-aminopyridin-2-yl)acetyl]amino;
[[(3,5-dichloro-4-oxo-1(4H)-pyridinyl)acetyl]amino];
[[[2- (aminomethyl) phenyl]acetyl]amino ];
[(1H-tetrazol-1-ylacetyl)amino];
[(cyanoacetyl)amino];
[(2-thienylacetyl)amino];
[[(2-amino-4-thiazoyl)acetyl]amino]; and
sydnone, 3-[-2-amino]-2-oxoethyl.

The following are other such preferred $R^1$ groups.

HCONH—

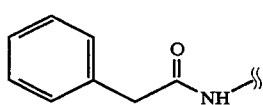

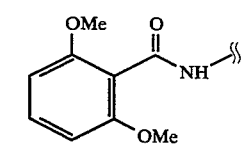

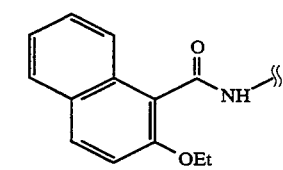

-continued

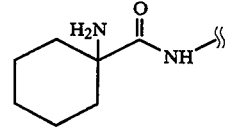

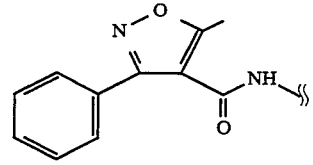

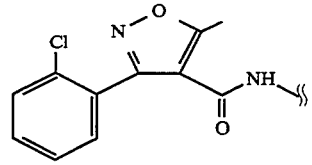

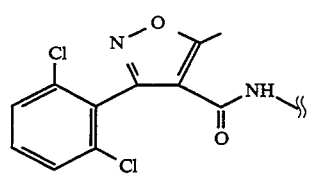

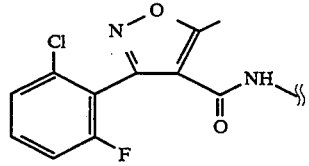

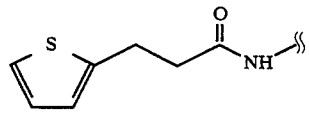

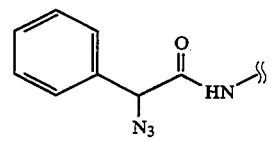

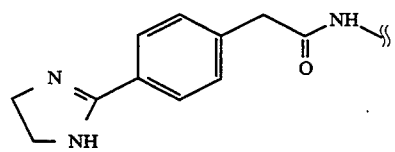

When $R^1$ is $R^{13}$—(CH$_2$)$_m$—C(C=O)NH—, and $R^{13}$ is —$Z^1$, preferred $R^1$ groups include the following:
[sulfamoylphenylacetyl]amino;
[[(4-pyridinylthio)acetyl]amino];
[[[(cyanomethyl)thio]acetyl]amino];
(S)-[[[(2-amino-2-carboxyethyl)thio]acetyl]amino];
[[[(trifluoromethyl)thio]acetyl]amino]; and
(E)-[[[(2-aminocarbonyl-2-fluoroethenyl)thio]acetyl]amino].

The following are other such preferred $R^1$ groups.

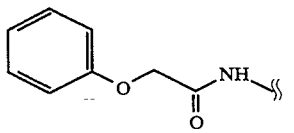
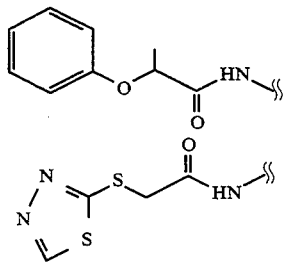
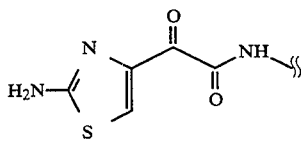
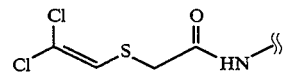
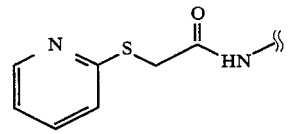
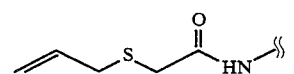
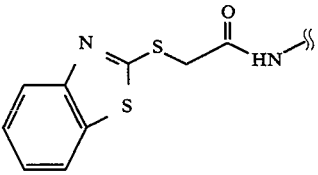
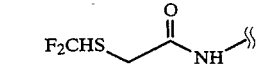
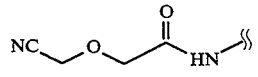

When $R^1$ is $R^{13}$—$(CH_2)_m$—$C(=O)NH$—, and $R^{13}$ is —$CH(Z^2)$ ($R^{12}$), preferred $R^1$ groups include the following:

[carboxyphenylacetyl]amino;
[(phenoxycarbonyl)phenylacetyl]amino;
[4-methyl-2,3-dioxo-1-piperazinecarbonyl-D-phenylglycyl]amino;
[[[3-(2-furylmethyleneamino)-2-oxo-1-imidazolidinyl-]-carbonyl]amino]phenyl]acetyl]amino;
(R)-[(aminophenylacetyl)amino];
(R)-[[amino(4-hydroxyphenyl)acetyl)amino];
(R)-[(amino-1,4-cyclohexadien-1-ylacetyl)amino];
[(hydroxyphenylacetyl)amino];
(R)-[[[[(4-ethyl-2,3-dioxo-1-piperazinyl)carbonyl]-amino]-(4-hydroxyphenyl)acetyl]amino);

(R)-[[[[(5-carboxy-1H-imidazol-4-yl)carbonyl]amino]-phenyl-acetyl]amino];
(R)-[[[[(4-hydroxy-6-methyl-3-pyridinyl)carbonyl-]amino](4-hydroxyphenyl)acetyl]amino];
(R)-[(phenylsulfoacetyl)amino];
(2R,3S)-[[2-[[(4-ethyl-2,3-dioxo-1-piperazinyl)carbonyl]-amino]-3-hydroxy-1-oxobutyl]amino];
[[carboxy(4-hydroxyphenyl)acetyl)amino);
(R)-[[amino[3-[(ethylsulfonyl)amino]phenyl]acetyl-]amino];
(R)-[[amino(benzo[b]thien-3-yl)acetyl)amino];
(R)-[[amino(2-naphthyl)acetyl]amino];
(R)-[[amino(2-amino-4-thiazolyl)acetyl]amino];
[[[[(6,7-dihydroxy-4-oxo-4H-1-benzopyran-3-yl)carbonyl]-amino](4-hydroxyphenyl)acetyl]amino];
(R,R)-[[2-[4-[2-amino-2-carboxyethyloxycarbonyl-]aminophenyl]-2-hydroxyacetyl]amino]; and
(S)-[[(5-hydroxy-4-oxo-1(4H)-pyridin-2-yl)carbonylamino(2-amino- 4-thiazolyl)acetyl)amino].

The following are other such preferred $R^1$ groups.

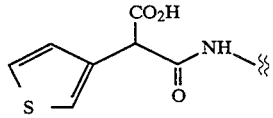
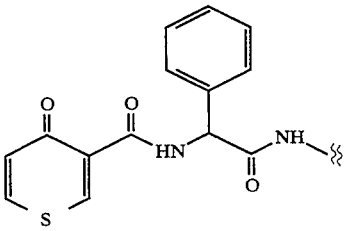
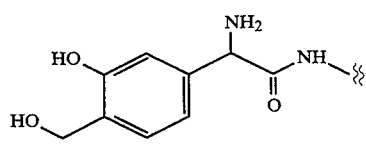
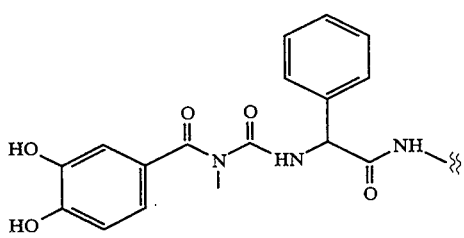
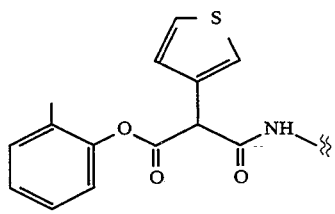

17
-continued
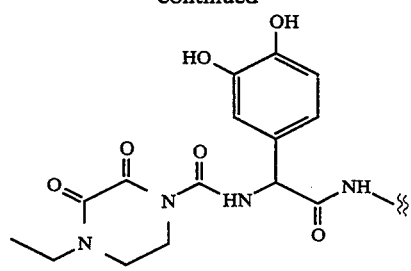
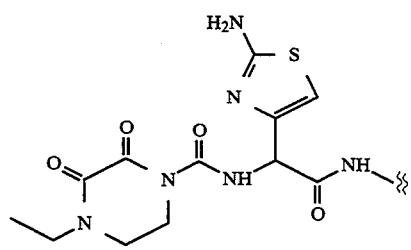
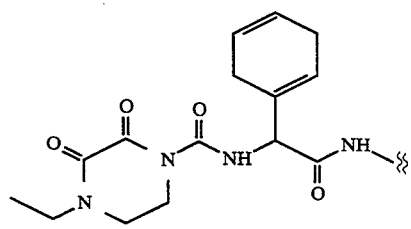
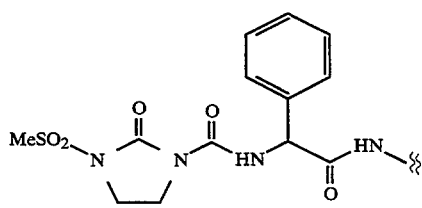
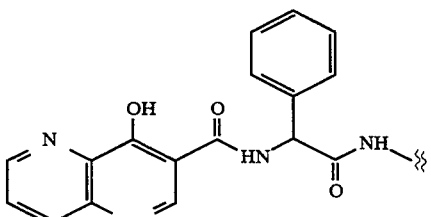
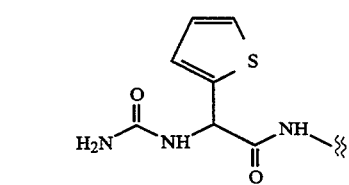
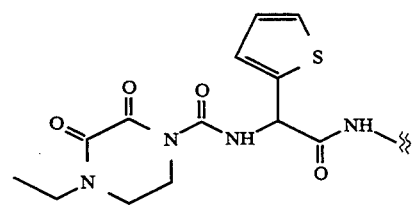
18
-continued
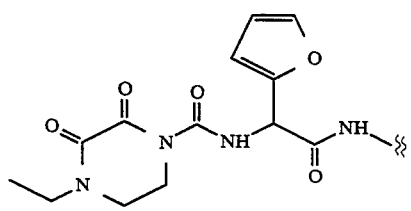
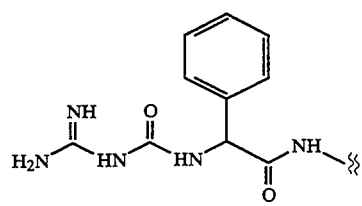
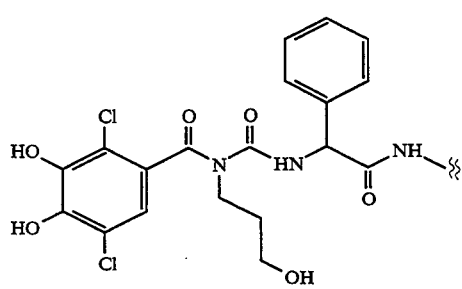
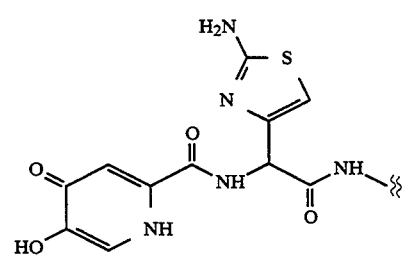
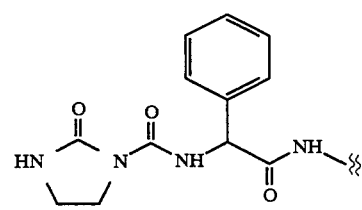
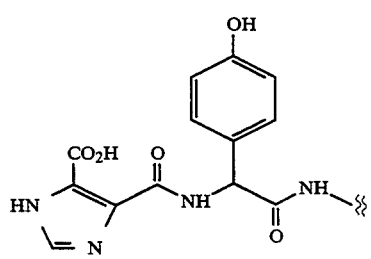

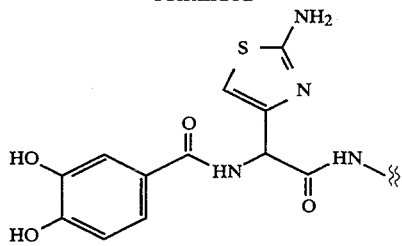

Another preferred R¹ group is R¹²—C(=CHR¹⁵)—C(=O)NH—. Such groups include (for example) the following structures.

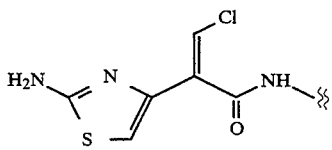

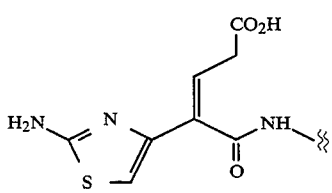

Another class of preferred R¹ groups (for lactam-containing moieties other than penems, carbapenems, clavems and clavams) include those of the formula:

R¹²—C(=NO—R¹⁴)—C(=O)NH—.

Examples of this preferred class of R¹ groups include:
2-phenyl-2-hydroxyiminoacetyl;
2-thienyl-2-methoxyiminoacetyl; and
2-[4-(gamma-D-glutamyloxy)phenyl]-2-hydroxyiminoacetyl.
(Z)[[(2-amino-4-thiazolyl)(methoxyimino)acetyl]amino];
[[(2-furanyl(methoxyimino)acetyl]amino];
(Z)-[[(2-amino-4-thiazolyl)[(1-carboxy-1-methyl)ethoxyimino]amino];
(Z)-[[(2-amino-4-thiazolyl) (1-carboxymethoxyimino)acetyl]amino];
[[(2-amino-4-thiazolyl)[(1H-imidazol-4-ylmethoxy)imino]acetyl]amino];
(Z) -[[(2-amino-4-thiazolyl-3-oxide) (methoxyimino)acetyl]; and
(S,Z) -[[(2-amino-4-thiazolyl)[carboxy(3,4-dihydroxyphenyl)methoxyimino]acetyl]amino].

Other preferred R¹ groups include the following structures.

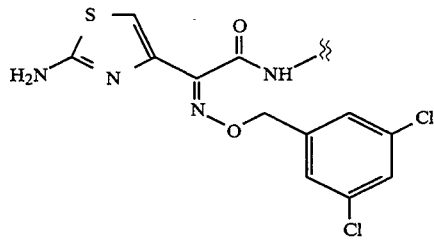

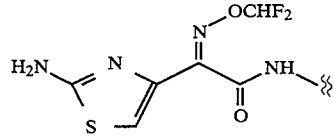

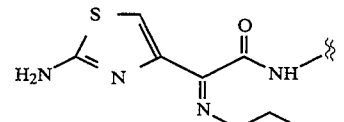

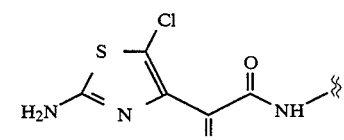

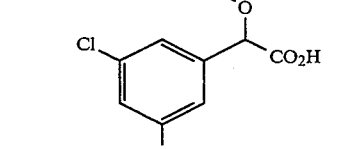

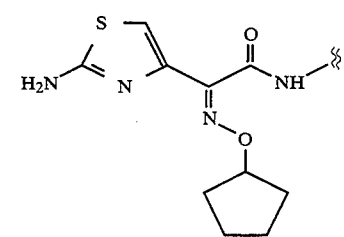

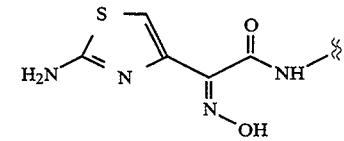

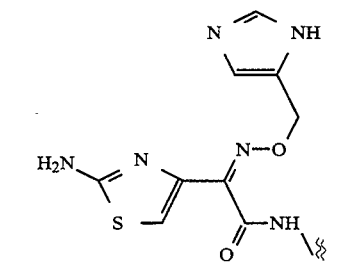

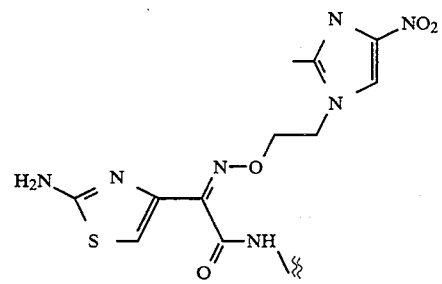

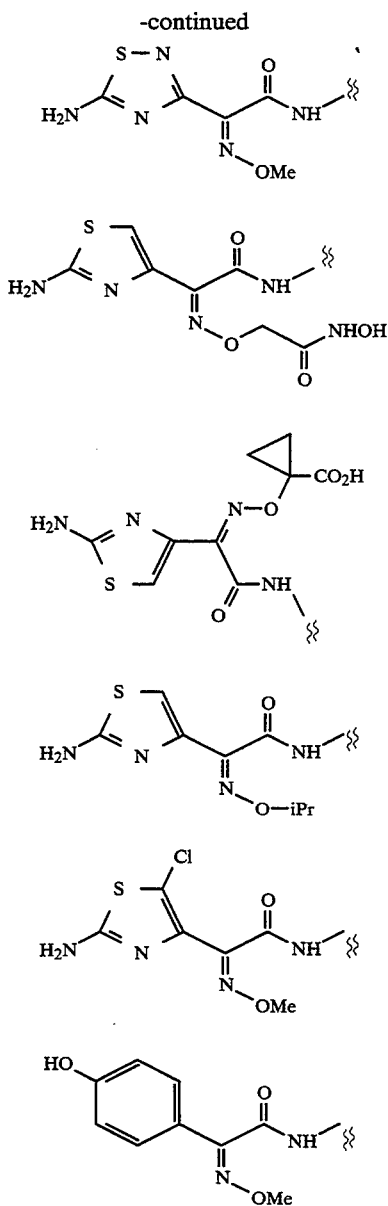

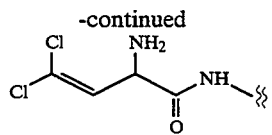

Suitable R² groups are among those well-known in the art, including those defined in the following documents (all incorporated by reference herein). W. Durckheimer et al., "Recent Developments in the Field of Beta-Lactam Antibiotics", 24 *Angew. Chem. Int. Ed. Engl.* 180 (985); G. Rolinson, "Beta-Lactam Antibiotics", 17 *J. Antimicrobial Chemotherapy* 5 (1986); and European Patent Publication 187,456, Jung, published Jul. 16, 1986. Preferred R² groups include hydrogen, methoxy, ethoxy, propoxy, thiomethyl, halogen, cyano, formyl and formylamino. Particularly preferred R² groups include hydrogen, methoxy, halogen, and formylamino.

Quinolone Moieties:

Groups $A^1$, $A^2$, $A^3$, $R^8$, $R^7$, and $R^9$ form any of a variety of quinolone, naphthyridine or related heterocyclic moieties known in the art to have antimicrobial activity. Such moieties are well known in the art, as described in the following articles, all incorporated by reference herein: J. Wolfson et al., "The Fluoroquinolones: Structures, Mechanisms of Action and Resistance, and Spectra of Activity In Vitro", 28 *Antimicrobial Agents and Chemotherapy* 581 (1985); and T. Rosen et al., 31 *J. Med Chem.* 1586 (1988); T. Rosen et al., 31 *J. Med. Chem.* 1598 (1988); G. Klopman et al., 31 *Antimicrob. Agents Chemother.* 1831 (1987); 31:1831–1840; J. P. Sanchez et al., 31 *J. Med. Chem.* 983 (1988); J. M. Domagala et al., 31 *J. Med. Chem.* 991 (1988); M. P. Wentland et al., in 20 *Ann. Rep. Med. Chem.* 145 (D. M. Baily, editor, 1986); J. B. Cornett et al., in 21 *Ann. Rep. Med. Chem.* 139 (D. M. Bailey, editor, 1986); P. B. Fernandes et al., in 22 *Ann. Rep. Med. Chem.* 117 (D. M. Bailey, editor, 1987); R. Albrecht, 21 *Prog. Drug Research* 9 (1977); and P. B. Fernandes et al., in 23 *Ann. Rep. Med. Chem. (R. C. Allen, editor,* 1987).

Preferred quinolone moieties include those where $A^1$ is $C(R^{40})$, $A^2$ is $C(R^6)$, and $A^3$ is $C(R^{41})$ (i.e., quinolones); $A^1$ is nitrogen, $A^2$ is $C(R^6)$, and $A^3$ is $C(R^{41})$ (i.e., naphthyridines); $A^1$ is $C(R^{40})$, $A^2$ is $C(R^6)$, and $A^3$ is nitrogen (i.e., cinnoline acid derivatives); and where $A^1$ is nitrogen, $A^2$ is nitrogen, and $A^3$ is $C(R^{41})$ (i.e., pyridopyrimidine derivatives). More preferred quinolone moieties are those where $A^1$ is $C(R^{40})$, $A^2$ is $C(R^6)$, and $A^3$ is $C(R^{41})$ (i.e., quinolones); and where $A^1$ is nitrogen, $A^2$ is $C(R^6)$, and $A^3$ is $C(R^{41})$ (i.e., naphthyridines). Particularly preferred quinolone moieties are where $A^1$ is $C(R^{40})$, $A^2$ is $C(R^6)$, and $A^3$ is $C(R^{41})$ (i.e., quinolones).

$R^8$ is preferably alkyl, aryl, cycloalkyl and alkylamino. More preferably, $R^8$ is ethyl, 2-fluoroethyl, 2-hydroxyethyl, t-butyl, 4-fluorophenyl, 2,4-difluorophenyl, methylamino and cyclopropyl. Cyclopropyl is a particularly preferred $R^8$ group. Preferred quinolone moieties also include those where $A^1$ is $C(R^{40})$ and $R^8$ and $R^{40}$ together comprise a 6-membered heterocyclic ring containing an oxygen or sulfur atom.

$R^6$ is preferably hydrogen or halo. More preferably $R^6$ is chlorine or fluorine. Fluorine is a particularly preferred $R^6$ group.

Preferred $R^7$ groups include nitrogen-containing heterocyclic rings. Particularly preferred are nitrogen-con- The following are other preferred R¹ groups.

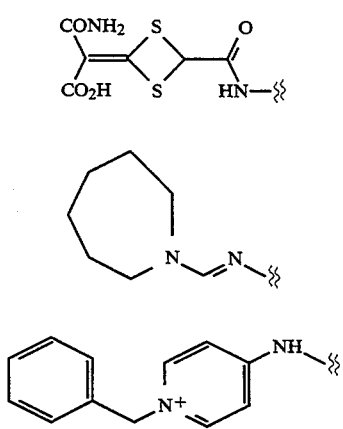

taining heterocyclic rings having from 5 to 8 members. The heterocyclic ring may contain additional heteroatoms, such as oxygen, sulfur, or nitrogen, preferably nitrogen. Such heterocyclic groups are described in U.S. Pat. Nos. 4,599,334, Petersen et al., issued Jul. 8, 1986; and U.S. Pat. No. 4,670,444, Grohe et al., issued Jun. 2, 1987 (both incorporated by reference herein). Preferred $R^7$ groups include unsubstituted or substituted pyridine, piperidine, morpholine, diazabicyclo[3.1.1]heptane, diazabicyclo [2.2.1]heptane, diazabicyclo[3.2.1]octane, diazabicyclo[2.2.2]octane, thiazolidine, imidazolidine, pyrrole and thiamorpholine, as well as the following particularly preferred $R^7$ groups include piperazine, 3-methylpiperazine, 3-aminopyrrolidine, 3-aminomethylpyrrolidine, N,N-dimethylaminomethylpyrrolidine, N-methylaminomethylpyrrolidine, N-ethylaminomethylpyrrolidine, pyridine, N-methylpiperazine, and 3,5-dimethylpiperazine.

Preferred quinolonyl lactam esters include those having a 6-fluoroquinolone moiety or an 8-halo-6-fluoroquinolone moiety, of formula:

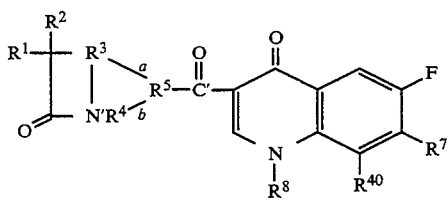

wherein $A^2$ is $C(R^6)$ and $R^6$ is F; $A^3$ is $C(R^{40})$; and $A^1$ is $C(R^{40})$ where $R^{40}$ is hydrogen, fluorine or chlorine. Preferred examples of such quinolone moieties include:
1-cyclopropyl-6-fluoro-,1,4-dihydro-4-oxo-7-(1-piperazinyl)-3-quinolinecarboxylic acid;
7-(3-aminopyrrolidinyl)-1-cyclopropyl-6-fluoro-1,4-dihydro-4-oxo-3-quinolinecarboxylic acid;
7-[(3-aminomethyl)pyrrolidinyl]-1-cyclopropyl-6-fluoro-1,4-dihydro-4-oxo-3-quinolinecarboxylic acid;
7-(3-aminopyrrolidinyl)-8-chloro-1-cyclopropyl-6-fluoro-1,4-dihydro-4-oxo-3-quinolinecarboxylic acid;
7- (3-aminopyrrolidinyl)-1-cyclopropyl-6,8-difluoro-1,4-dihydro-4-oxo-3-quinolinecarboxylic acid;
7-[(3-aminomethyl)pyrrolidinyl]-1-cyclopropyl-6,8-difluoro-4,1-dihydro-4-oxo-3-quinolinecarboxylic acid
6,8-difluoro-1-(2-fluoroethyl)-1,4-dihydro-7-(4-methyl-1-piperazinyl)-4-oxo-3-quinolinecarboxylic acid;
1-ethyl-6- fluoro-1,4-dihydro-4-oxo-7-(1-piperazinyl)-3-quinolinecarboxylic acid;
1-ethyl-6-fluoro-1,4-dihydro-7-(4-methyl-1-piperazinyl)-4-oxo-3-quinolinecarboxylic acid;
6-fluoro-1,4-dihydro-1-methylamino-7-(4-methyl-1-piperazinyl )-4-oxo-3-quinolinecarboxylic acid; and
1-cyclopropyl-7-[3-(dimethylaminomethyl)-1-pyrrolidinyl]-6,8-difluoro-1,4-dihydro-4-oxo-3-quinolinecarboxylic acid.

The following are other examples of such preferred quinolone moieties.

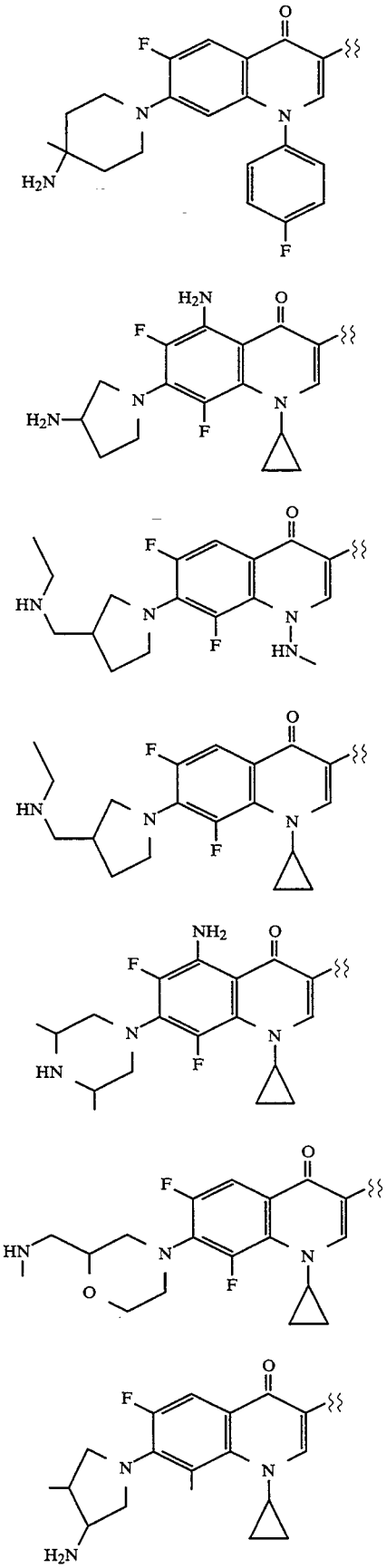

-continued
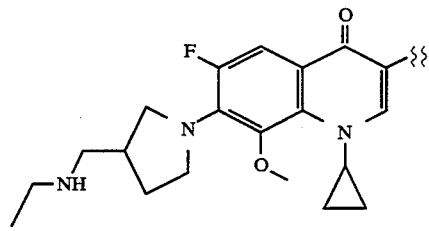
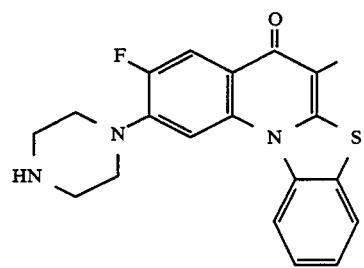
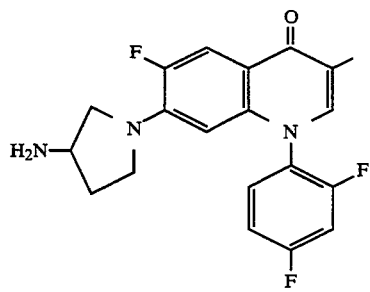
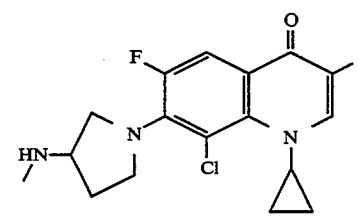
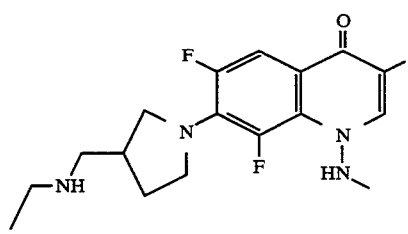
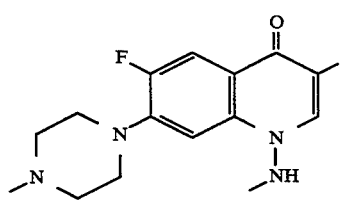
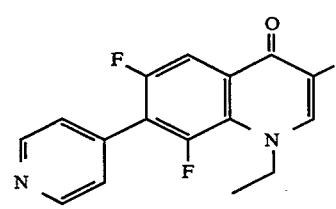
-continued
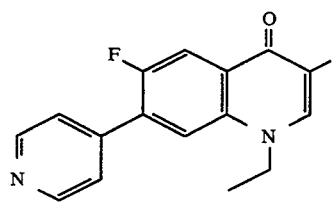
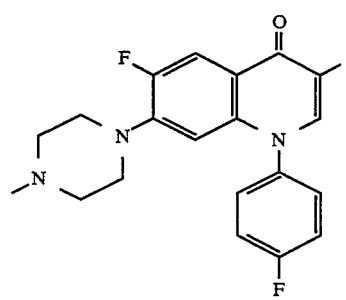
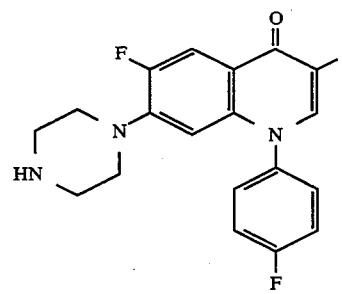
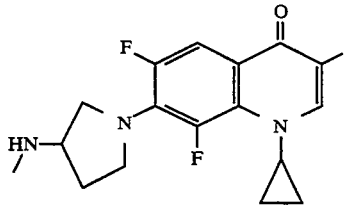
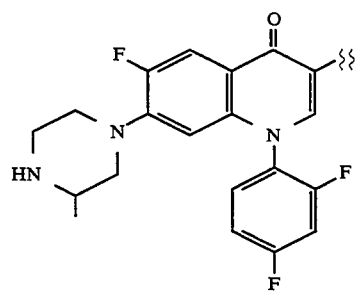
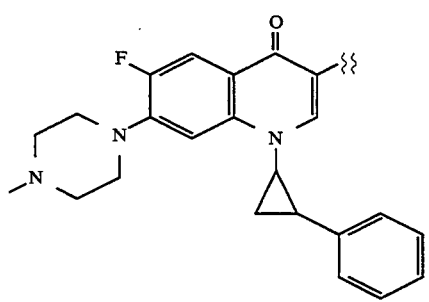

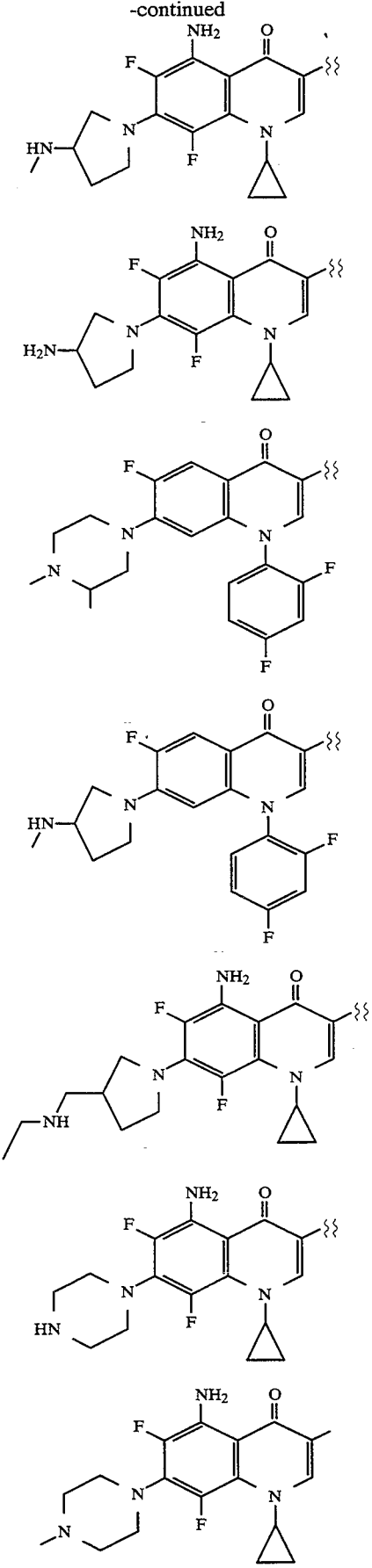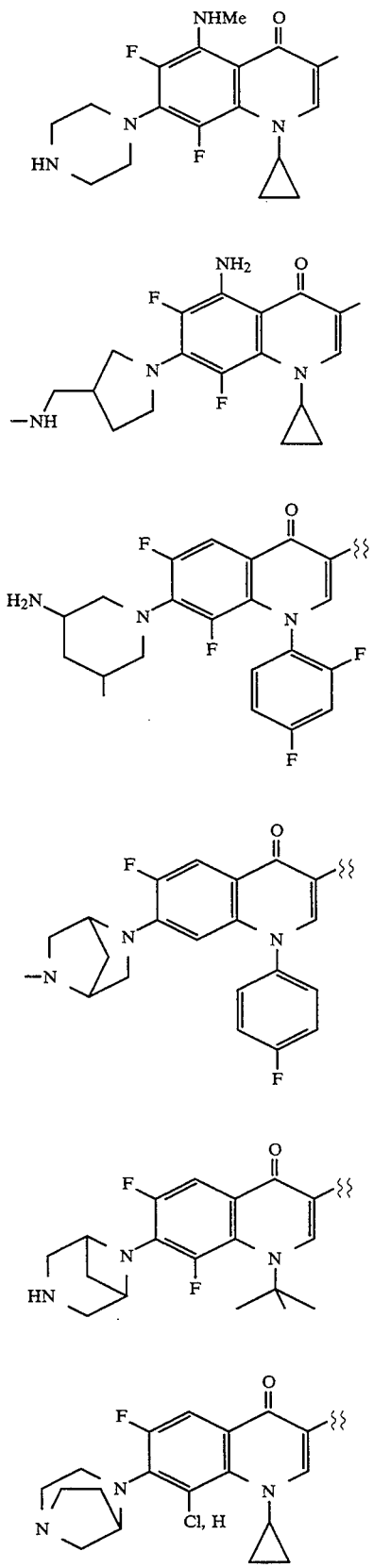

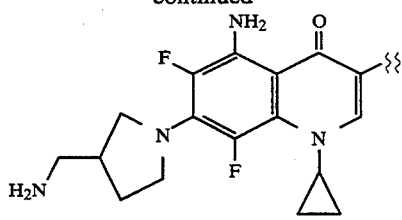

Also preferred are quinolonyl lactam esters having 1,8-naphthyridine moiety, of formula:

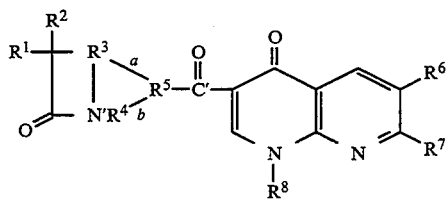

wherein $A^1$ is N; $A^2$ is $C(R^6)$ and $A^3$ is $C(R^{41})$. Preferred examples of such quinolone moieties include:

7-(3-aminopyrrolidinyl)-1-(2,4-difluorophenyl)-6-fluoro-1,4-dihydro-4-oxo-1,8-naphthyridine-3-carboxylic acid; and 1-ethyl-6-fluoro-1,4-dihydro-4-oxo-7-(1-piperazinyl)-1,8-naphthyridine-3-carboxylic acid.

The following are other examples of such preferred quinolone moieties.

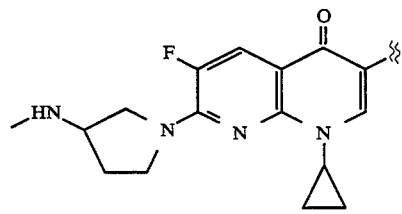

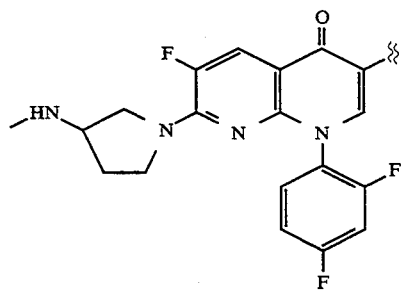

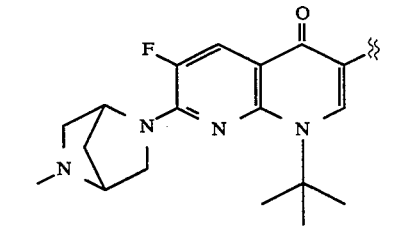

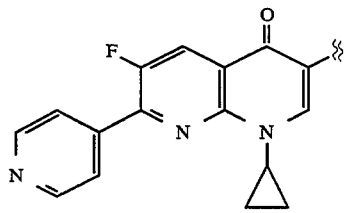

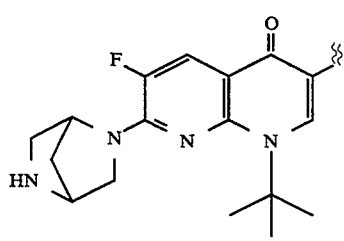

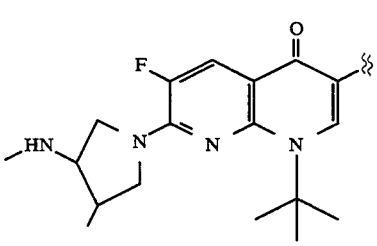

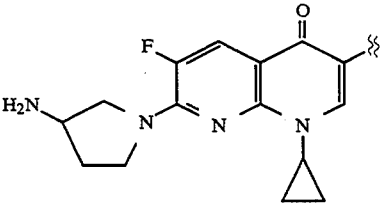

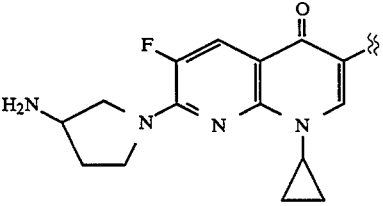

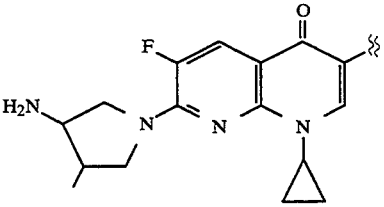

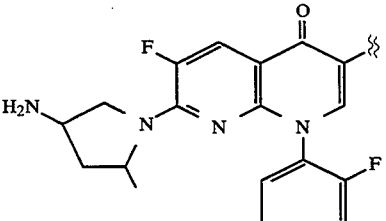

-continued

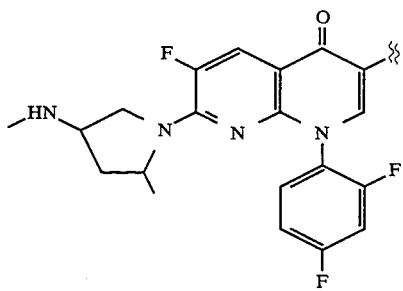

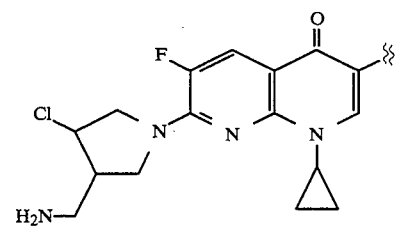

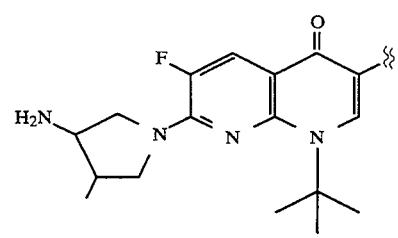

Also preferred are quinolonyl lactam esters having pyridobenzoxazine or pyridobenzthiazine moiety, of formula:

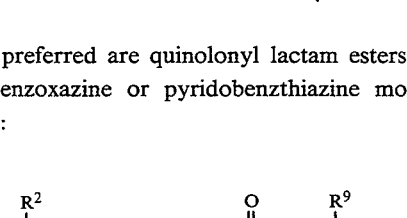

wherein $A^1$ is $C(R^{40})$; $A^2$ is $C(R^6)$; $A^3$ is $C(R^{41})$; and $R^{40}$ and $R^8$ together comprise a linking moiety between N' and A to form a 6-membered, oxygen-containing, heterocyclic ring where X (in this formula) is oxygen or sulfur. Preferred examples of such quinolone moieties include 9-fluoro-4,7-dihydro-3-methyl-10-(4-methyl-1-piperazinyl)-7-oxo-2H-pyrido[1,2,3-de]-1,4-benzoxazine-6-carboxylic acid; and the following structures.

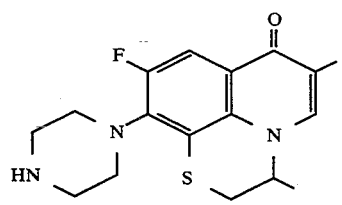

-continued

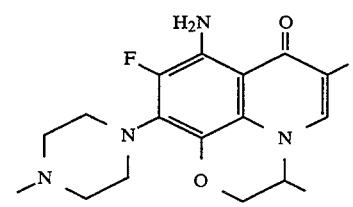

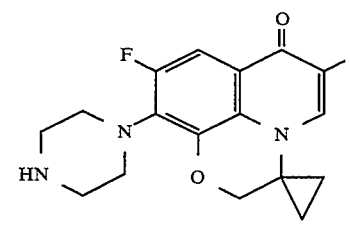

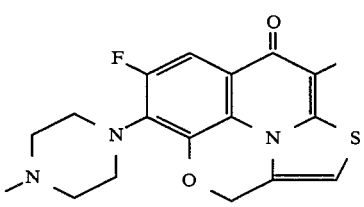

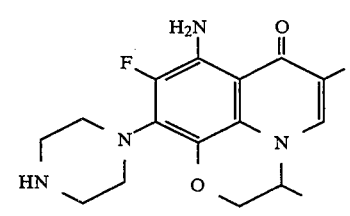

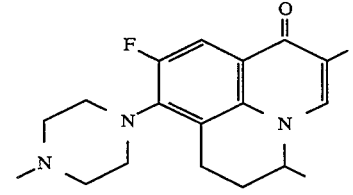

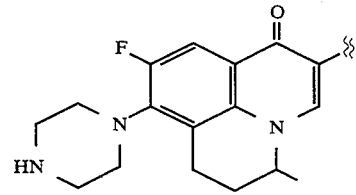

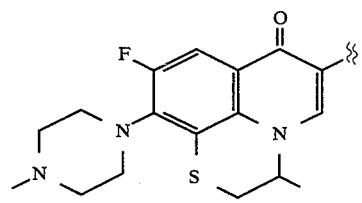

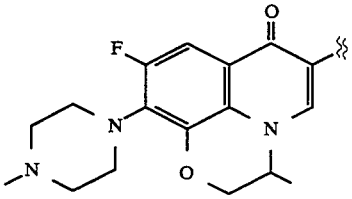

The specific physical, chemical, and pharmacological properties of the quinolonyl lactam esters of this invention may depend upon the particular combination of the integral lactam-containing moiety, quinolone moiety and linking moiety comprising the compound. For example, selection of particular integral moieties may affect the relative susceptibility of a quinolonyl lactam ester to bacterial resistance mechanisms (e.g., beta-lactamase activity).

Preferred quinolonyl lactam esters include compounds having the following specific combinations of lactam-containing moieties, quinolone moieties and linking moieties.

1) Ester-linked penem quinolones, such as compounds of the following classes.
  a) where—the lactam-containing moiety is a penem, wherein bond "a" is a single bond; bond "b" is a double bond; $R^3$ is —CH—; $R^4$ is —C(CO$_2$H)—; $R^5$ is —S—C'''—CH$_2$—O—; and
    the quinolone moiety is a structure, wherein $A_2$ is —CF—; $A^3$ is —CH—; and $R^7$ is a heterocyclic ring
  b) where—the lactam-containing moiety is a penem, wherein bond "a" is a single bond; bond "b" is a double bond; $R^1$ is (1-hydroxyethyl); $R^2$ is —H; $R^3$ is —CH—; $R^4$ is —C(CO$_2$H)—; $R^5$ is —S—C'''—CH$_2$—O—; and
    the quinolone moiety is a 6-fluoroquinolone moiety, wherein $A^1$ is —C($R^{39}$)—; $A^2$ is —CF—; $A^3$ is —CH—; and $R^7$ is a heterocyclic ring
  c) where—the lactam-containing moiety is a penem, wherein referring to the formula, wherein bond "a" is a single bond; bond "b" is a double bond; $R^3$ is —CH—; $R^4$ is —C(CO$_2$H)—; $R^5$ is —S—C'''—CH$_2$—O—;
    the quinolone moiety is a naphthyridinone, wherein $A^1$ is —N—; $A_2$ is —CF—; $A^3$ is —CH—; and $R^7$ is a heterocyclic ring
  d) where—the lactam-containing moiety is a penem, wherein bond "a" is a single bond; bond "b" is a double bond; $R^3$ is —CH—; $R^4$ is —C(CO$_2$H)—; $R^5$ is —S—C'''—CH$_2$—O—; and
    the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group Ester-linked penem quinolones of the classes (b), (c) and (d) are preferred; compounds of class (d) are particularly preferred.

3) Ester-linked penem quinolones, such as compounds of the following classes.
  a) where—the lactam-containing moiety is a penem, wherein bond "a" is a single bond; bond "b" is a double bond; $R^3$ is —CH—; $R^4$ is —C(CO$_2$H)—; $R^5$ is —S—C''''—S—CH$_2$CH$_2$—O—; and
    the quinolone moiety is a structure, wherein $A^2$ is —CF—; $A^3$ is —CH—; and $R^7$ is a heterocyclic ring
  b) where—the lactam-containing moiety is a penem, wherein bond "a" is a single bond; bond "b" is a double bond; $R^3$ is —CH—; $R^4$ is —C(CO$_2$H)—; $R^5$ is —S—C''''—S—CH$_2$CH$_2$—O—; and
    the quinolone moiety is a 6-fluoroquinolone moiety, wherein $A^1$ is —C($R^{39}$)—; $A^2$ is —CF—; $A^3$ is —CH—; and $R^7$ is a heterocyclic ring
  c) where—the lactam-containing moiety is a penem, wherein bond "a" is a single bond; bond "b" is a double bond; $R^3$ is —CH—; $R^4$ is —C(CO$_2$H)—; $R^5$ is —S—C''''—S—CH$_2$CH$_2$—O—; and
    the quinolone moiety is a naphthyridinone, wherein $A^1$ is —N—; $A^2$ is —CF—; $A^3$ is —CH—; and $R^7$ is a heterocyclic ring
  d) where—the lactam-containing moiety is a penem, wherein bond "a" is a single bond; bond "b" is a double bond; $R^1$ is (1-hydroxyethyl); $R^2$ is —H; $R^3$ is —CH—; $R^4$ is —C(CO$_2$H)—, and
    the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group Ester-linked penem quinolones of the classes (b), (c) and (d) are preferred; compounds of class (d) are particularly preferred.

4) Ester-linked carbapenem quinolones, such as compounds of the following classes.
  a) where—the lactam-containing moiety is a carbapenem, wherein bond "a" is a single bond; bond "b" is a double bond; $R^3$ is —CH—; $R^4$ is —C(CO$_2$H)—; $R^5$ is —CH($R^{33}$)—C'''—CH$_2$—O—; and
    the quinolone moiety is a structure, wherein $A^2$ is —CF—; $A^3$ is —CH—; and $R^7$ is a heterocyclic ring
  b) where—the lactam-containing moiety is a carbapenem, wherein bond "a" is a single bond; bond "b" is a double bond; $R^3$ is —CH—; $R^4$ is —C(CO$_2$H)—; $R^5$ is —CH($R^{33}$)—C'''—CH$_2$—O—; and
    the quinolone moiety is a 6-fluoroquinolone moiety, wherein $A^1$ is —C($R^{39}$)—; $A^2$ is —CF—; $A^3$ is —CH—; and $R^7$ is a heterocyclic ring
  c) where—the lactam-containing moiety is a carbapenem, wherein bond "a" is a single bond; bond "b" is a double bond; $R^3$ is —CH—; $R^4$ is —C(CO$_2$H)—; $R^5$ is —CH($R^{33}$)—C'''—CH$_2$—O—; and
    the quinolone moiety is a naphthyridinone, wherein $A^1$ is —N—; $A^3$ is —CF—; $A^3$ is —CH—; and $R^7$ is a heterocyclic ring
  d) where—the lactam-containing moiety is a carbapenem, wherein bond "a" is a single bond; bond "b" is a double bond; $R^1$ is (1-hydroxyethyl); $R^2$ is —H; $R^3$ is —CH—; $R^4$ is —C(CO$_2$H)—; $R^5$ is —CH($R^{33}$)—C'''—CH$_2$—O—; $R^{33}$ is —H or —Me; and
    —the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group Ester-linked carbapenem quinolones of the classes (b), (c) and (d) are preferred; compounds of class (d) are particularly preferred.

Ester-linked carbapenem quinolones, such as compounds of the following classes.

- a) where—the lactam-containing moiety is a carbapenem, wherein bond "a" is a single bond; bond "b" is a double bond; $R^3$ is —CH—; $R^4$ is —C(-$CO_2H$)—; $R^5$ is —CH($R^{33}$)—C'''—S—$CH_2CH_2$—O—; and
  the quinolone moiety is a structure, wherein $A^2$ is —CF—; $A^3$ is —CH—; and $R^7$ is a heterocyclic ring

- b) where—the lactam-containing moiety is a carbapenem, wherein bond "a" is a single bond; bond "b" is a double bond; $R^3$ is —CH—; $R^4$ is —C(-$CO_2H$)—; $R^5$ is —CH($R^{33}$)—C'''—S—$CH_2CH_2$—O—; and
  the quinolone moiety is a 6-fluoroquinolone moiety, wherein $A^1$ is —C($R^{39}$)—; $A^2$ is —CF—; $A^3$ is —CH—; and $R^1$ is a heterocyclic ring

- c) where—the lactam-containing moiety is a carbapenem, wherein bond "a" is a single bond; bond "b" is a double bond; $R^3$ is —CH—; $R^4$ is —C(-$CO_2H$)—; $R^5$ is —CH($R^{33}$)—C'''—S—$CH_2CH_2$—O—; and
  the quinolone moiety is a naphthyridinone, wherein $A^1$ is —N—; $A^3$ is —CF—; $A^3$ is —CH—; and $R^7$ is a heterocyclic ring

- d) where—the lactam-containing moiety is a carbapenem, wherein bond "a" is a single bond; bond "b" is a double bond; $R^1$ is (1-hydroxyethyl); $R^2$ is —H; $R^3$ is —CH—; $R^4$ is —C($CO_2H$)—; $R^5$ is —CH($R^{33}$)—C'''—S—$CH_2CH_2$—O—; $R^{33}$ is —H or —Me; and
  the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group.

Ester-linked penem quinolones of the classes (b), (c) and (d) are preferred; compounds of class (d) are particularly preferred.

6) Ester-linked oxacephem quinolones, such as compounds of the class where
  the lactam-containing moiety is a oxacephem, wherein bond "a" is a single bond; bond "b" is a double bond; $R^3$ is —CH—; $R^4$ is —C($CO_2H$)—;

$R^5$ is —O—$CH_2$—C'''—$CH_2$—O—;

the quinolone moiety is a structure, wherein $A^2$ is —CF—; $A^3$ is —CH—; and $R^7$ is a heterocyclic ring.

7) Ester-linked isocephem quinolones, such as compounds of the class where
  the lactam-containing moiety is a isocephem, wherein bond "a" is a single bond; bond "b" is a double bond; $R^3$ is —CH—; $R^4$ is —C($CO_2H$)—; $R^5$ is —$CH_2$—S—C'''—$CH_2$—O—; and
  the quinolone moiety is a structure, wherein $A^2$ is —CF—; $A^3$ is —CH—; and $R^7$ is a heterocyclic ring.

8) Ester-linked iso-oxacephem quinolones, such as compounds of the class where
  the lactam-containing moiety is a iso-oxacephem, wherein bond "a" is a single bond; bond "b" is a double bond; $R^3$ is —CH—; $R^4$ is —C($CO_2H$)—; $R^5$ is —$CH_2$—O—C'''—$CH_2$—O—; and
  the quinolone moiety is a structure, wherein $A^2$ is —CF—; $A^3$ is —CH—; and $R^7$ is a heterocyclic ring.

9) Ester-linked carbacephem quinolones, such as compounds of the class where
  the lactam-containing moiety is a carbacephem, wherein bond "a" is a single bond; bond "b" is a double bond; $R^3$ is —CH—; $R^4$ is —C($CO_2H$)—; $R^5$ is —$CH_2$—$CH_2$—C'''—$CH_2$—O—; and
  the quinolone moiety is a structure, wherein $A^2$ is —CF—; $A^3$ is —CH—; and $R^7$ is a heterocyclic ring.

10) Ester-linked monobactam quinolones, such as compounds of the following classes.
  - a) where—the lactam-containing moiety is a monobactam, wherein bond "a" is a single bond; bond "b" is nil; $R^3$ is —CH—and is bonded directly to X; $R^5$ is nil; X is —$CH_2O$—; and
    the quinolone moiety is a structure, wherein $A^2$ is —CF—; $A^3$ is —CH—; and $R^7$ is a heterocyclic ring
  - b) where—the lactam-containing moiety is a monobactam, wherein bond "a" is a single bond; bond "b" is nil; $R^3$ is —CH—and is bonded directly to X; $R^5$ is nil; X is —O—; and
    the quinolone moiety is a structure, wherein $A^2$ is —CF—; $A^3$ is —CH—; and $R^7$ is a heterocyclic ring Quinolonyl lactams esters of this invention include (for example) the following compounds.

[6R-(6α,7β)]]-7-[[[(Difluoromethyl)thio]acetyl]amino]-7-methoxy]-3-[[[1
-cyclopropyl-6-fluoro-1,4-dihydro-4-oxo-7-(1-piperazinyl)-
-3quinolinyl]carbonyloxy]methyl]-8-oxo-5-oxa-1-azabicyclo[4.2.0]oct-2-ene-2-carboxylic acid

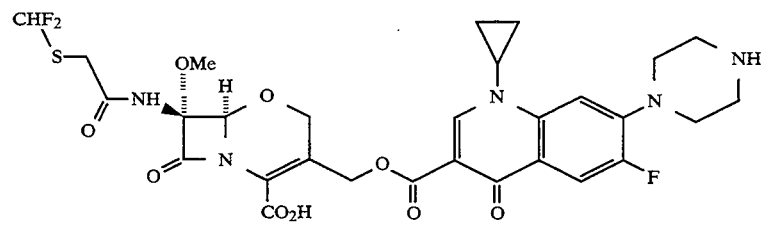

[6R-(6α,7β)]]-7-[[[(2-Aminocarbonyl-2-fluoroethenyl)-]amino]-3-[[[[9-fluoro-3,7-dihydro-3-methyl-10-(4-methyl -1-piperazinyl)-7-oxo-2H-pyrido[1,2,3 -de ]-

1,4-benzoxazin-6 -yl]carbonyl]oxy]methyl]-8-oxo-5-thia-1-azabicyclo[4.2.0]oct-2-carboxylic acid

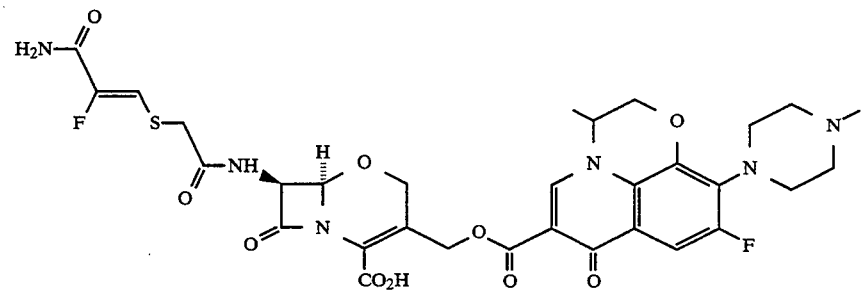

[6R-[6α, 7β]]-7-[[Carboxy(4-hydroxyphenyl)acetyl]amino]-3-[[[1-ethyl-6-fluoro-1,4-dihydro-7-(4-methyl-1-piperazinyl)-4-oxo-3-quinolinyl]carbonyloxy]methyl]-8-oxo-5-thia-1-azabicyclo[4.2.0]oct-2-ene-2-carboxylic acid

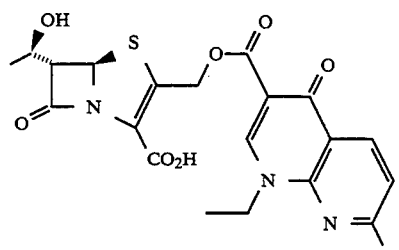

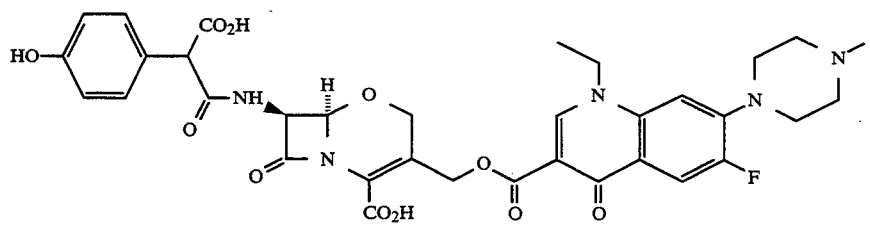

40

[5R-[5α,6α]]-3-[[[7-(3-Aminopyrrolidin-1-yl )-8-chloro-1-cyclopropyl-6-fluoro-1,4-dihydro-4-oxo-3-quinolinyl]carbonyloxy]methyl]-6-[(R)-1-hydroxyethyl]-7-oxo-4-thia-1-azabicyclo[3.2.0 ]hept-2-ene-2-carboxylic acid

[5R-[5α, 6α]]-3-[[[1-Cyclopropyl-6-fluoro-1,4-dihydro-4-oxo-7-(1-piperazinyl)-3-quinolinyl]carbonyloxy]methyl]-6-[(R)-1-hydroxyethyl]-7-oxo-4-thia-1-azabicyclo[3.2.0]oct -2-ene-2-carboxyl acid

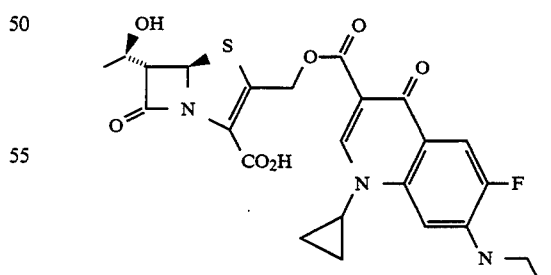

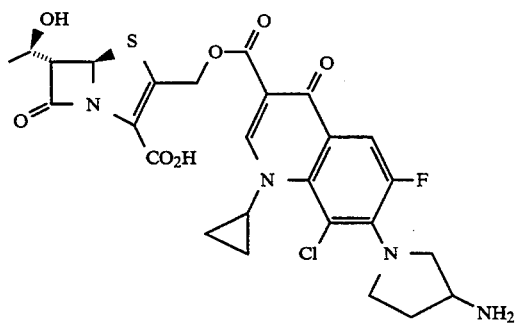

[5R-[5α, 6α]]-3-[[[1 -Ethyl-1,4-dihydro-6-methyl-4-oxo-1,8-naphthyridin-3-yl]carbonyloxy]methyl]-6-[(R)-1-hydroxyethyl]-7-oxo-4-thia-1-azabicyclo[3.2.0]hept-2-ene-2-carboxylic acid (3S )-2-[[1-Cyclopropyl-6-fluoro-1,4-dihydro-4-oxo-7-(1-piperazinyl)-3-quinolinyl]carbonyloxy]-3-[[[[[(R)-4-ethyl-2,3-dioxo-1-piperazinyl]carbonyl]amino](4-hydroxyphenyl)acetyl]amino]-4-oxo-1-azetidinesulfonic acid sodium salt

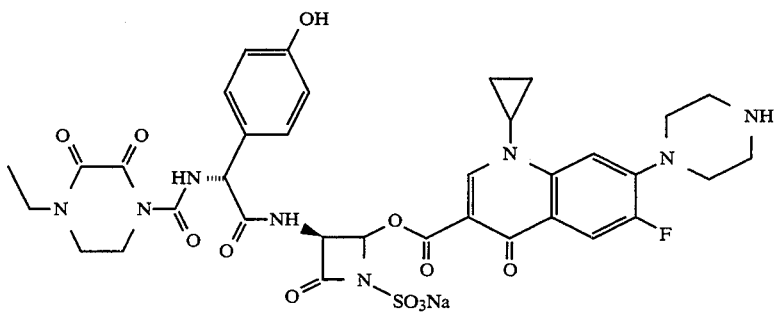

(3S)-3-[[(2-Amino-4-thiazolyl) (methoxyimino)acetylamino]-2-[[1-ethyl-6-fluoro-1,4-dihydro-4-oxo-7-(1-piperazinyl)-1,8-naphthyridin-3-yl]carbonyloxy]-4-oxo-1-azetidinesulfonic acid sodium salt

[6R-[6α,7β)]]-3-[[[7-(3-Amino-1-pyrrolidinyl)-1-(2,4-difluorophenyl)-6-fluoro-1,4-dihydro-4-oxo-1,8-naphthyridin-3-yl]carbonyl]methyl]-7-[[(5-hydroxy-4-oxo-1(4H)-pyridin-2-yl)carbonylamino](2-amino-4-thiazolyl)acetylamino]-8-oxo-1-azabicyclo [4.2.0]oct-2-ene-2-carboxylic acid

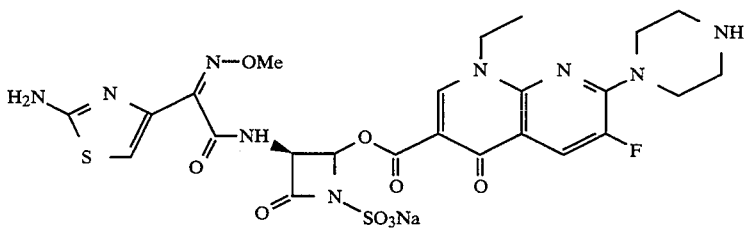

(3S)-2-[[5-Ethyl-5,8-dihydro-8-oxo-1,3-dioxolo[4,5-g]7-quinolinyl]carbonyloxy]-4-oxo-3-[(phenoxyacetyl)amino]azetidinesulfonic acid sodium salt

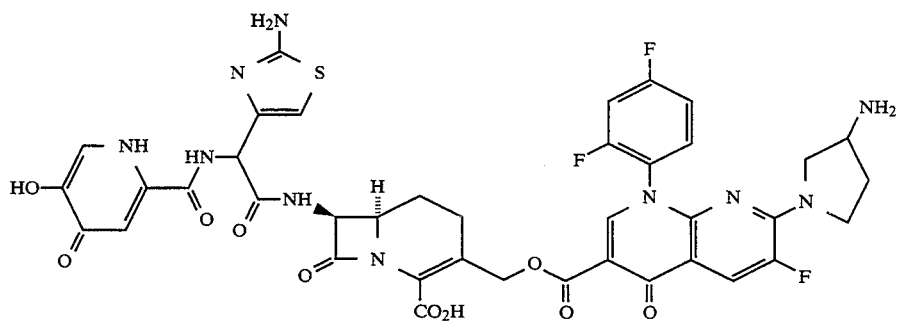

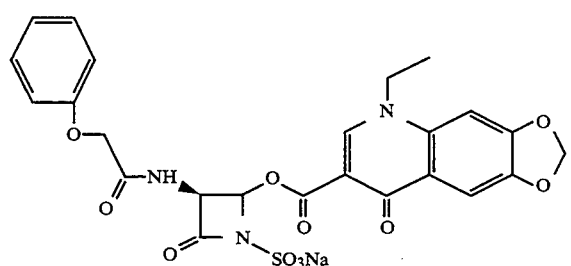

[6R-[6α,7β)]]-3-[[[7-(3-Amino-1-pyrrolidinyl)-8-chloro-1-cyclopropyl-6-fluoro-1,4-dihydro-4-oxo-3-quinolinyl]carbonyloxy]methyl]-7-[[[[(R)-4-ethyl-2,3-dioxo-1-piperazinyl]carbonyl]-amino](4-hydroxyphenyl)acetyl]amino ]-8-oxo-1-azabicyclo[4.2.0]oct-2-ene-2-carboxylic acid

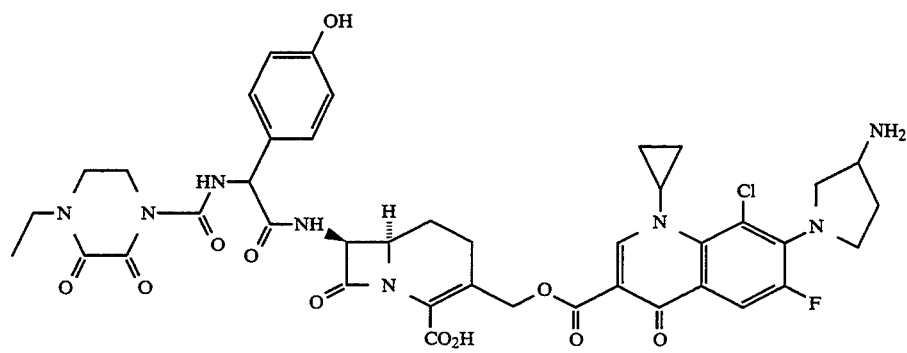

[6R-[6α,7β)]]-3-[[[]-Cyclopropyl-6-fluoro-1,4-dihydro-4-oxo-7-(1-piperazinyl)-3-quinolinyl]carbonyloxy]methyl]-7-[[phenoxy acetyl]amino]-8-oxo-1-azabicyclo[4.2.0]oct-2-ene-2-carboxylic acid

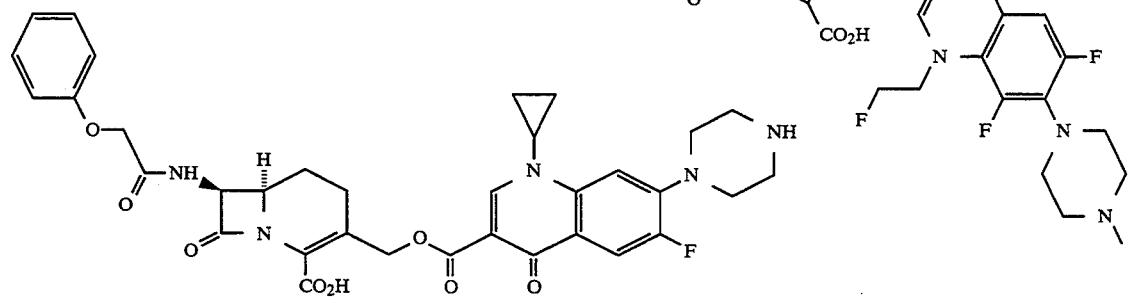

[5R,(5α,6α)]-3-[[[[7-[3-(Aminomethyl)-1-pyrrolidinyl]-1-cyclopropyl-6,8-difluoro-1,4-dihydro-4-oxo-3-quinolinyl]carbonyl]oxy]methyl]-6-[(R)-1-hydroxyethyl]-7-oxo-1-azabicyclo[3.2.0]hept-2-ene-2-carboxylic acid

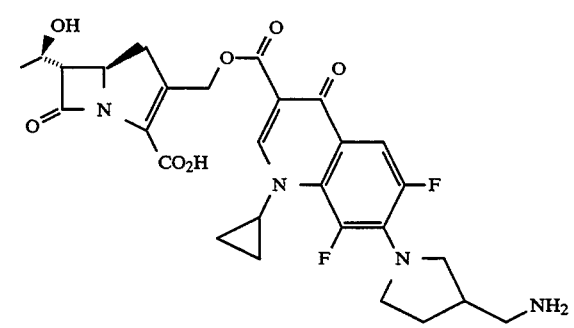

[5R,(5α,6α)]-3-[[[6,8-Difluoro-1-(2-fluoroethyl)-1,4-dihydro-4-oxo-7-(4-methyl-1-piperazinyl)-3-quinolinyl]carboxyl]oxy]methyl]-6-[(R)-1-hydroxyethyl]-6β-methyl-7-oxo-1-azabicyclo[3.2.0]hept-2-ene-2-carboxylic acid

[5R,(5α,6α)]-3-[[[[8-Ethyl-5,8-dihydro-5-oxo-2-(1-piperazinyl) pyrido[2,3-d]pyrimidinyl)carbonyl]oxy]methyl]-6-[(R)-1-hydroxy ethyl]-7-oxo-1-azabicyclo[3.2.0]hept-2-ene-2-carboxylic acid

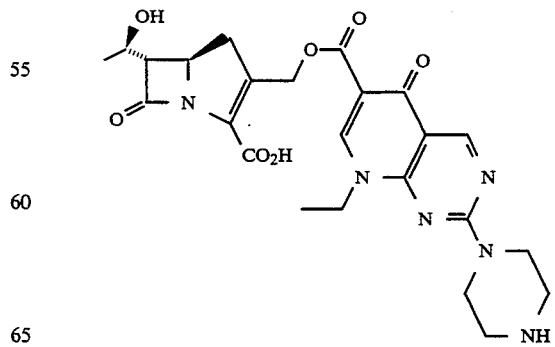

[5R,(5α,6α)]]-3-[[[1-Cyclopropyl-6-fluoro-1,4-dihydro-7-(1-piperazinyl)-4-oxo-3-3-quinolinyl]carbonyloxy]-

43
methyl]-6-[(R)-1-hydroxy ethyl]-7-oxo-1-azabicyclo[3.2.0[hept-2-ene2-carboxylic acid
44
[6R-[6α,7β]]-7-[[Carboxy(4-hydroxyphenyl)acetyl]amino]-3-[[[1-cyclopropyl-6-fluoro-1,4-dihydro-7-(1-piperazinyl)-4-oxo-3-quinolinyl]carbonyloxy]methyl-8-oxo-5-thia-1-azabicyclo[4.2.0]oct-2-ene-2-carboxylic acid
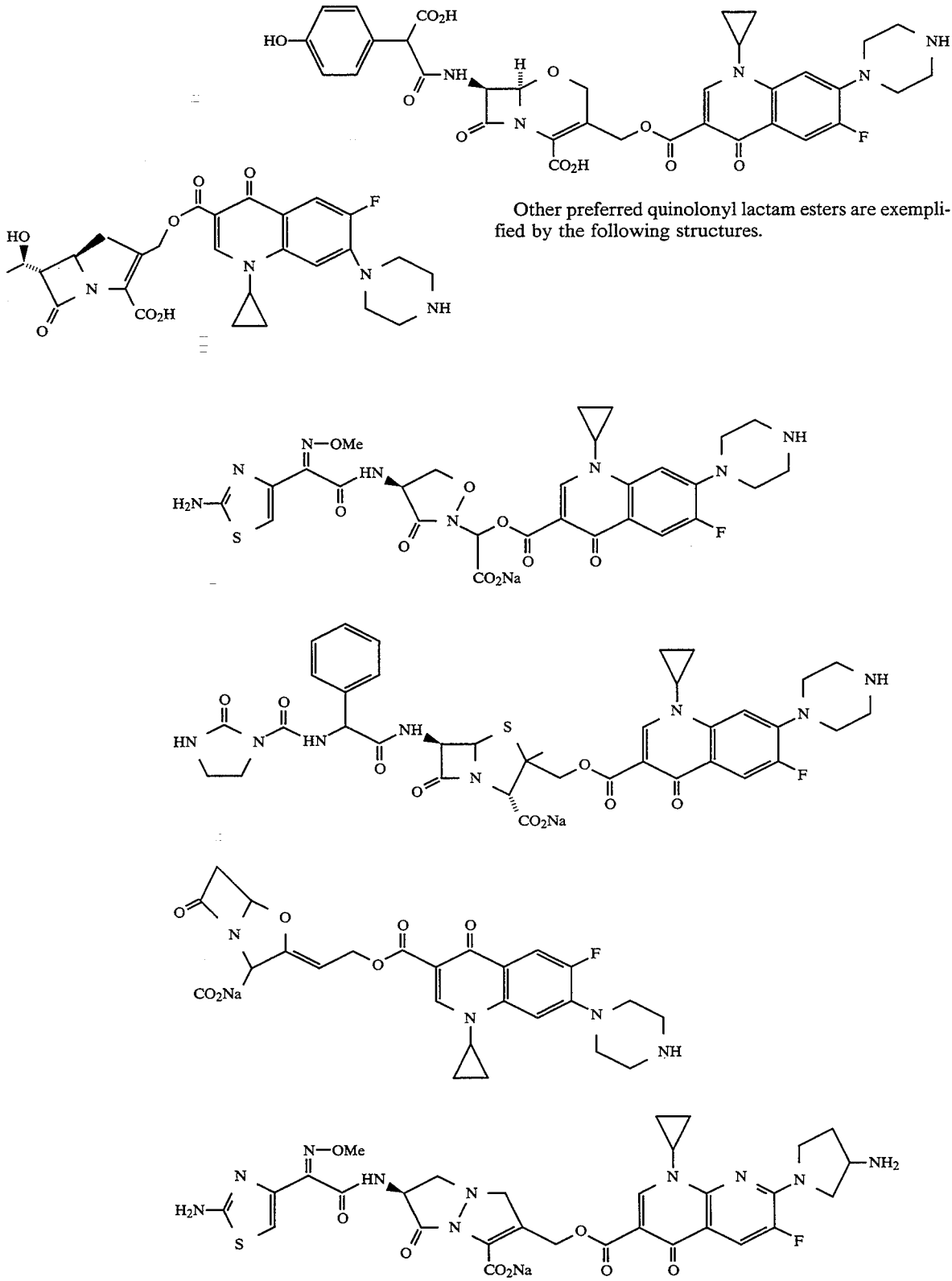
Other preferred quinolonyl lactam esters are exemplified by the following structures.

-continued
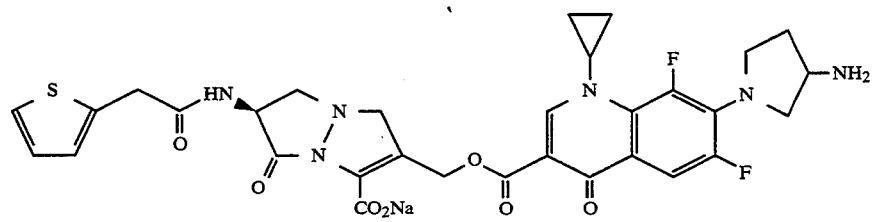
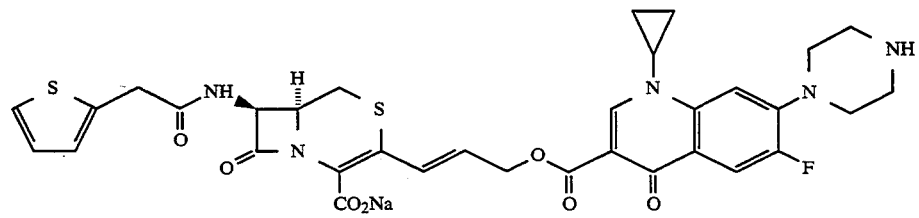
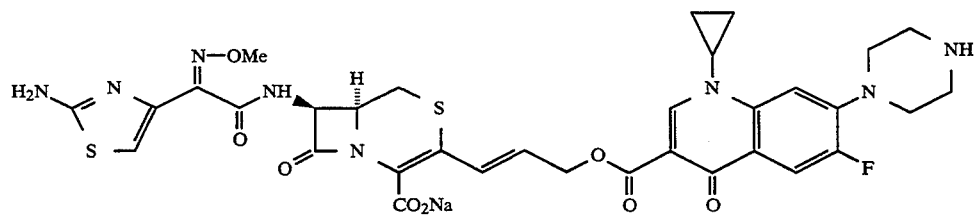
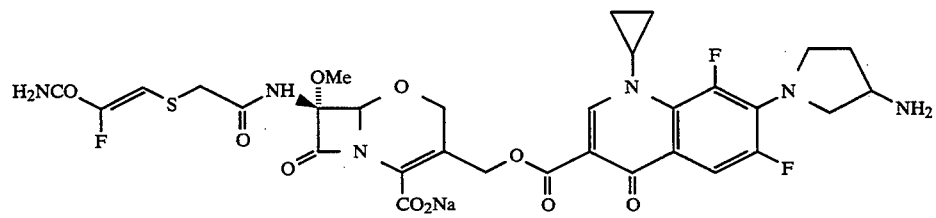
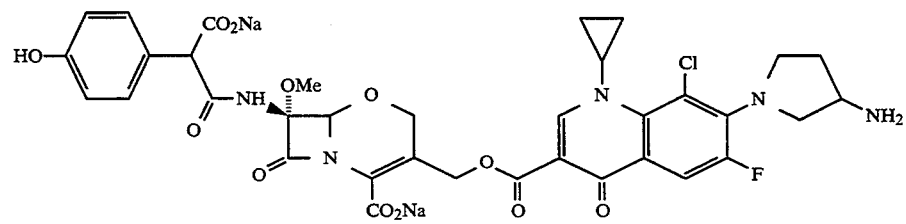
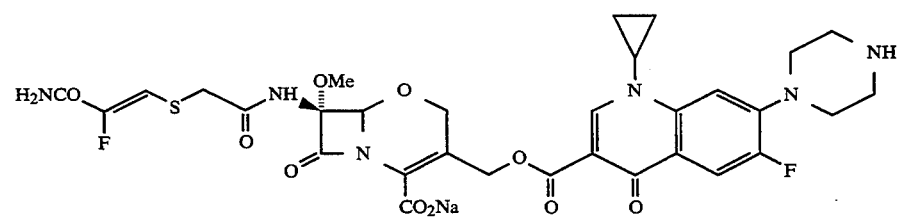
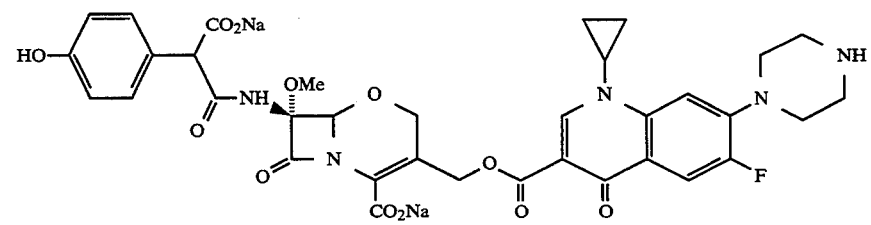

-continued
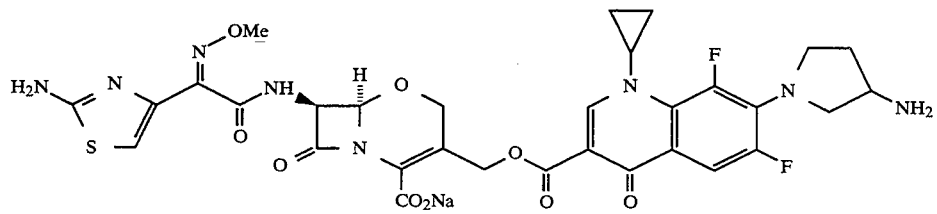
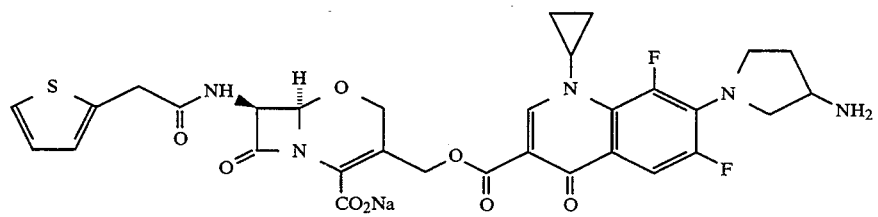
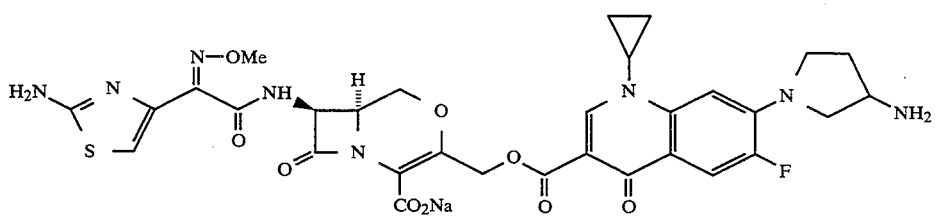
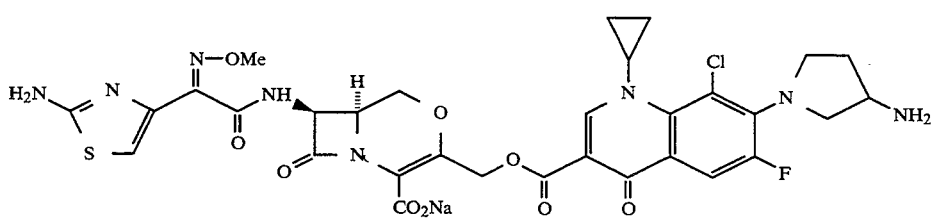
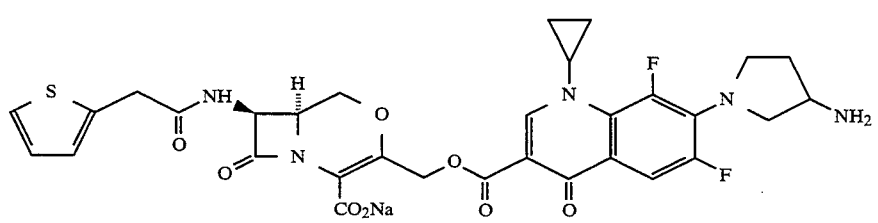
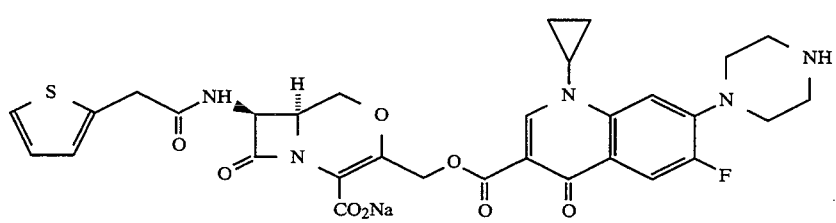
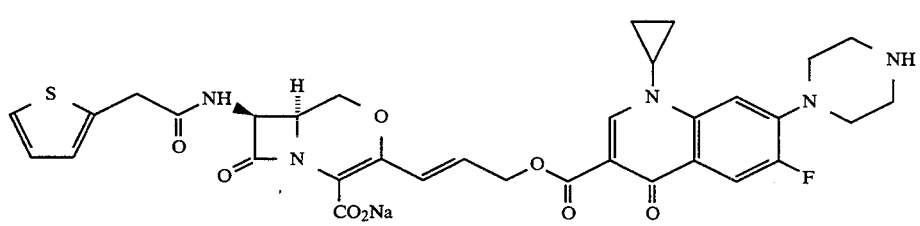

-continued
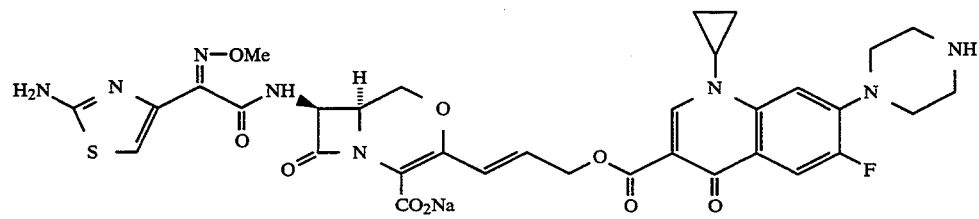
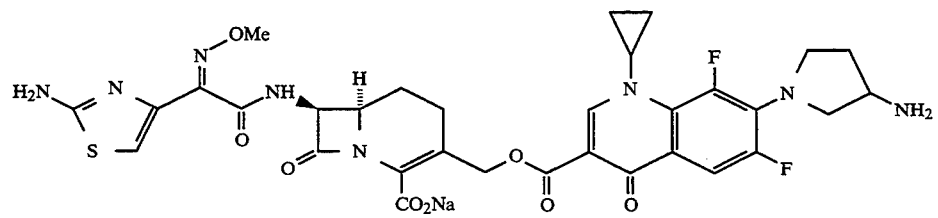
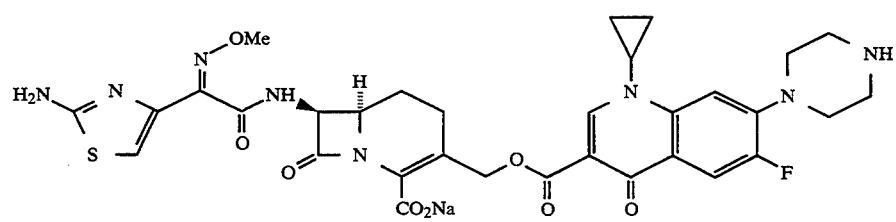
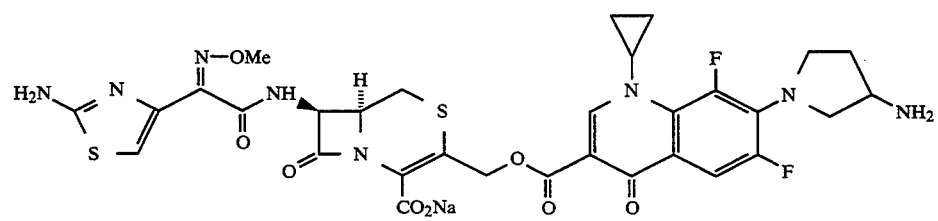
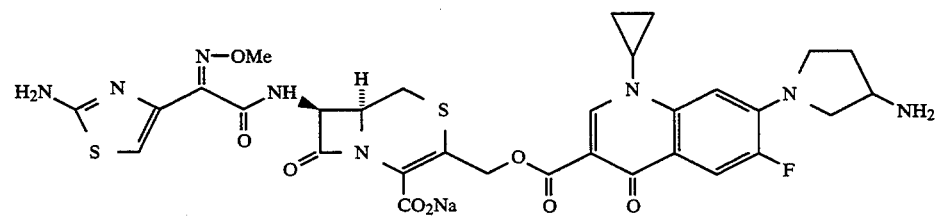
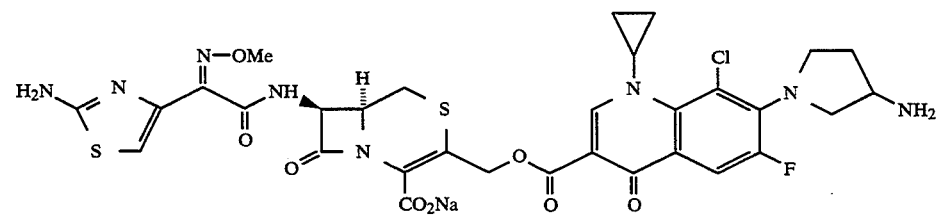
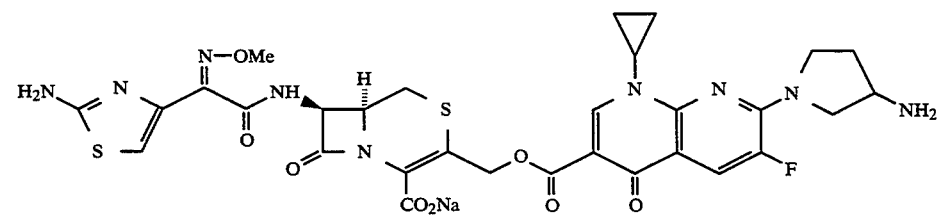

-continued
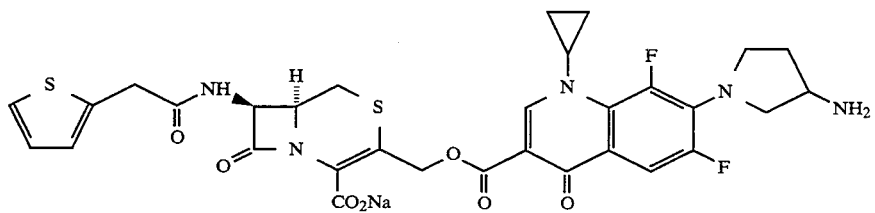
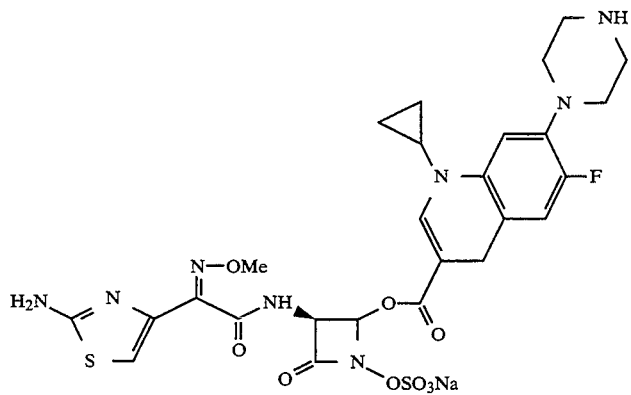
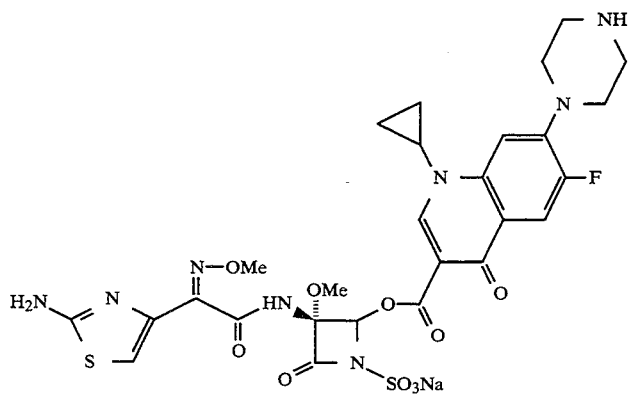
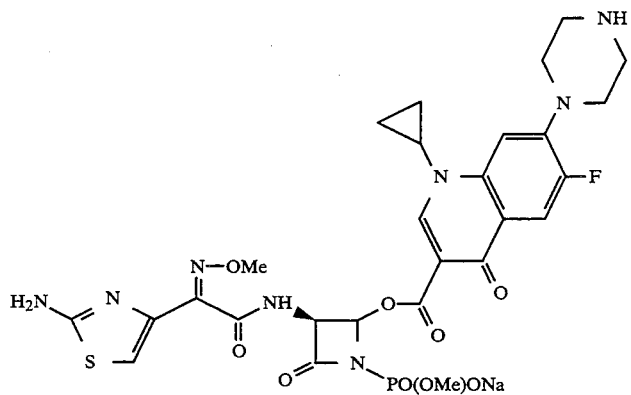

-continued
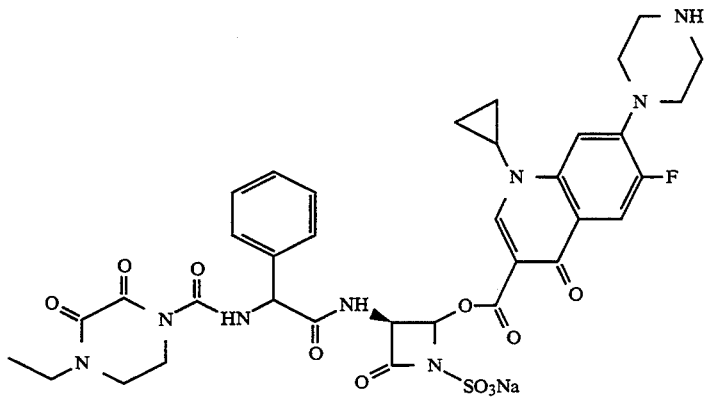
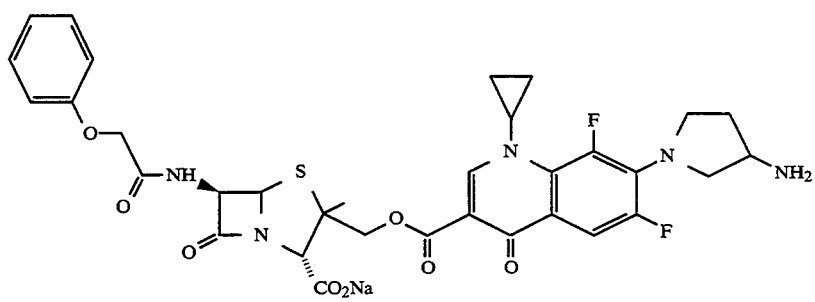
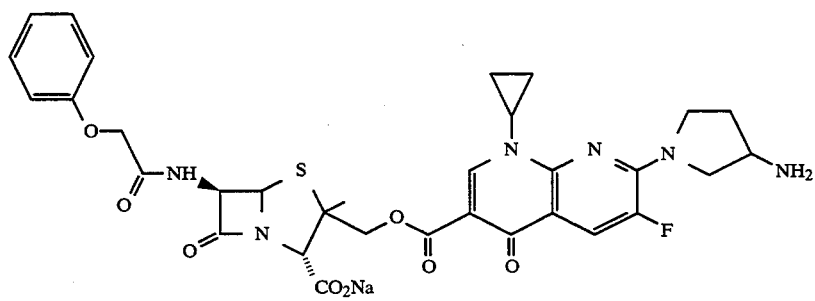
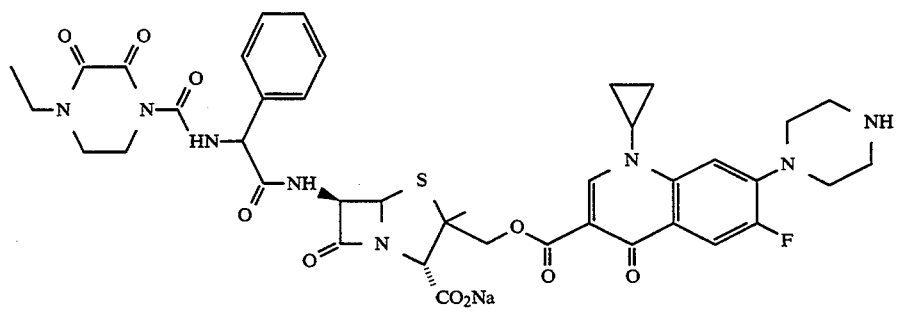
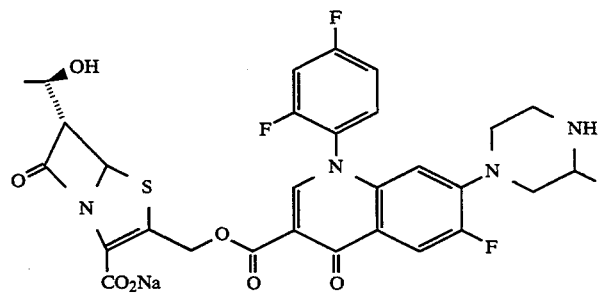

-continued

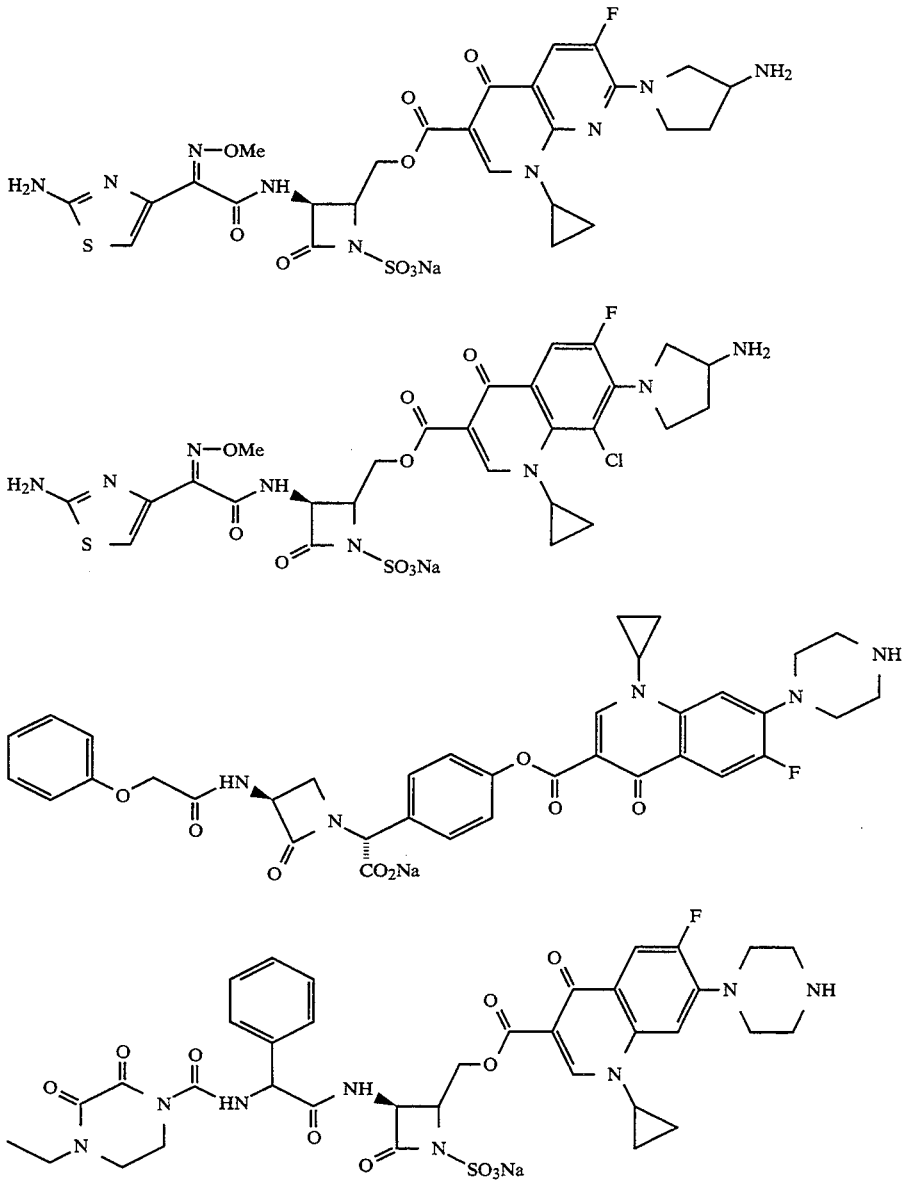

Methods of Manufacture

The quinolonyl lactam esters of this invention may be made using any of a variety of synthetic techniques known in the art. Manufacture of quinolonyl lactam esters generally involves the preparation of a lactam-containing moiety, a quinolone moiety and a procedure or set of procedures for linking the lactam-containing and quinolone moieties. Procedures for making a broad variety of lactam-containing moieties and quinolone moieties are well known in the art. For example, procedures for preparing lactam-containing moieties, and related compounds, are described in the following references, all incorporated by reference herein (including articles cited within these references): *Cephalosporins and Penicillins: Chemistry and Biology* (E. H. Flynn, ed, 972) Chapters 2, 3, 4, 5, 6, 7, 15 and Appendix I; *Recent Advances in the Chemistry of β-Lactam Antibiotics* (A. G. Brown and S. M. Roberts, ed., 1985); *Topics in Antibiotic Chemistry*, Vol. 3, (Part B) and Vol. 4, (P. Sommes, ed., 1980); *Recent Advances in the Chemistry of β-lactam Antibiotics* (J. Elks, ed., 1976); *Structure-Activity Relationships Among the Semisynthetic Antibiotics* (D. Perlman, ed, 1977); Chapts. 1, 2, 3, 4; *Antibiotics, Chemotherapeutics and Antibacterial Agents for Disease Control* (M. Grayson, ed, 1982); Chemistry and Biology of β-Lactam Antibiotics, Vols 1-3 (K. B. Morin and M. Gorman, eds, 1982); 4 *Medicinal Research Reviews* 1-24 (1984); 8 *Medicinal Research Review* 393-440 (1988); 24 *Angew. Chem. Int. Ed. Engl.* 180-202 (1985); 40 *J. Antibiotics* 182-189 (1987); European Patent Publication 266,060; 42 *J. Antibiotics* 993 (1989); U.S. Pat. No. 4,742,053; 35 *Chem. Pharm. Bull.* 1903-1909 (1987); 32 *J. Med. Chem.*, 601-604 (1989); U.S. Pat. No. 4,791,106; Japanese Patent Publication 62/158291; 31 *J. Med. Chem.* 1987-1993 (1988); 30 *J. Med. Chem.*, 514-522 (1987); 28 *Tet. Let.* 285-288 (1987); 28 *Tet. Let.* 289-292 (1987); 52 *J. Org. Chem.*, 4007-4013 (1987); 40 *J. Antibiotic*, 370-384 (1987); 40 *J. Antibiotic*, 1636-1639 (1987); 37 *J. Antibiotics*, 685-688 (1984); 23 Heterocycles, 2255-2270; 27 *Heterocycles*, 49-55; 33 *Chem. Pharm. Bull.*

4371–4381 (1985); 28 Tet. Let, 5103–5106 (1987); 53 J. Org. Chem., 4154–4156 (1988); 39 J. Antibiotics, 1351–1355 (1986); 59 Pure and Appl. Chem., 467–474 (1987); 1987 J.C.S. Chem. Comm.; 44 Tetrahedron, 3231–3240 (1988); 28 Tet. Let., 2883–2886, (1987); 40 J. Antibiotics, 1563–1571 (1987); 33 Chem. Pharm. Bull., 4382–4394 (1985); 37 J. Antibiotics, 57–62 (1984); U.S. Pat. No. 4,631,150; 34 Chem. Pharm. Bull., 999–1014 (1986); 52 J. Org. Chem., 4401–4403 (1987); 39 Tetrahedron, 2505–2513 (1983); 38 J. Antibiotics, 1382–1400 (1985); European Patent Application 053,815; 40 J. Antibiotics, 1563–1571 (1987); 40 J. Antibiotics, 1716–1732 (2987); 47 J. Org. Chem., 5160–5167 (1981); U.S. Pat. Nos. 4,777,252; 4,762,922; European Patent Publication 287,734; U.S. Pat. No. 4,762,827; European Patent Publication 282,895; European Patent Publication 282,365; U.S. Pat. No. 4,777,673.

Also, for example, procedures for preparing quinolones useful in the methods of this invention are described in the following references, all incorporated by reference herein (including articles listed within these references); 21 Progress in Drug Research, 9–104 (1977); 31 J. Med. Chem,, 503–506 (1988); 32 J. Med. Chem., 1313–1318 (1989); 1987 Liebigs Ann. Chem., 71–879 (1987); 14 Drugs Exptl. Clin. Res., 379–383 (1988); 31 J. Med. Chem., 983–991 (1988); 32 J. Med. Chem., 537–542 (1989); 78 J. Pharm. Sci., 585–588 (1989); 26 J. Het. Chem., (1989); 24 J. Het. Chem., 181–185 (1987); U.S. Pat. No. 4,599,334, 35 Chem. Pharm. Bull., 2281–2285 (1987); 29 J. Med. Chem., 2363–2369 (1986); 31 J. Med. Chem., 991–1001 (1988); 25 J. Het. Chem., 479–485 (1988); European Patent Publication 266,576; European Patent Publication 251,308, 36 Chem. Pharm. Bull., 1223–1228 (1988); European Patent Publication 227,088; European Patent Publication 227,039; European Patent Publication 228,661; 31 J. Med. Chem., 1586–1590 (1988); 31 J. Med. Chem., 1598–1611 (1988); and 23 J. Med. Chem., 1358–1363 (1980).

The quinolonyl lactam esters of this invention may be made by the following general reaction sequence:

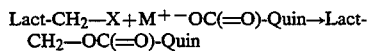

Lact-CH$_2$—X+M$^+$ $^-$OC(=O)-Quin→Lact-CH$_2$—OC(=O)-Quin where X is a reactive leaving group (such as halo, a sulfonate ester or other activated hydroxyl functionality), "Lact" generically represents an appropriately protected lactam-containing moiety (such as a penem, carbapenem, oxacephem, or carbacephem) and "Quin" represents an appropriately protected quinolone moiety. The reaction can be envisioned as a nucleophilic displacement of the reactive X substituent from the lactam by the quinolone carboxylic acid or salt, to form an ester coupled conjugate of the lactam and quinolone.

For Lact and Quin, certain functional groups contained in the structures (such as carboxyl, hydroxyl, and amino) may need to be blocked in order to prevent undesired competing side reactions from occurring with X. For example, suitable protecting groups for carboxyl substituents include esters; protecting groups for hydroxyl substituents include ethers, esters, and carbonates; and protecting groups for amino substituents include carbamates and amides. If such protecting groups are employed, then appropriate deprotecting chemistry, that will not decompose the ester coupled conjugate, may be required to obtain antimicrobially-active products.

If the lactam-containing moiety is a monocyclic beta-lactam, an alternative coupling strategy may be employed as outlined by the following sequence, where X is a heteroatom (O, S, halo, etc.) substituent linked to the lactam.

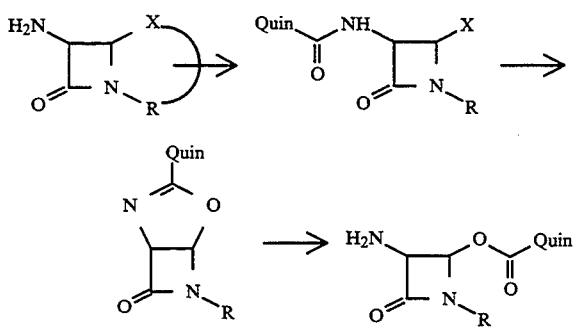

This sequence involves amide formation between the lactam and the quinolone, rearrangement displacing X and liberation of the ester by hydrolysis. The lactam containing structure may initially be mono-or bicyclic. The ester coupled product will be monocyclic.

Compositions

The compositions of this invention comprise:
(a) a safe and effective amount of a quinolonyl lactam ester; and
(b) a pharmaceutically-acceptable carrier.

A "safe and effective amount" of a quinolonyl lactam ester is an amount that is effective, to inhibit microbial growth at the site of an infection to be treated in a human or lower animal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the quinolonyl lactam esters therein, and the dosage regimen desired for the composition. The compositions of this invention are preferably provided in unit dosage form. As used herein, a "unit dosage form" is a composition of this invention containing an amount of a quinolonyl lactam ester that is suitable for administration to a human or lower animal subject, in a single dose, according to good medical practice. These compositions preferably contain from about 30 mg to about 20,000 mg, more preferably from about 50 mg (milligrams) to about 7000 mg, more preferably from about 500 mg to about 1500 mg, of a quinolonyl lactam ester. The compositions of this invention may be in any of a variety of forms, suitable (for example) for oral, rectal, topical or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the antimicrobial activity of the quinolonyl lactam ester. The amount of carrier employed in conjunction with the quinolonyl lactam ester is sufficient to provide a practical quantity of material for administration per unit dose of the quinolonyl lactam ester. Techniques and compositions for making dosage forms useful in the methods of this invention are described in the following references, all incorporated by reference herein: 7 *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight by the total composition.

Various oral dosage forms can be used, including such solid forms as tablets, capsules, granules and bulk powders. These oral forms comprise a safe and effective amount, usually at least about 5%, and preferably from about 25% to about 50%, of the quinolonyl lactam ester. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents. Preferred carriers for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the quinolonyl lactam ester. Suitable carriers for topical administration preferably remain in place on the skin as a continuous film, and resist being removed by perspiration or immersion in water. Generally, the carrier is organic in nature and capable of having dispersed or dissolved therein the quinolonyl lactam ester. The carrier may include pharmaceutically-acceptable emolients, emulsifiers, thickening agents, and solvents.

Methods of Administration

This invention also provides methods of treating or preventing an infectious disorder in a human or other animal subject, by administering a safe and effective amount of a quinolonyl lactam ester to said subject. As used herein, an "infectious disorder" is any disorder characterized by the presence of a microbial infection. Preferred methods of this invention are for the treatment of bacterial infections. Such infectious disorders include (for example) central nervous system infections, external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients (such as patients receiving cancer chemotherapy, or organ transplant patients).

The quinolonyl lactam esters and compositions of this invention can be administered topically or systemically. Systemic application includes any method of introducing the quinolonyl lactam ester into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, are mutually dependent. The dosage and treatment regimen will also depend upon such factors as the specific quinolonyl lactam ester used, the resistance pattern of the infecting organism to the quinolonyl lactam ester used, the ability of the quinolonyl lactam ester to reach minimum inhibitory concentrations at the site of the infection, the nature and extent of other infections (if any), the personal attributes of the subject (such as weight), compliance with the treatment regimen, and the presence and severity of any side effects of the treatment.

Typically, for a human adult (weighing approximately 70 kilograms), from about 75 mg to about 30,000 mg, more preferably from about 100 mg to about 20,000 mg, more preferably from about 500 mg to about 3500 mg, of quinolonyl lactam ester are administered per day. Treatment regimens preferably extend from about 1 to about 56 days, more preferably from about 7 to about 28 days, in duration. Prophylactic regimens (such as avoidance of opportunistic infections in immunocompromised patients) may extend 6 months, or longer, according to good medical practice.

A preferred method of parenteral administration is through intramuscular injection. As is known and practiced in the art, all formulations for parenteral administration must be sterile. For mammals, especially humans, (assuming an approximate body weight of 70 kilograms) individual doses of from about 100 mg to about 7000 mg, preferably from about 500 mg to about 1500 mg, are acceptable.

A preferred method of systemic administration is oral. Individual doses of from about 100 mg to about 2500 mg, preferably from about 250 mg to about 1000 mg are preferred.

Topical administration can be used to deliver the quinolonyl lactam ester systemically, or to treat a local infection. The amounts of quinolonyl lactam ester to be topically administered depends upon such factors as skin sensitivity, type and location of the tissue to be treated, the composition and carrier (if any) to be administered, the particular quinolonyl lactam ester to be administered, as well as the particular disorder to be treated and the extent to which systemic (as distinguished from local) effects are desired.

The following non-limiting examples illustrate the compounds, compositions, processes, and uses of the present invention.

EXAMPLE 1

[5R)][5α,6α]]-3-[[7-[(3-amino-1-pyrrolidinyl)-6-fluoro-1-(2,4-difluorophenyl)-1,4-dihydro-4-oxo-3-(1,8-naphthyridinyl)]carbonyloxy]methyl]-6-(1(R)-hydroxyethyl)-7-oxo-4-thia-1-azabicyclo[3.2.0]hept-2-ene-2-carboxylic acid, according to this invention is made by the following general reaction sequence.

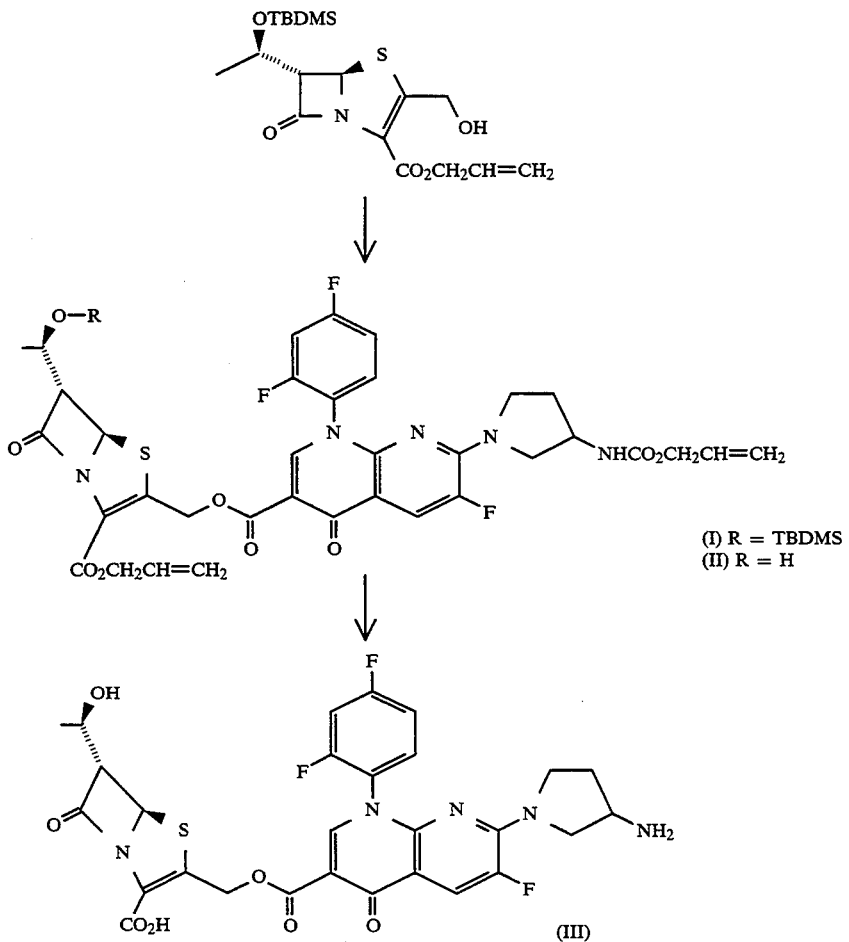

Approximately 0.28 mmol (0.112 g) of [5R][5α,6α]]-3-hydroxymethyl-6-(1(R)-t-butyldimethylsiloxyethyl)-7-oxo-thia-1-azabicyclo[3.2.0]hept-2-ene-2-carboxylic acid, allyl ester (made according to U.S. Pat. No. 4,631,150, Battistini et al., issued Dec. 23, 1986, incorporated by reference herein) is dissolved in approximately 10 ml THF (tetrahydrofuran). Under a nitrogen blanket, at approximately 22° C. (72° F.), approximately 0.32 mmol of diethylazodicarboxylate, 0.32 mmol of 6-fluoro-1-(2,4-difluorophenyl)-1,4-dihydro-4-oxo-7-[3-(1-phenyl)oxycarbonyl]amino-1-pyrrolidinyl]-3-(1,8-naphthyridine)-carboxylic acid and 0.32 mmol PPh₃ (triphenyl phosphine) are sequentially added with stirring. After approximately 15 minutes, 10 ml phosphate buffer (0.5M, pH 7.0) is added, the THF is rapidly evaporated, and the aqueous residue is extracted with dichloromethane. Drying and removal of the solvent in vacuo yields the crude Product (I) which is further purified by flash chromatography.

Approximately 0.15 g of Product (I) (0.18 mmol) is dissolved in 20 ml THF. Then 40 microliters of glacial acetic acid and 60 mg of tetrabutyl ammonium fluoride are added and the reaction is allowed to stand approximately 24 hours at ambient temperature. The THF is evaporated and the residue is taken up in dichloromethane. Extraction with aqueous bicarbonate, and solvent reduction, yields product (II).

Approximately 60 mg of Product (II) (0.08 mmol) is then dissolved in 15 ml THF at ambient temperature, and 5 mg PPh₃, 44 mg sodium ethylhexanoate and 5 mg Pd(PPh₃)₄ are added with stirring. Within several minutes a precipitate forms and is collected by filtration. The solid final product (III) is purified to analytical purity by repeated trituration. Similarly, the following quinolonyl lactam esters are prepared according to the general procedure of this Example, with substantially similar results.

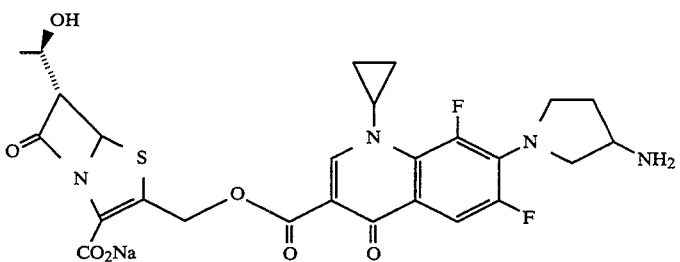

using the quinolone 7-(3-aminopyrrolidinyl)-1-cyclopropyl-6,8-difluoro-1,4-dihydro-4-oxo-3-quinolinecarboxylic acid (prepared according to J. P. Sanchez, et al., J. Med. Chem., 1988, 31, 983)

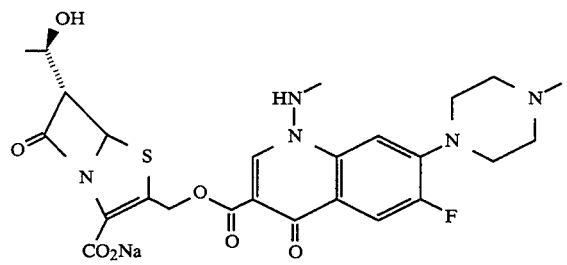

using the quinolone 6-fluoro-1,4-dihydro-1-methylamino-7-(4-methyl-1-piperazinyl )-4-oxo-3-quinoline carboxylic acid (prepared according to M. P. Wentland, et al., J. Med. Chem. 1984, 27, 1103)

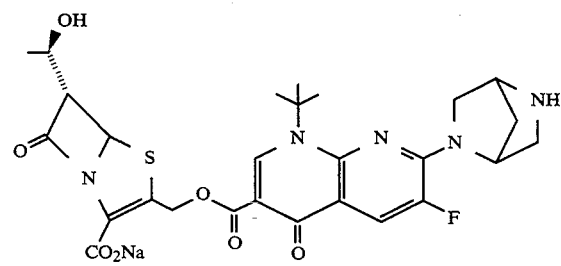

using the naphthyridinone 7-(2,5-diazabicyclo[2.2.1-]heptan-2-yl)-1-(1,1-dimethyl ethyl)-6-fluoro-1,4-dihydro-4-oxo-1,8-naphthyridine-3-carboxylic acid (prepared according to A. Weber, et al., Eur. Pat. Appl. EP 266576)

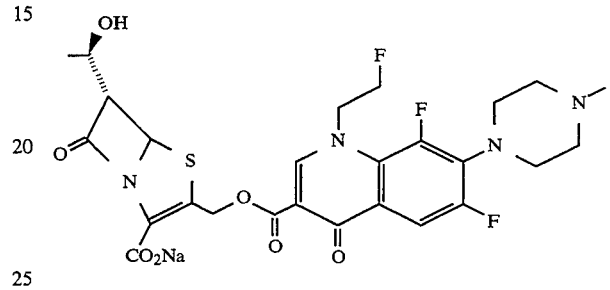

using the quinolone 6,8-difluoro-1-(2-fluoroethyl)-1,4-dihydro-4-oxo-7-(4-methyl-1-piperazinyl)-3-quinolinecarboxylic acid (prepared according to T. Iridura, Aust. Pat. Specif. AU 537813)

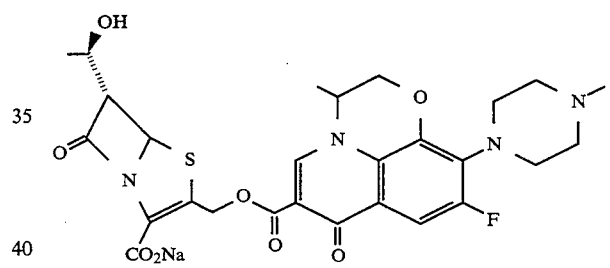

using the quinolone 9-fluoro-4,7-dihydro-3-methyl-10-(4-methyl-1-piperazinyl)-7-oxo-2H-pyrido[1,2,3-de]-1,4-benzoxazine-6-carboxylic acid (prepared according to I. Hagakawa et al., Chem. Pharm Bull. 1984, 32, 4907)

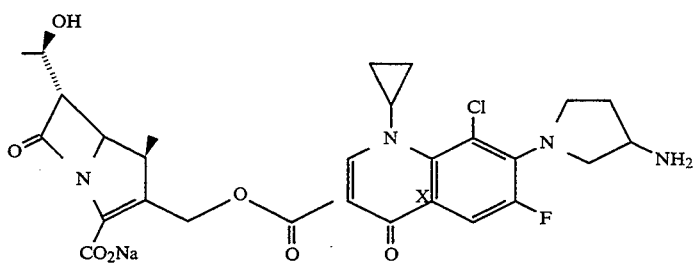

using the quinolone 7-(3-aminopyrrolidinyl)-8-chloro-1-cyclopropyl-6-fluoro-1,4-dihydro-4-oxo-3-quinolinecarboxylic acid (prepared according to J. P. Sanchez, et al., J. Med. Chem., 1988, 31, 983) and the B-lactam [5R-[4β,5α,6α]]-6-[(R)-1-(t-butyldimethylsilyloxy)ethyl]-2-(hydroxymethyl)-4-methyl-7-oxo-1-azabicyclo[3.2.0]hept-2-ene-2-carboxylic acid allyl ester (prepared according to B. G. Christensen et al., Eur. Pat. Appl. EP 185315 A1, 1986)

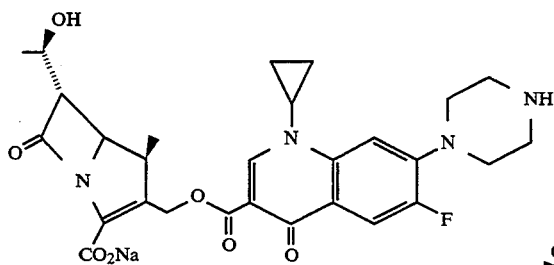

using the quinolone 1-cyclopropyl-6-fluoro-1,4-dihydro-4-oxo-7-(1-piperazinyl)-3-quinolinecarboxylic acid (prepared according to K. Grohe et al., Get. Offen. DE 3142854) and the B-lactam [5R-[4β,5α,6α]]-6-[(R)-1-(t-butyldimethylsilyloxy)ethyl]-2-hydroxymethyl)-4-methyl-7-oxo-1-azabicyclo[3.2.0]hept-2-ene-2-carboxylic acid allyl ester (prepared according to B. G. Christensen et al., Eur. Pat. Appl. EP 185315 A1, 19861).

EXAMPLE 2

According to the general procedure of Example 1, the following quinolonyl lactam ester is made:

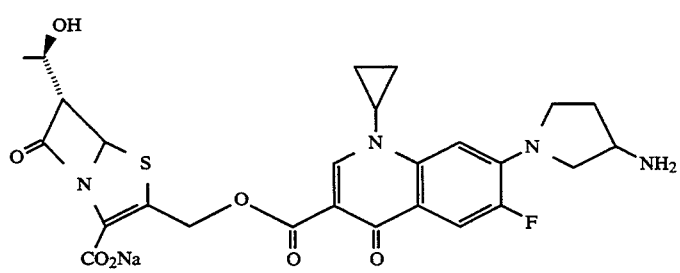

using the quinolone 7-(3-aminopyrrolidinyl)-1-cyclopropyl-6-fluoro-1,4-dihydro-4-oxo-3-quinolinecarboxylic acid (prepared according to J. P. Sanchez, et al., J. Med. Chem., 1988, 31, 983).

Similarly, the following quinolonyl lactam ester is prepared according to the general procedure of this Example, with substantially similar results.

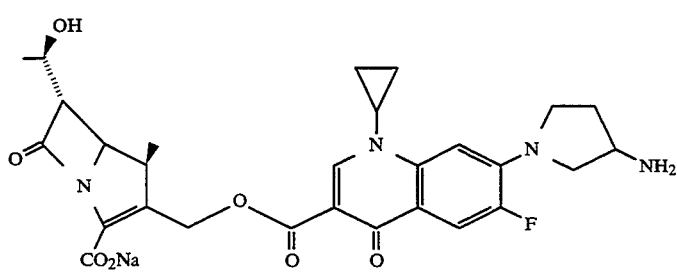

using the B-lactam the [5R-[4β,5α,6α]]-6-[(R)-1-(t-butyldimethylsilyloxy)ethyl]-2-(hydroxymethyl)-4-methyl-7-oxo-1-azabicyclo[3.2.0]hept-2-ene-2-carboxylic acid allyl ester (prepared according to B. G. Christensen et al., Eur. Pat. Appl. EP 185315 A1, 1986).

EXAMPLE 3

According to the general procedure of Example 1, the following quinolonyl lactam ester is made:

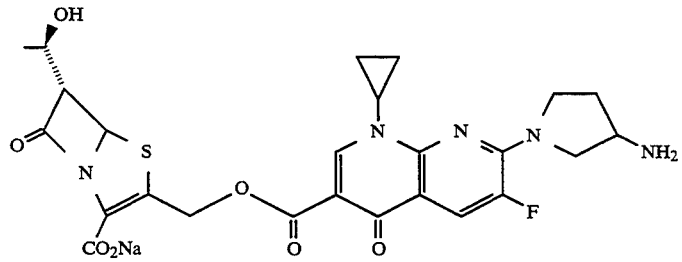

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., J. Med. Chem., 1988, 31,983).

Similarly, the following quinolonyl lactam ester is prepared according to the general procedure of this Example, with substantially similar results.

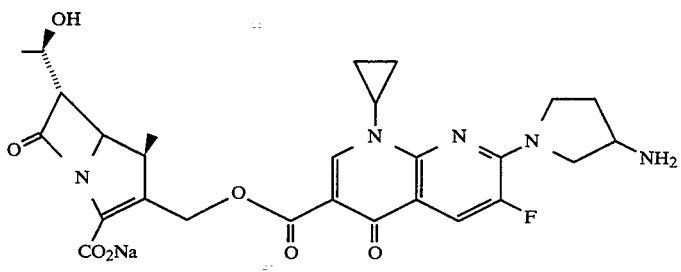
15
using the B-lactam [5R-[4β,5α,6α]]-6-[(R)-1-(t-butyl-dimethylsilyloxy)ethyl]-2-(hydroxymethyl)-4-methyl-7-oxo-1-azabicyclo[3.2.0]hept-2-ene-2-carboxylic acid allyl ester (prepared according to B. G. Christensen et al., Eur. Pat. Appl. EP 185315 A1, 1986)
EXAMPLE 4
[5R-[5α6α]]-3-[[[1-Cyclopropyl-6-fluoro-1,4-dihydro-4-oxo-7-(1-piperazinyl)-3-quinolinyl]carbonyloxy]methyl]-6-[(R)-1-hydroxyethyl[-7-oxo-4-thia-1-azabicyclo[3.2.0]hept-2-ene-2-carboxylic Acid
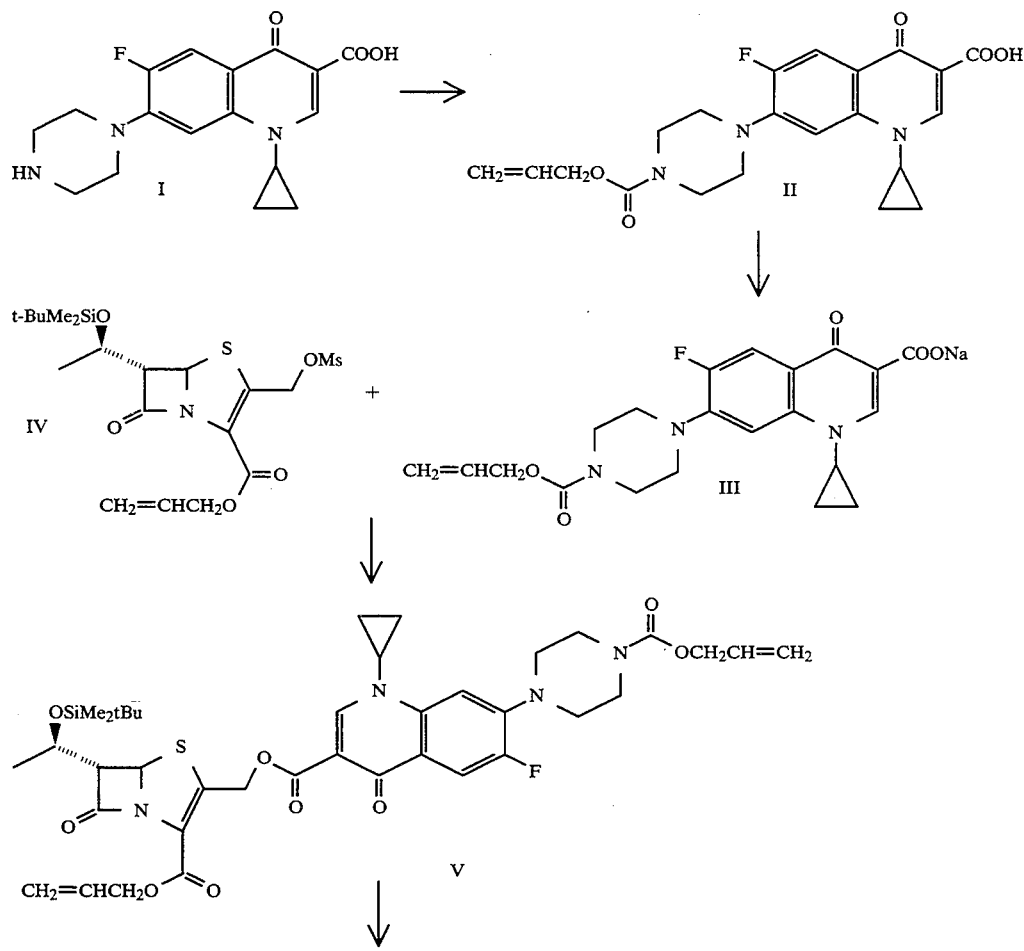

-continued

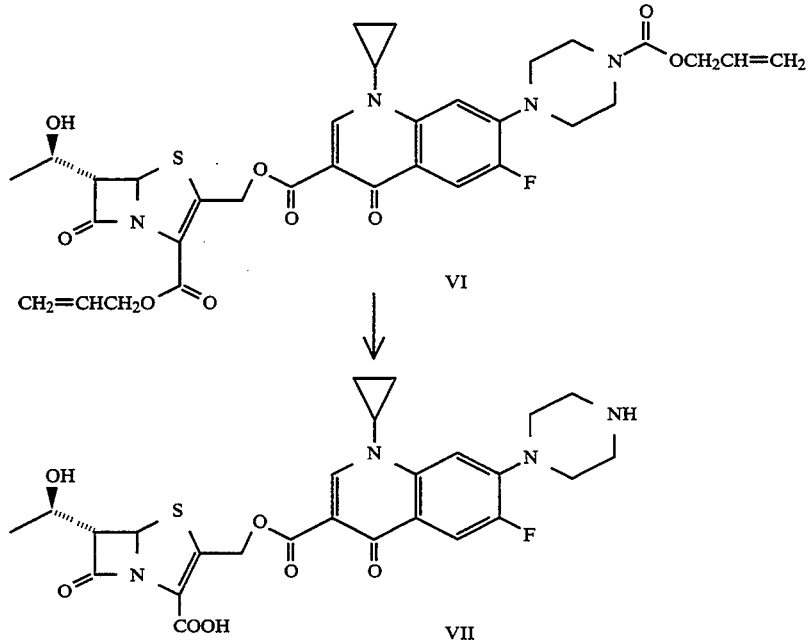

A mixture of approximately 5.0 g of ciprofloxacin I in 175 ml of water at approximately 0° C. is adjusted to approximately pH 12 by adding 1N NaOH. To this solution is added approximately 44 ml of acetone followed by the dropwise addition of approximately 2.7 g of allylchloroformate in 33 ml of acetone. The reaction is stirred approximately one hour in the cold while maintaining the mixture at pH 10–12 by addition of more 1N NaOH. Then the reaction is concentrated to approximately 125 ml and is extracted twice with ether. The aqueous layer is cooled in an ice bath, acidified with 10% HCl and is extracted three times with ethyl acetate. The extract is washed with water, dried over $Na_2SO_4$, filtered, and the filtrate is concentrated to dryness to give II. To a solution of approximately 6 g of II in $CH_2Cl_2$ at approximately 0° C. is added dropwise a solution of approximately 0.73 g of NaOH in 5 ml of methanol. The mixture is stirred for one hour at ambient temperature, and concentrated to dryness. The residue is triturated in ether and the sodium salt III is collected by filtration.

Separately, to a solution of approximately 5.0 g of [5R-[5α,6β]]-3-hydroxymethyl-6-(1-(R)-t-butyldimethylsiloxyethyl)-7-oxo-4-thia-1-azabicyclo[3.2.0 ]hept-2-ene-2-carboxylic acid allyl ester and 1.7 ml of triethylamine in 30 ml of $CH_2Cl_2$ at approximately −40° C. is added approximately 1.1 ml of mesyl chloride. The reaction is stirred for approximately 10 minutes, then washed with 10% aqueous $NaHCO_3$ and water. The organic phase is dried over $Na_2SO_4$, filtered, and the filtrate is concentrated to dryness to give IV. To a solution of approximately 4.3 g of the mesylate IV in 30 ml of DMF at approximately 20° C. is added approximately 3.9 g of III and the reaction is stirred cold for approximately four hours and at ambient temperature for approximately one hour. The reaction is concentrated to dryness in vacuo and the residue is dissolved in $CH_2Cl_2$ and washed with water. The organic phase is dried over $Na_2SO_4$, filtered and the filtrate is concentrated to dryness. The residue is purified by flash chromatography (silica gel) to give V. To a mixture of approximately 2.6 g of V and 2 ml of glacial acetic acid in 30 ml of THF at room temperature is added approximately 3.5 g of tetra-n-butylammonium fluoride trihydrate. The mixture is stirred for approximately 30 hours, then concentrated to dryness and residue is purified by flash chromatography (silica gel) to give VI. To a mixture of approximately 1.3 g of VI, 0.19 ml of water and 0.027 g of bis(triphenylphosphine)palladium chloride in approximately 36 ml of $CH_2Cl_2$ at approximately 19° C. is added approximately 1.1 ml of tributyltinhydride. The mixture is rapidly stirred for approximately 10 minutes and the precipitate is collected by filtration. The solid is triturated in acetone and is collected by filtration to afford the title compound VII.

Similarly, the following quinolonyl lactam esters are prepared according to the general procedure of this Example, with substantially similar results.

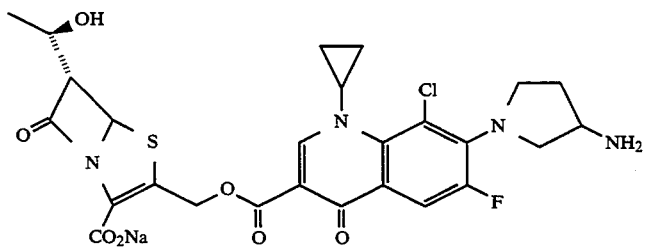

using the quinolone 7-(3-aminopyrrolidinyl)-8-chloro-1-cyclopropyl-6-fluoro-1,4-dihydro-4-oxo-3-quinolinecarboxylic acid (prepared according to J. P. Sanchez, et al., J. Med. Chem., 1988, 31, 983)

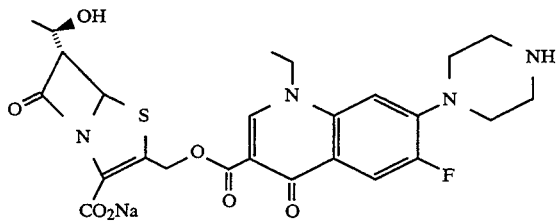

the quinolone 1-ethyl-6-fluoro-1,4-dihydro-4-oxo-7-(1-piperazinyl)-3-quinoline carboxylic acid (prepared according to H. Koga, et al., J. Med. Chem. 1980, 23, 1358)

quinolinecarboxylic acid (prepared according to D. T. W. Chu et al., J. Med. Chem. 1985, 28, 1558)

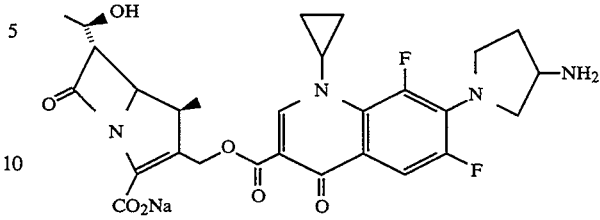

using the quinolone 7-(3-aminopyrrolidinyl)-1-cyclopropyl-6,8-difluoro-1,4-dihydro-4-oxo-3-quinolinecarboxylic acid (prepared according to J. P. Sanchez, et al., J. Med. Chem., 1988, 31, 983) and the B-lactam [5R-[4β,5α,6α]]-6-[(R)-1-(t-butyldimethylsilyloxy)ethyl]-2-(hydroxymethyl)-4-methyl-oxo-1-azabicyclo [3.2.0] hept-2-ene-2-carboxylic acid allyl ester (prepared according to B. G. Christensen et al., Eur. Pat. Appl. EP 185315 A1, 1986).

EXAMPLE 5

Product III, according to this invention, is made by the following general reaction sequence.

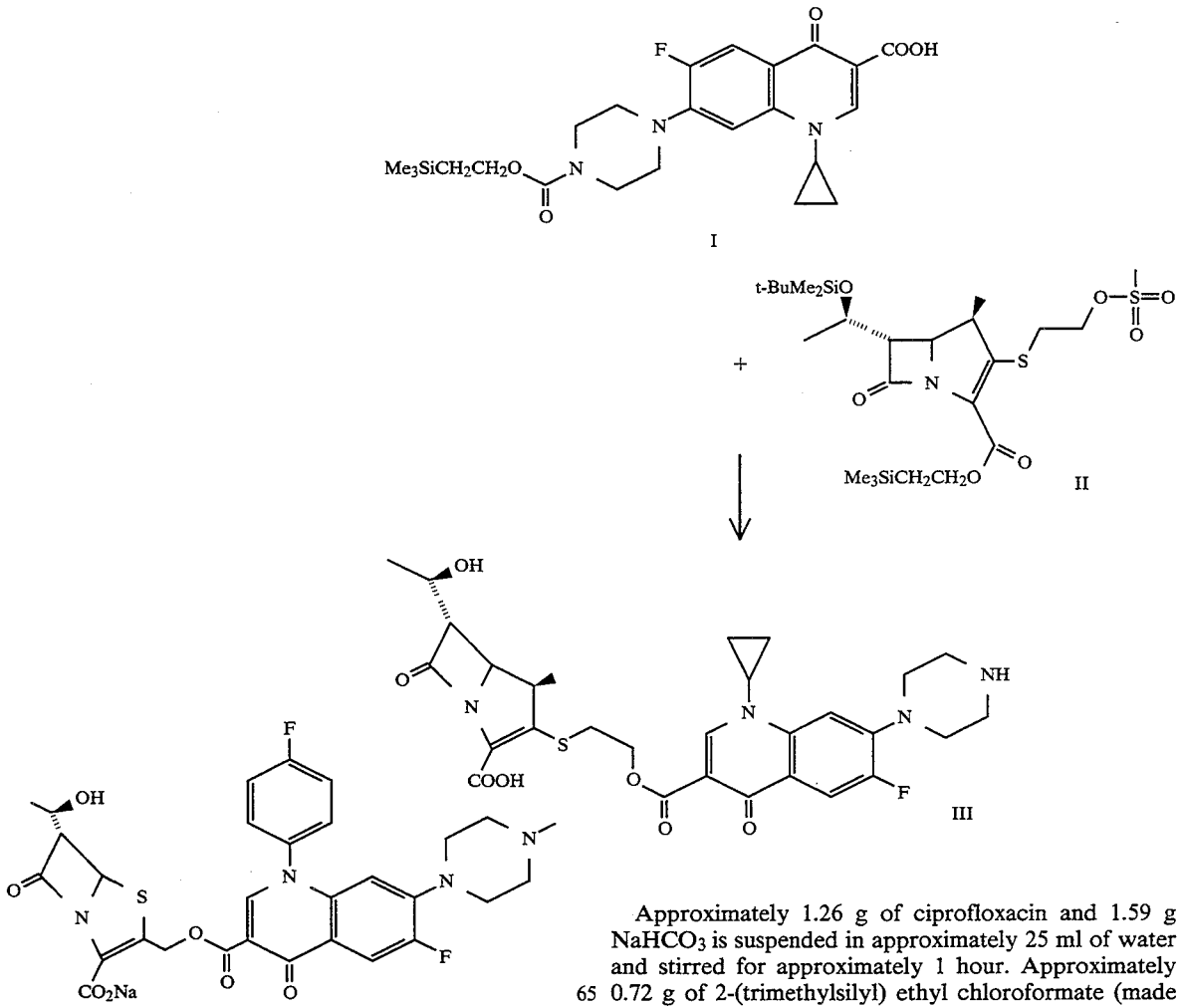

using the quinolone 6-fluoro-1-(4-fluorophenyl)-1,4-dihydro-7-(4-methyl-1-piperazinyl) 4-oxo-3-

Approximately 1.26 g of ciprofloxacin and 1.59 g NaHCO3 is suspended in approximately 25 ml of water and stirred for approximately 1 hour. Approximately 0.72 g of 2-(trimethylsilyl) ethyl chloroformate (made according to 38 Zhur obschei Khim. 1179 (1968)) in approximately 10 ml of tetrahydrofuran is added dropwise to the stirring aqueous solution. After approximately 1 hour the mixture is poured into 150 ml of chloroform and acidified with 150 ml of cold 0.1M HCl. The aqueous phase is extracted with chloroform again and the combined chloroform layers are washed successively with cold 0.1M HCl, water, and saturated aqueous sodium chloride. The chloroform solution is dried over Na$_2$SO$_4$, filtered, and concentrated. The residue is triturated with ether to provide product I after filtration.

A mixture of approximately 0.16 g of product I, 0.20 g of product II (prepared as above), and 0.040 g of NaHCO$_3$ are combined in approximately 1 ml of dimethylformamide under an inert atmosphere. The mixture is heated at approximately 70° C. for 8 hours and then cooled to room temperature. The addition of approximately 0.50 g of tetra-n-butylammonium fluoride trihydrate is followed by stirring for approximately 16 hours at room temperature. The mixture is then eluted through a Dowex® 50×4 (Na cycle) column with deionized water. The appropriate fractions are partially concentrated in vacuo, then lyophilized to give the final product III.

Similarly, the following quinolonyl lactam esters are prepared according to the general procedure of this Example, with substantially similar results.

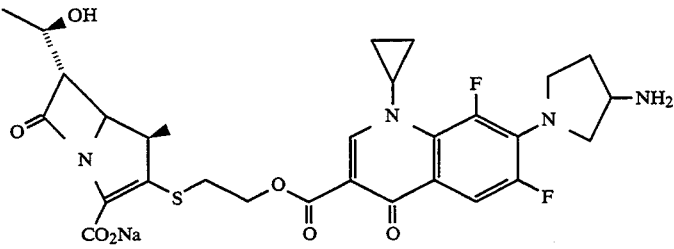

using the quinolone 7-(3-aminopyrrolidinyl)-1-cyclopropyl-6,8-difluoro-1,4-dihydro-4-oxo-3-quinolinecarboxylic acid (prepared according to J. P. Sanchez, et al., J. Med. Chem., 1988, 31,983)

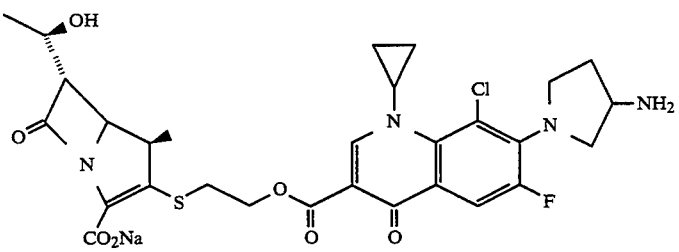

using the quinolone 7-(3-aminopyrrolidinyl)-8-chloro-1-cyclopropyl-6-fluoro-1,4-dihydro-4-oxo-3-quinolinecarboxylic acid (prepared according to J. P. Sanchez, et al., J. Med. Chem., 1988, 31,983)

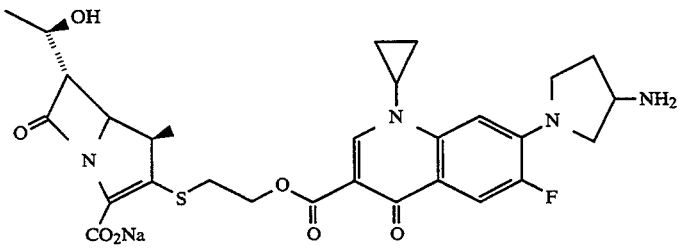

using the quinolone 7-(3-aminopyrrolidinyl)-1-cyclopropyl-6-fluoro-1,4-dihydro-4-oxo-3-quinolinecarboxylic acid (prepared according to J. P. Sanchez, et al., J. Med. Chem., 1988, 31, 983)

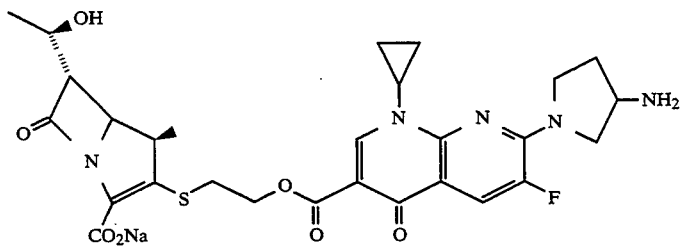

using the naphthyridinone 7-(3-aminopyrrolidinyl)-1-cyclopropyl-6-fluoro-1,4-dihydro-4-oxo-1,8-naphthyridine-3-carboxylic acid (prepared according to J. P. Sanchez, et al., J. Med. Chem., 1988, 31, 983).

The following other quinolonyl lactam esters are made by the general procedures of this Example and Examples 1–4, with substantially similar results.
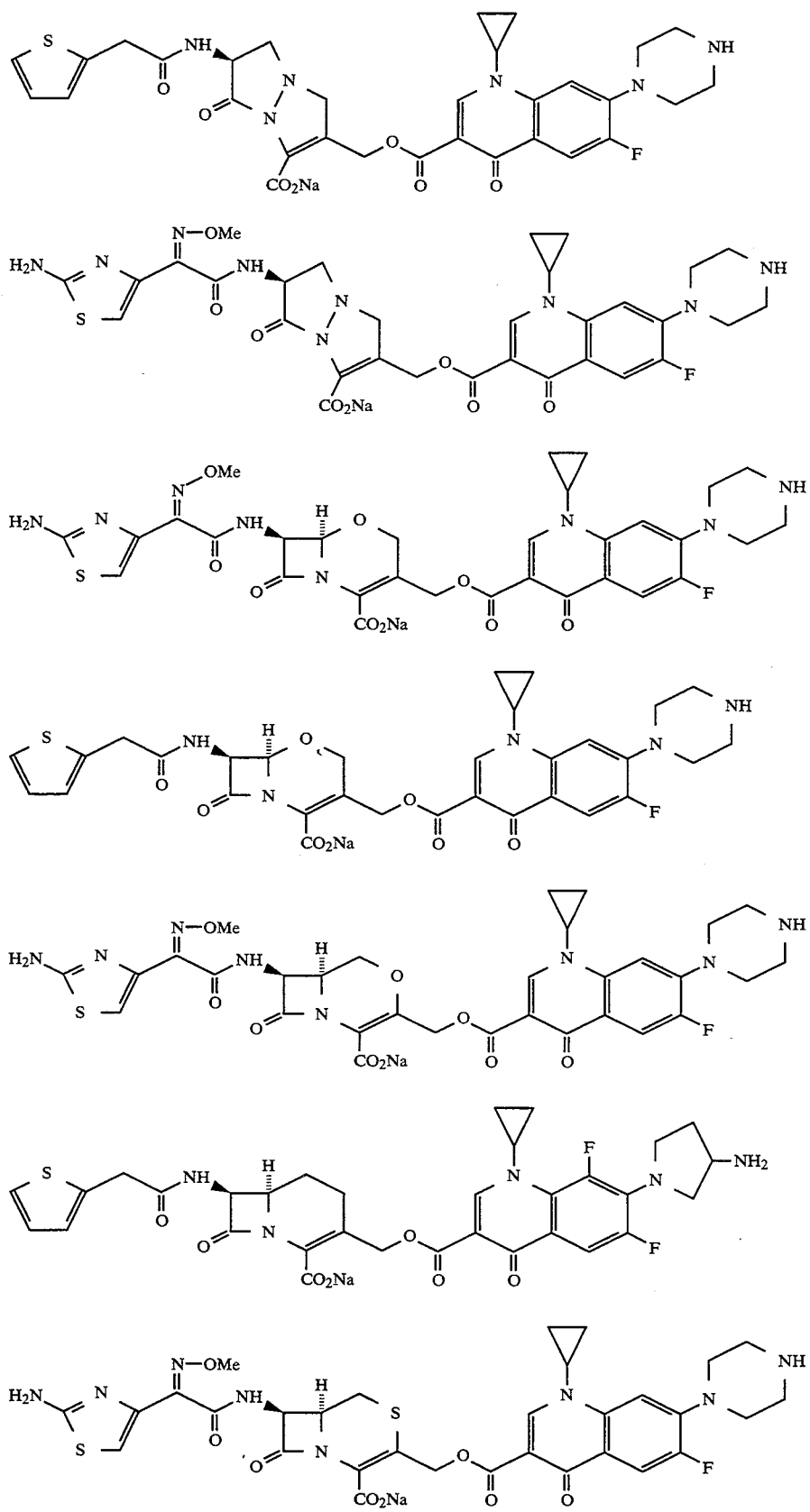

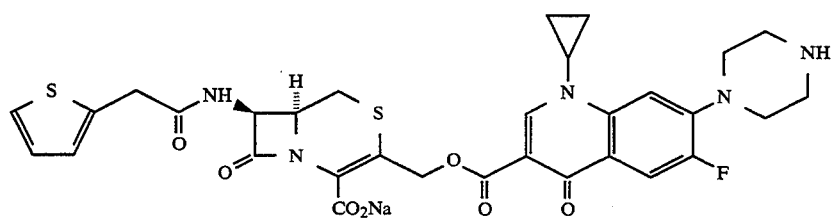
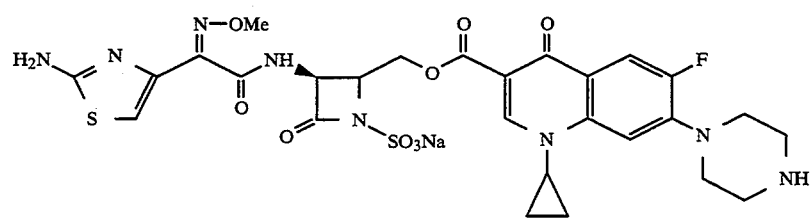
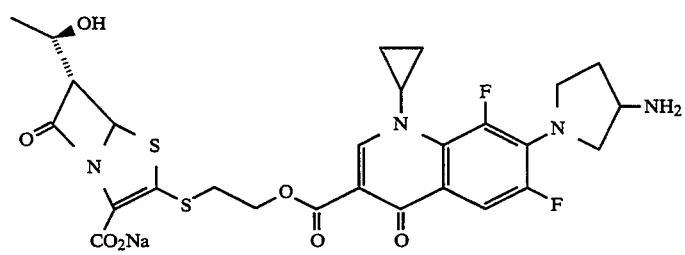
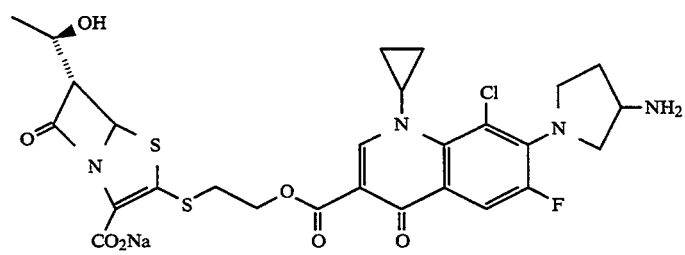
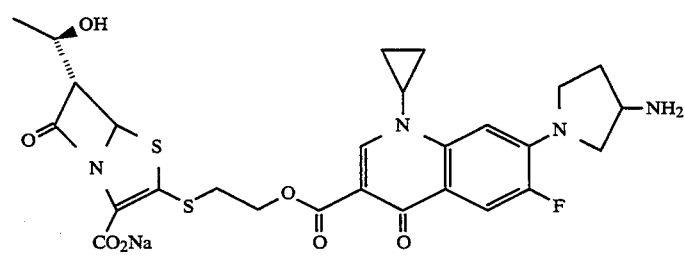
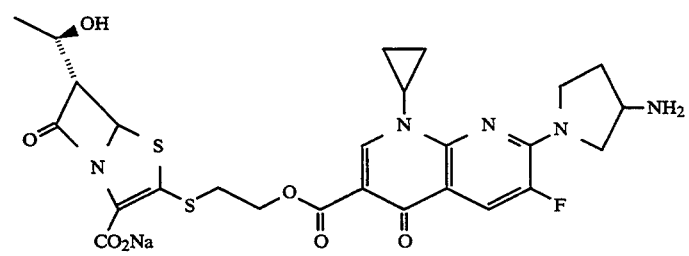

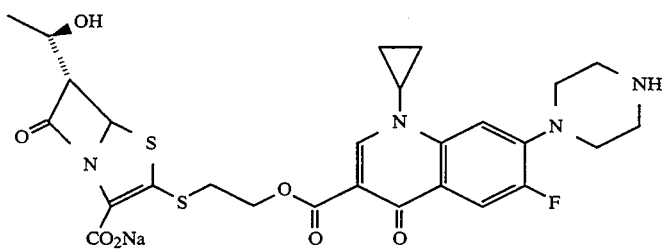
EXAMPLE 6
[3S-(2b,3b)]-2-[[1-Cyclopropyl-6-fluoro-1,4-dihydro-4-oxo-7-(1-piperazinyl)-3-quinolinyl]carbonyloxy]-3-[(phenoxyacetyl)amino-4-oxo-1-azetidinesulfonic acid sodium salt, according to this invention, is made by the following general reaction sequence.
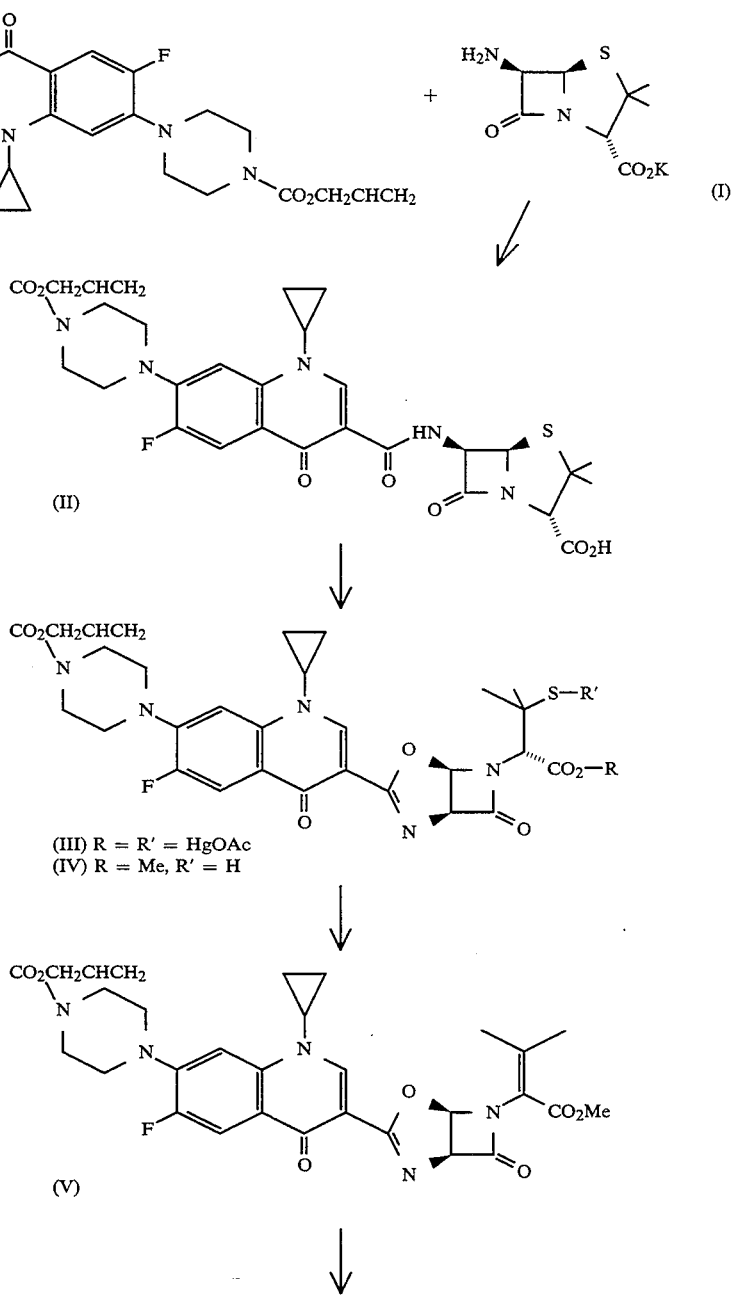

-continued

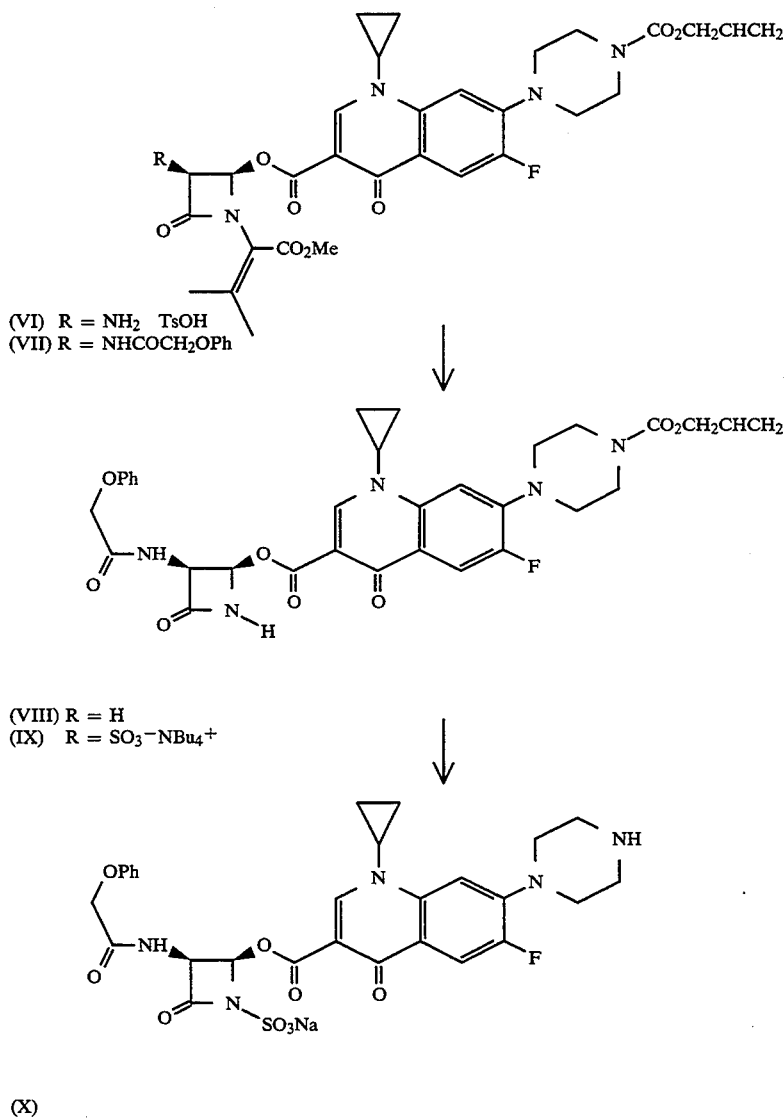

(VI) R = NH₂ TsOH
(VII) R = NHCOCH₂OPh (VIII) R = H
(IX) R = SO₃⁻NBu₄⁺

(X)

An anhydrous solution of approximately 20 g 1-ethyl-6-fluoro-1,4-dihydro-4-oxo-7-[4-[2-propenyloxy)carbonyl]-1-piperazinyl]-3-quinolinecarboxylic acid sodium salt and 6.4 ml of triethylamine in 100 ml of dioxane and 20 ml of acetone is cooled to 0° C. (32° F.). To this stirred solution is added 4.4 ml of ethylchloroformate dropwise keeping the temperature at 2° C. (36° F.). This solution is stirred at 0° C. (32° F.) for 45 minutes. A cooled solution of 7.8 g of 6-aminopenicillanic acid potassium salt (I), 4.2 ml of triethylamine and 9.6 ml of water is added all at once to the above mixed anhydride solution and stirred at room temperature until reaction is complete as per TLC (thin layer chromatography. The reaction mixture is washed with dichloromethane then the aqueous layer is acidified to pH 2 with 1N HCl. The aqueous layer is extracted with dichloromethane and the combined organic extracts are washed with water, dried over sodium sulfate and concentrated in vacuo to yield Product (II).

Approximately 13.0 g of Product (II) is added to a stirred solution of mercury(II) acetate (12.8 g) in acetic acid (200 ml), at room temperature. Acetone is mixed with the resulting gel and the insoluble material filtered off and washed with acetone and ether to give Product (III). An excess of diazomethane in ether is added to a stirred suspension of 11.9 g of the salt Product (III) in dimethyl sulfoxide (45 ml). After 2 hours the mixture is diluted with dichloromethane, filtered and washed with water. The organic layer is dried (sodium sulfate) and concentrated to give a mixture of products with the desired Product (IV) isolated by chromatography. This thiol (IV) (4.4 g) and mercury (II) acetate (1.08 g) in dimethyl sulfoxide (80 ml) are stirred for 18 hours. The mixture is then diluted with dichloromethane, filtered and washed with water. The organic layer is dried over sodium sulfate and evaporated to yield Product (V).

Approximately 2.95 g of Product (V) is dissolved in acetone (35 ml), and approximately 0.95 g of p-toluene sulfonic acid monohydrate is added. The mixture is stirred for 20 minutes at 18° C. (64° F.). The solvent is then evaporated to leave Product (VI), which is triturated. To a solution of 2.3 g of Product (VI) in dichloromethane (20 ml) is added 0.52 ml of phenoxyacetyl chloride with ice-bath cooling. This mixture is stirred and a solution of 0.55 ml of pyridine in dichloromethane (4 ml) is added during a period of 30 minutes. After stirring an additional 30 minutes, the mixture is concentrated, and the residue dissolved in dichloromethane, washed with dilute HCl, water, saturated sodium bicarbonate, and brine, and dried over sodium sulfate and evaporated to give Product (VII).

Product (VII) (approximately 0.91 g) is dissolved in 15 ml of acetone with 0.26 ml of acetic acid and cooled to 0° C. (32° F.). Approximately 0.25 g of potassium permanganate, dissolved in 10 ml of water, is added keeping the temperature at approximately 2° C. (36° F.). When the addition is complete, the mixture is warmed to room temperature and allowed to stir for 3 hours. The solid is then filtered, and washed with dichloromethane. The filtrate is diluted with water and the layers separated. The organic layer is washed with saturated sodium bicarbonate solution and water, dried and evaporated to give Product (VIII).

An anhydrous solution of approximately 0.46 g Product (VIII) in 4 ml of DMF is made, and approximately 0.95 g of DMF.SO$_3$ complex is added. This is allowed to stir 2 hours or until the reaction is complete as ,shown by TLC. The mixture is then diluted with 20 ml of dichloromethane and 20 ml of 0.5N potassium hydrogen phosphate solution with stirring. The pH is adjusted to 6 with 1N NaOH and 0.25 g of tetrabutylammonium hydrogen sulfate is added. The layers are separated and the organic layer is washed with water, dried and concentrated to yield Product (IX).

The product (IX) is taken up in approximately 10 ml of dichloromethane, 30 ml of water and 5 mg of bis(triphenylphosphine) palladium chloride. The mixture is treated with approximately 150 microliters of tributyl tin hydride while maintaining a temperature of approximately 21° C. (70° F.). After rapid stirring for approximately 5 minutes, the deprotected product is isolated by filtration. This is then taken up in water and methanol, filtered, and washed with water. The filtrate is concentrated to yield final Product (X) which is purified by trituration.

EXAMPLE 7

An antimicrobial composition for parenteral administration, according to this invention, is made comprising:

| Component | Amount |
|---|---|
| [5R][5α,6α]-3-[[7-[(3-amino-1-pyrrolidinyl)-6-fluoro-1-(2,4-difluorophenyl)-1,4-dihydro-4-oxo-3-(1,8-naphthyridinyl)]carbonyloxy]methyl]-6-(1(R)-hydroxyethyl)-7-oxo-4-thia-1-azabicyclo[3.2.0]hept-2-ene-2-carboxylic acid[1] | 100 mg/ml carrier |
| Carrier: | |
| sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

[1] a quinolonyl lactam ester, made according to Example 1

The above ingredients are mixed, forming a suspension. Approximately 2.0 ml of the suspension is systemically administered, via intramuscular injection, to a human subject suffering from a lower respiratory tract infection, with *Streptococcus pneumoniae* present. This dosage is repeated twice daily, for approximately 14 days. After 4 days, symptoms of the disease subside, indicating that the pathogen has been substantially eradicated.

EXAMPLE 8

An enteric coated antimicrobial composition for oral administration, according to this invention, is made comprising the following core tablet:

| Component | Amount (mg) |
|---|---|
| [5R][5α,6α]-3-[[7-[(3-amino-1-pyrrolidinyl)-6-fluoro-1-(2,4-difluorophenyl)-1,4-dihydro-4-oxo-3-(1,8-naphthyridinyl)]carbonyloxy]methyl]-6-(1(R)-hydroxyethyl)-7-oxo-4-thia-1-azabicyclo[3.2.0]hept-2-ene-2-carboxylic acid[1] | 350.0 |
| starch | 30.0 |
| magnesium stearate | 5.0 |
| microcrystalline cellulose | 100.0 |
| colloidal silicon dioxide | 2.5 |
| povidone | 12.5 |

[1] a quinolonyl lactam ester, made according to Example 1

The components are admixed into a bulk mixture. Compressed tablets are formed, using tabletting methods known in the art. The tablets are coated with a suspension of methacrylate acid/methacrylate ester polymer in isopropanol/acetone. A human subject, having a urinary tract infection with *Escherichia coli* present, is orally administered two of the tablets, every 8 hours, for 14 days. Symptoms of the disease then subside, indicating substantial eradication of the pathogen.

What is claimed is:

1. A compound of the formula

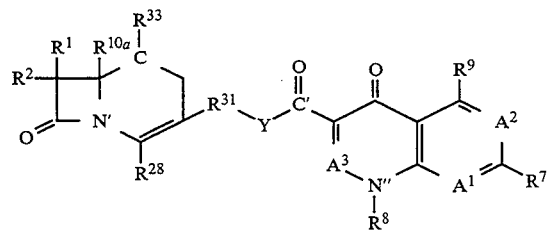

wherein
(A) $R^1$ is hydrogen; halogen; $C_1$-$C_8$ alkyl; $C_2$-$C_8$ alkenyl; a 3-8 atom heteroalkyl; a 3-9 atom monocyclic or 7-17 atom polycyclic carbocycle; 3-9 atom monocyclic or 7-17 atom polycyclic heterocycle; $R^{10a}$—O—; $R^{10a}$CH=N—; ($R^{10}$) ($R^{11}$)N—; $R^{12}$—C(=CHR$^{15}$)—C(=O)NH—; $R^{12}$—C(=NO—R$^{14}$)—C(=O)NH—; or $R^{13}$—(CH$_2$)$_m$—C(=O)NH—; wherein said heteroalkyl has carbon atoms and one or two heteroatoms selected from O, S, or N; and wherein said heterocycle has one or more heteroatoms selected from O, S, or N;
(1) m is an integer from 0 to 9;
(2) $R^{10}$ and $R^{11}$ are, independently, $R^{10a}$ where $R^{10a}$ is hydrogen; $C_1$-$C_8$ alkyl; $C_2$-$C_8$ alkenyl; a 3-9 atom monocyclic or 7-17 atom polycyclic carbocycle or a 3-9 atom monocyclic or 7-17 atom polycyclic heterocycle substituent; or $R^{10}$ and $R^{11}$ together form a 3-9 atom monocyclic or 7-17 atom polycyclic heterocycle including the nitrogen to which they are bonded; wherein said heterocycles have one or more heteroatoms selected from O, S, or N;

(3) $R^{12}$ is hydrogen; $C_1$-$C_8$ alkyl; $C_2$-$C_8$ alkenyl; a 3-8 atom heteroalkyl; a 3-8 atom heteroalkenyl; a 3-9 atom monocyclic or 7-17 atom polycyclic carbocycle; or a 3-9 atom monocyclic or 7-17 atom polycyclic heterocycle; wherein said heteroalkyl has carbon atoms and one or two heteroatoms selected from O, S, or N; wherein said heteroalkenyl has carbon atoms and one or two heteroatoms selected from O, S, or N; and wherein said heterocycles have one or more heteroatoms selected from O, S, or N;

(4) $R^{13}$ is $R^{12}$, $-Z^1$, or $-CH(Z^2)$ $(R^{12})$;

(5) $R^{14}$ is $R^{12}$, arylalkyl, heteroarylalkyl, $-C(R^{17})(R^{18})COOH$, $-C(=O)O-R^{12}$ or $-C(=O)NH-R^{12}$, where $R^{17}$ and $R^{18}$ are, independently, $R^{12}$ or together form a 3-9 atom monocyclic or 7-17 atom polycyclic carbocycle or a 3-9 atom monocyclic or 7-17 atom polycyclic heterocycle including the carbon atom to which $R^{17}$ and $R^{18}$ are bonded; wherein said arylalkyl is a $C_1$-$C_8$ alkyl substituted with an aryl group substituted with one or two heteroatoms selected from O, S, or N; wherein said heteroarylalkyl is a $C_1$-$C_8$ alkyl substituted with an aryl which is substituted with one or two heteroatoms selected from O, S, or N; and wherein said heterocycles have one or more heteroatoms selected from O, S, or N;

(6) $R^{15}$ is $R^{14}$, halogen, $-Z^1$, or $-CH(Z^2)$ $(R^{12})$;

(7) $Z^1$ is $-C(=O)OR^{16}$, $-C(=O)R^{16}$, $-N(R^{19})R^{16}$, $-S(O)_pR^{24}$, or $-OR^{24}$; and $Z^2$ is $Z^1$ or $-OH$, $-SH$, or $-SO_3H$;

(a) p is an integer from 0 to 2;

(b) $R^{19}$ is hydrogen; $C_1$-$C_8$ alkyl; $C_2$-$C_8$ alkenyl; a 3-8 atom heteroalkyl; a 3-8 member heteroalkenyl; a 3-9 atom monocyclic or 7-17 atom polycyclic carbocycle; a 3-9 atom monocyclic or 7-17 atom polycyclic heterocycle; $-SO_3H$; $-C(=O)R^{20}$; or, when $R^{13}$ is $-CH(Z^2)$ $(R^{12})$ and $Z^2$ is $-N(R^{19})R^{16}R^{19}R^{16}$ may together form a 3-9 atom monocyclic or 7-17 atom polycyclic heterocycle; wherein said heterocycles have one or more heteroatoms selected from O, S, or N; wherein said heteroalkyl has carbon atoms and one or two heteroatoms selected from O, S, or N; and wherein said heteroalkenyl has carbon atoms and one or two heteroatoms selected from O, S, or N;

(c) $R^{20}$ is $R^{12}$, $NH(R^{12})$, $N(R^{12})$ $(R^{21})$, $O(R^{21})$, or $S(R^{21})$; where $R^{21}$ is $C_1$-$C_8$ alkyl; $C_2$-$C_8$ alkenyl; a 3-9 atom monocyclic or 7-17 atom polycyclic carbocycle; a 3-9 atom monocyclic or 7-17 atom polycyclic heterocycle; or when $R^{20}$ is $N(R^{12})$ $(R^{21})$, $R^{21}$ and $R^{12}$ may together form a 3-9 atom monocyclic or 7-17 atom polycyclic heterocycle; wherein said heterocycles have one or more heteroatoms selected from O, S, or N; and (8) $R^{16}$ is $R^{24}$ or hydrogen; where $R^{24}$ is $C_1$-$C_8$ alkyl; $C_2$-$C_8$ alkenyl; arylalkyl; a 3-8 atom heteroalkyl; a 3-8 atom heteroalkenyl; heteroarylalkyl; a 3-9 atom monocyclic or 7-17 atom polycyclic carbocycle; a 3-9 atom monocyclic or 7-17 atom polycyclic heterocycle; or, when $Z^1$ is $N(R^{19})R^{16}$ and $R^{16}$ is $R^{24}$, $R^{16}$ and $R^{19}$ may together form a 3-9 atom monocyclic or 7-17 atom polycyclic heterocycle including the nitrogen atom to which $R^{19}$ is bonded; wherein said heterocycles have one or more heteroatoms selected from O, S, or N; wherein said arylalkyl is a $C_1$-$C_8$ alkyl substituted with an aryl group substituted with one or two heteroatoms selected from O, S, or N; wherein said heteroalkyl has carbon atoms and one or two heteroatoms selected from O, S, or N; wherein said heteroalkenyl has carbon atoms and one or two heteroatoms selected from O, S, or N; and wherein said heteroarylalkyl is a $C_1$-$C_8$ alkyl substituted with an aryl group substituted with one or more heteroatoms selected from O, S, or N;

(B) $R^2$ is hydrogen, halogen, alkoxy, or $R^{22}C(=O)NH-$, where $R^{22}$ is hydrogen or $C_1$-$C_8$ alkyl;

(C) $R^{28}$ is hydrogen or COOH;

(D) $R^{31}$ is nil, $C_1$-$C_8$, $C_2$-$C_8$ alkenyl, a 3-9 atom monocyclic or 7-17 atom polycyclic carbocycle; or a 3-9 atom monocyclic or 7-17 atom polycyclic heterocycle; wherein said heterocycles have one or more heteroatoms selected from O, S, N;

(E) $R^{33}$ is hydrogen, alkyl, or alkoxy;

(F) Y is O or $Z^4-R^{34}-O$, where
  (1) $Z^4$ is $-O-$; $-S(O)_t-$, where t is an integer of 0 to 2; or $-NR^{10a}-$;
  (2) $R^{34}$ is $C_1$-$C_8$ alkyl; $C_2$-$C_8$ alkenyl; a 3-8 atom heteroalkyl; a 3-8 atom heteroalkenyl; a 3-9 atom monocyclic or 7-17 atom polycyclic carbocycle; or a 3-9 atom monocyclic or 7-17 atom polycyclic heterocycle; wherein said heterocycle has one or more heteroatoms selected from O, S, or N;

(G)
  (1) $A^1$ is N or $C(R^{40})$; where $R^{40}$ is hydrogen, hydroxy, alkoxy, nitro, cyano, halogen, $C_1$-$C_8$ alkyl, or $N(R^{10})$ $(R^{11})$;
  (2) $A^2$ is N or $C(R^6)$; where $R^6$ is hydrogen or halogen;
  (3) $A^3$ is N or $C(R^{41})$; where $R^{41}$ is hydrogen;
  (4) $R^8$ is hydrogen; $C_1$-$C_8$ alkyl; a 3-9 atom monocyclic or 7-17 atom polycyclic carbocycle; a 3-9 atom monocyclic or 7-17 atom polycyclic heterocycle; alkoxy; hydroxy; $C_2$-$C_8$ alkenyl; arylalkyl; or $N(R^{10})$ $(R^{11})$; wherein said arylalkyl is a $C_1$-$C_8$ alkyl substituted with an aryl group substituted with one or two heteroatoms selected from O, S, or N; and wherein said heterocycle has one or more heteroatoms selected from O, S, or N;
  (5) $R^7$ is hydrogen, halogen, $C_1$-$C_8$ alkyl, a 3-9 atom monocyclic or 7-17 atom polycyclic carbocycle; or a 3-9 atom monocyclic or 7-17 atom polycyclic heterocycle; wherein said heterocycle has one or more heteroatoms selected from O, S, or N;
  (7) $R^9$ is hydrogen, halogen, nitro, or $N(R^{10})$ $(R^{11})$;

(H) except that
  (1) when $A^1$ is $C(R^{40})$, $R^8$ and $R^{40}$ may together form a 3-9 atom monocyclic or 7-17 atom polycyclic heterocycle including N" and $A^1$; wherein said heterocycle has one or more heteroatoms selected from O, S, or N;
  (2) when $A^2$ is $C(R^6)$, $R^6$ and $R^7$ may together form $-O-(CH_2)_n-O-$, where n is an integer from 1 to 4; and
  (3) when $A^3$ is $C(R^{41})$, $R^8$ and $R^{41}$ may together form a 3-9 atom monocyclic or 7-17 atom polycyclic heterocycle including N" and the adjacent carbon to which $R^{41}$ is bonded; wherein said heterocycle has one or more heteroatoms selected from O, S, or N;

and pharmaceutically-acceptable salts and biohydrolyzable esters thereof, and hydrates thereof.

2. A compound of the formula

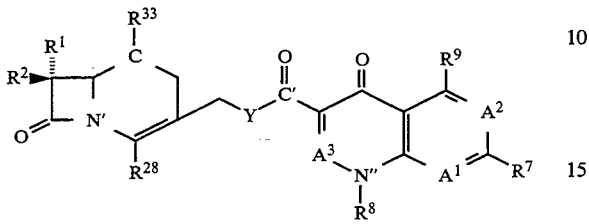

wherein (A) $R^1$ is hydrogen; halogen; $C_1$-$C_8$ alkyl; $C_2$-$C_8$ alkenyl; a 3-8 atom heteroalkyl; a 3-9 atom monocyclic or 7-17 atom polycyclic carbocycle; a 3-9 atom monocyclic or 7-17 atom polycyclic heterocycle; $R^{10a}$—O—; $R^{10a}CH=N$—; $(R^{10})(R^{11})N$—; $R^{12}$—C(=CHR$^{15}$)—C(=O)NH—; $R^{12}$—C(=NO—R$^{14}$)—C(=O)NH—; or $R^{13}$—(CR$_2$-)$_m$—C(=O)NH—; wherein said heteroalkyl has carbon atoms and one or two heteroatoms selected from O, S, or N; and wherein said heterocycle has one or more heteroatoms selected from O, S, or N;

(1) m is an integer from 0 to 9;

(2) $R^{10}$ and $R^{11}$ are, independently, $R^{10a}$ where $R^{10a}$ is hydrogen; $C_1$-$C_8$ alkyl; $C_2$-$C_8$ alkenyl; a 3-9 atom monocyclic or 7-17 atom polycyclic carbocycle or a 3-9 atom monocyclic or 7-17 atom polycyclic heterocycle substituent; wherein said heterocycle has one or more heteroatoms selected from O, S, or N; or $R^{10}$ and $R^{11}$ together form a 3-9 atom monocyclic or 7-17 atom polycyclic heterocycle including the nitrogen to which they are bonded; wherein said heterocycles have one or more heteroatoms selected from O, S, or N;

(3) $R^{12}$ is hydrogen; $C_1$-$C_8$ alkyl; $C_2$-$C_8$ alkenyl; a 3-8 atom heteroalkyl; a 3-8 atom heteroalkenyl; a 3-9 atom monocyclic or 7-17 atom polycyclic carbocycle; or a 3-9 atom monocyclic or 7-17 atom polycyclic heterocycle; wherein said heteroalkyl has carbon atoms and one or two heteroatoms selected from O, S, or N; wherein said heteroalkenyl has carbon atoms and one or two heteroatoms selected from O, S, or N; and wherein said heterocycle has one or more heteroatoms selected from O, S, or N;

(4) $R^{13}$ is $R^{12}$, —$Z^1$, or —CH($Z^2$) ($R^{12}$);

(5) $R^{14}$ is $R^{12}$ arylalkyl heteroarylalkyl —C($R^{17}$)($R^{18}$)COOH, —C(=O)O—$R^{12}$ or —C(=O)NH—$R^{12}$, where $R^{17}$ and $R^{18}$ are, independently, $R^{12}$ or together form a 3-9 atom monocyclic or 7-17 atom polycyclic carbocycle or a 3-9 atom monocyclic or 7-17 atom polycyclic heterocycle including the carbon atom to which $R^{17}$ and $R^{18}$ are bonded; wherein said heterocycle has one or more heteroatoms selected from O, S, or N; wherein said arylalkyl is a C1—$C_8$ alkyl substituted with an aryl group substituted with one or two heteroatoms selected from O, S, or N; and wherein said heteroarylalkyl is a $C_1$-$C_8$ alkyl substituted with an aryl group substituted with one or more heteroatoms selected from O, S, or N;

(6) $R^{15}$ is $R^{14}$, halogen, —$Z^1$, or —CH($Z^2$) ($R^{12}$);

(7) $Z^1$ is —C(=O)OR$^{16}$ —C(=O)R$^{16}$, —N(R$^{19}$)R$^{16}$, —S(O)$_p$R$^{24}$, or —OR$^{24}$; and $Z^2$ is $Z^1$ or —OH, —SH, or —SH$_3$H;

(a) p is an integer from 0 to 2;

(b) $R^{19}$ is hydrogen; $C_1$-$C_8$ alkyl; $C_2$-$C_8$ alkenyl; a 3-8 atom heteroalkyl; a 3-8 atom heteroalkenyl; a 3-9 atom monocyclic or 7-17 atom polycyclic carbocycle; a 3-9 atom monocyclic or 7-17 atom polycyclic heterocycle; —SO$_3$H; —C(=O)R$^{20}$; or, when $R^{13}$ is —CH($Z^2$) ($R^{12}$) and $Z^2$ is —N($R^{19}$)R$^{16}$, $R^{19}$ and $R^{16}$ form a 3-9 atom monocyclic or 7-17 atom polycyclic heterocycle; wherein said heterocycle has one or more heteroatoms selected from O, S, or N; wherein said heteroalkyl has carbon atoms and one or two heteroatoms selected from O, S, or N; and wherein said heteroalkenyl has carbon atoms and one or two heteroatoms selected from O, S, or N;

(c) $R^{20}$ is $R^{12}$, NH($R^{12}$), N($R^{12}$)($R^{21}$), O($R^{21}$), or S($R^{21}$); where $R^{21}$ is $C_1$-$C_8$ alkyl; $C_2$-$C_8$ alkenyl; a 3-9 atom monocyclic or 7-17 atom polycyclic carbocycle; a 3-9 atom monocyclic or 7-17 atom polycyclic heterocycle; or when $R^{20}$ is N($R^{12}$)($R^{21}$), $R^{21}$ and $R^{12}$ may together form a 3-9 atom monocyclic or 7-17 atom polycyclic heterocycle; wherein said heterocycles have one or more heteroatoms selected from O, S, or N;

(8) $R^{16}$ is $R^{24}$ or hydrogen; where $R^{24}$ is $C_1$-$C_8$ alkyl; $C_2$—$C_8$ alkenyl; arylalkyl; a 3-8 atom heteroalkyl; a 3-8 atom heteroalkenyl; heteroarylalkyl; a 3-9 atom monocyclic or 7-17 atom polycyclic carbocycle; a 3-9 atom monocyclic or 7-17 atom polycyclic heterocycle; or, when $Z^1$ is N($R^{19}$)R$^{16}$ and $R^{16}$ is $R^{24}$ $R^{16}$ and $R^{19}$ may together form a 3-9 atom monocyclic or 7-17 atom polycyclic heterocycle including the nitrogen atom to which $R^{19}$ is bonded; wherein said arylalkyl is a $C_1$-$C_8$ alkyl substituted with an aryl group; wherein said heteroalkyl has carbon atoms and one or two heteroatoms selected from O, S, or N; wherein said heteroarylalkyl is a $C_1$-$C_8$ alkyl substituted with an aryl group substituted with one or two heterocarbons selected from O, S, or N; wherein said heteroalkenyl has carbon atoms and one or two heteroatoms selected from O, S, or N; and wherein said heterocycles have one or more heteroatoms selected from O, S, or N;

(B) $R^{33}$ is hydrogen, alkyl, or alkoxy;

(C) $R^2$ is hydrogen, halogen, alkoxy, or $R^{22}$C(=O)NH—, where $R^{22}$ is hydrogen or $C_1$-$C_8$ alkyl;

(D)

(1) $A^1$ is N or C($R^{40}$); where $R^{40}$ is hydrogen, hydroxy, alkoxy, nitro, cyano, halogen, $C_1$-$C_8$ alkyl, or N($R^{10}$)($R^{11}$);

(2) $A^2$ is N or C($R^6$); where $R^6$ is hydrogen or halogen;

(3) $A^3$ is N or C($R^{41}$); where $R^{41}$ is hydrogen;

(4) $R^8$ is hydrogen; $C_1$-$C_8$ alkyl; a 3-9 atom monocyclic or 7-17 atom polycyclic carbocycle; a 3-9 atom monocyclic or 7-17 atom polycyclic heterocycle; alkoxy; hydroxy; C₂-C₈ alkenyl; arylalkyl; or N(R¹⁰) (R¹¹); wherein said heterocycle has one or more heteroatoms selected from O, S, or N; and wherein said arylalkyl is a C₁-C₈ alkyl with an aryl substituent;

(5) R⁷ is hydrogen, halogen, C₁-C₈ alkyl, a 3-9 atom monocyclic or 7-17 atom polycyclic carbocycle; or a 3-9 atom monocyclic or 7-17 atom polycyclic heterocycle; and (6) R⁹ is hydrogen, halogen, nitro, or N(R¹⁰) (R¹¹);

(E) except that (1) when A¹ is C(R⁴⁰), R⁸ and R⁴⁰ may together form a 3-9 atom monocyclic or 7-17 atom polycyclic heterocycle including N″ and A¹; wherein said heterocycle has one or more heteroatoms selected from O, S, or N;

(2) when A² is C(R⁶), R⁶ and R⁷ may together form —O—(CH₂)ₙ—O—, where n is an integer from 1 to 4; and (3) when A³ is C(R⁴¹), R⁸ and R⁴¹ may together form a 3-9 atom monocyclic or 7-17 atom polycyclic heterocycle including N″ and the adjacent carbon to which R⁴¹ is bonded;

and pharmaceutically-acceptable salts and biohydrolyzable esters thereof, and hydrates thereof.

3. A compound, according to claim 2, wherein R¹³ is a C₁-C₈ alkyl or a C₂-C₈ alkenyl.

4. A compound, according to claim 2, wherein R² is hydrogen or C₁-C₈ alkoxy.

5. A compound, according to claim 2, wherein: A¹ is C(R⁴⁰), A² is C(R⁶), and A³(R⁴¹); or A¹ is nitrogen, A² is C(R⁶), and A³ is C(R⁴¹).

6. A compound, according to claim 2, wherein A¹ is C(R⁴⁰), A² is C(R⁶), and A³ is C(R⁴¹).

7. A compound, according to claim 6, containing a 6-fluoroquinolone moiety, a 8-halo-6-fluoroquinolone moiety, a pyridobenzoxazine moiety, a pyridobenzthiazine moiety, a isothiazoloquinolinedione, or isoxazoloquinolinedione moiety.

8. A compound, according to claim 6, wherein R⁸ is a C₁-C₈ alkyl, aryl, cycloalkyl, or alkylamino.

9. A compound, according to claim 8, wherein R⁸ is ethyl, 2-fluoroethyl, 2-hydroxyethyl, t-butyl, 4-fluorophenyl, 2,4-difluorophenyl, methylamino or cyclopropyl.

10. A compound, according to claim 8, wherein R⁴⁰ is hydrogen or halo.

11. A compound, according to claim 10, wherein R⁴⁰ is chlorine or fluorine.

12. A compound, according to claim 10, wherein R⁷ is a nitrogen-containing 3-9 atom monocyclic or 7-17 atom polycyclic heterocycle.

13. A compound, according to claim 12, wherein R⁷ is piperazine, 3-methylpiperazine, 3-aminopyrrolidine, 3-aminomethylpyrrolidine, N,N-dimethylaminomethylpyrrolidine, N-methylaminomethylpyrrolidine, N-ethylaminomethylpyrrolidine, pyridine, N-methylpiperazine, or 3,5-dimethylpiperazine.

14. A compound, according to claim 13, wherein R⁸ is cyclopropyl, and R² is fluorine.

15. A compound, according to claim 14, wherein R⁷ is piperazine.

16. A compound of the formula

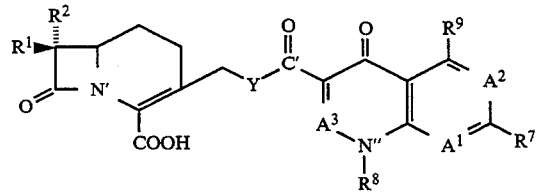

wherein (A) R¹ is C₁-C₈ alkyl; C₂-C₈ alkenyl; R¹²—C(=NO—R¹⁴)—C(=O)NH—, or R¹³—(CH₂)ₘ—C(=O)NH—; where (1) m is an integer from 0 to 3;

R¹⁰ and R¹¹ are, independently, R¹⁰ᵃ where R¹⁰ᵃ is hydrogen; C₁-C₈ alkyl; C₂-C₈ alkenyl; 3-9 atom monocyclic or 7-17 atom polycyclic carbocycle, or 3-9 atom monocyclic or 7-17 atom polycyclic heterocycle substituents; or R¹⁰ and R¹¹ together form a 3-9 atom monocyclic or 7-17 atom polycyclic heterocycle including the nitrogen to which they are bonded; wherein said heterocycles have one or more heteroatoms selected from O, S, or N;

(3) R¹² is C₁-C₈ alkyl; a 3-9 atom monocyclic or 7-17 atom polycyclic carbocycle; or a 3-9 atom monocyclic or 7-17 atom polycyclic heterocycle; wherein said heterocycle has one or more heteroatoms selected from O, S, or N;

(4) R¹³ is R¹², —Z¹, or —CH(Z²) (R¹²);

(5) R¹⁴ is R¹² or —C(R¹⁷) (R¹⁸)COOH);

(6) R¹⁵ is R¹⁴ or halogen;

(7) Z¹ is —C(=O)OR¹⁶, —C(=O)R¹⁶—N(R¹⁹)R¹⁶, —S(O)ₚR²⁴, or —OR²⁴; and Z² is Z¹ or —OH, —SH, or —SO₃H;

(a) p is 0;

(b) R¹⁹ is hydrogen; C₁-C₈ alkyl; C₂-C₈ alkenyl; a 3-8 atom heteroalkyl; a 3-8 atom heteroalkenyl; a 3-9 atom monocylic or 7-17 atom polycyclic carbocycle; a 3-9 atom monocyclic or 7-17 atom polycyclic heterocycle; —SO₃H; —C(=O)R²⁰; or, when R¹³ is —CH(Z²) (R¹²) and Z² is —N(R¹⁹)R¹⁶, R¹⁹ and R¹⁶ may together form a 3-9 atom monocyclic or 7-17 atom polycyclic heterocycle; wherein said heteroalkyl has carbon atoms and one or two heteroatoms selected from O, S, or N; and wherein said heteroalkenyl has carbon atoms and one or two heteroatoms selected from O, S, or N;

(c) R²⁰ is R¹², NH(R¹²), N(R¹²) (R²¹); where R²¹ is C₁-C₈ alkyl; C₂-C₈ alkenyl; a 3-9 atom monocyclic or 7-17 atom polycyclic carbocycle; a 3-9 atom monocyclic or 7-17 atom polycyclic heterocycle; or when R²⁰ is N(R¹²) (R²¹), R²¹ and R¹² may together form a 3-9 atom monocyclic or 7-17 atom polycyclic heterocycle; wherein said heterocycles have one or more heteroatoms selected from O, S, or N;

(8) R¹⁶ is hydrogen; C₁-C₈ alkyl; a 3-9 atom monocyclic or 7-17 atom polycyclic carbocycle; or a 3-9 atom monocyclic or 7-17 atom polycyclic heterocycle; wherein said heterocycle has one or more heteroatoms selected from O, S, or N;

(B) R² is hydrogen or alkoxy;

(C)

(1) $A^1$ is N or $C(R^{40})$; where $R^{40}$ is hydrogen or halogen;
(2) $A^2$ is $C(R^6)$; where $R^6$ is hydrogen or halogen;
(3) $A^3$ is $C(R^{41})$; where $R^{41}$ is hydrogen;
(4) $R^8$ is $C_1$–$C_8$ alkyl or a 3–9 atom monocyclic or 7–17 atom polycyclic carbocycle;
(5) $R^7$ is a 3–9 atom monocyclic or 7–17 atom polycyclic heterocycle; and
(6) $R^9$ is hydrogen;

(D) except that
(1) when $A^1$ is $C(R^{40})$, $R^8$ and $R^{39}$ may together form a 3–9 atom monocyclic or 7–17 atom polycyclic heterocycle including N" and $A^1$; wherein said heterocycle has one or more heteroatoms selected from O, S, or N;
(2) when $A^2$ is C ($R^6$), $R^6$ and $R^7$ may together form —O—$(CH_2)_n$—O—, where n is an integer from 1 to 4; and
(3) when $A^3$ is $C(R^{41})$, $R^8$ and $R^{41}$ may together form a 3–9 atom monocyclic or 7–17 atom polycyclic heterocycle including N" and the adjacent carbon to which $R^{41}$ is bonded; wherein said heterocycle has one or more heteroatoms selected from O, S, or N;

and pharmaceutically-acceptable salts and biohydrolyzable esters thereof, and hydrates thereof.

17. A composition for treating or preventing an infectious disorder in a human or other animal subject, comprising:
(1) a safe and effective amount of a compound of claim 1; and
(2) a pharmaceutically-acceptable carrier.

18. A composition for treating or preventing an infectious-disorder in a human or other animal subject, comprising:
(1) a safe and effective amount of a compound of claim 2; and
(2) a pharmaceutically-acceptable carrier.

19. A composition for treating or preventing an infectious disorder in a human or other animal subject, comprising:
(1) a safe and effective amount of a compound of claim 6; and
(2) a pharmaceutically-acceptable carrier.

20. A composition for treating or preventing an infectious disorder in a human or other animal subject, comprising:
(1) a safe and effective amount of a compound of claim 13; and
(2) a pharmaceutically-acceptable carrier.

21. A composition for treating or preventing an infectious disorder in a human or other animal subject, comprising:
(1) a safe and effective amount of a compound of claim 15; and
(2) a pharmaceutically-acceptable carrier.

22. A composition for treating or preventing an infectious disorder in a human or other animal subject, comprising:
(1) a safe and effective amount of a compound of claim 16; and
(2) a pharmaceutically-acceptable carrier.

23. A composition for treating or preventing an infectious disorder in a human or other animal subject, according to claim 17, wherein said composition is suitable for parenteral administration.

24. A composition for treating or preventing an infectious disorder in a human or other animal subject, according to claim 17, wherein said composition is suitable for oral administration.

25. A method for preventing or treating an infectious disorder in a human or other animal subject, by administering to said subject a safe and effective amount of a compound of claim 1.

26. A method for preventing or treating an infectious disorder in a human or other animal subject, by administering to said subject a safe and effective amount of a compound of claim 2.

27. A method for preventing or treating an infectious disorder in a human or other animal subject, by administering to said subject a safe and effective amount of a compound of claim 6.

28. A method for preventing or treating an infectious disorder in a human or other animal subject, by administering to said subject a safe and effective amount of a compound of claim 15.

29. A method for preventing or treating an infectious disorder in a human or other animal subject, by administering to said subject a safe and effective amount of a compound of claim 16.

* * * * *